(12) United States Patent
Daugs et al.

(10) Patent No.: US 9,845,285 B2
(45) Date of Patent: *Dec. 19, 2017

(54) CRYSTALLINE SOLID AND AMORPHOUS FORMS OF (−)-HALOFENATE AND METHODS RELATED THERETO

(71) Applicants: CymaBay Therapeutics, Inc., Newark, CA (US); Diatex, Inc., San Antonio, TX (US)

(72) Inventors: Edward D. Daugs, Midland, MI (US); Eric J. Hagen, Lafayette, IN (US); Jason A. Hanko, West Lafayette, IN (US); David H. Louks, Saginaw, MI (US)

(73) Assignees: CymaBay Therapeutics, Inc., Newark, CA (US); DiaTex, Inc., San Antonio, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/957,962

(22) Filed: Dec. 3, 2015

(65) Prior Publication Data

US 2016/0280636 A1 Sep. 29, 2016

Related U.S. Application Data

(63) Continuation of application No. 14/631,629, filed on Feb. 25, 2015, now Pat. No. 9,233,914, which is a
(Continued)

(51) Int. Cl.
*A61K 31/22* (2006.01)
*C07C 67/02* (2006.01)
(Continued)

(52) U.S. Cl.
CPC .......... *C07C 233/18* (2013.01); *A61K 9/0053* (2013.01); *A61K 31/216* (2013.01);
(Continued)

(58) Field of Classification Search
CPC ................ C07C 235/78; C07C 233/18; C07B 2200/07; C07B 2200/13; A61K 31/22
(Continued)

(56) References Cited

U.S. PATENT DOCUMENTS 3,953,490 A 4/1976 Shuman
6,262,118 B1 7/2001 Luskey et al.
(Continued)

OTHER PUBLICATIONS

U.S. Appl. No. 11/408,609 claims the benefit of U.S. Appl. No. 60/673,655, filed Apr. 20, 2005.
(Continued)

*Primary Examiner* — T. Victor Oh
(74) *Attorney, Agent, or Firm* — Hamilton, DeSanctis & Cha, LLP

(57) ABSTRACT

The present invention provides crystalline solid and amorphous forms of (−)-halofenate. The crystalline solid forms may be used in various pharmaceutical compositions, and are particularly effective for the prevention and/or treatment of conditions associated with blood lipid deposition in a mammal, particularly those diseases related to Type 2 diabetes and hyperlipidemia. The invention also relates to a method for preventing or treating Type 2 diabetes and hyperlipidemia in a mammal comprising the step of administering a therapeutically effective amount of crystalline solid and amorphous forms of (−)-halofenate.

20 Claims, 47 Drawing Sheets

XRPD Pattern of Form A

Related U.S. Application Data continuation of application No. 13/938,548, filed on Jul. 10, 2013, now Pat. No. 8,993,797, which is a continuation of application No. 13/470,142, filed on May 11, 2012, now Pat. No. 8,507,719, which is a continuation of application No. 14/408,609, filed on Apr. 20, 2006, now Pat. No. 8,203,019.

(60) Provisional application No. 60/673,655, filed on Apr. 20, 2005.

(51) Int. Cl.
*C07C 233/18* (2006.01)
*C07C 235/78* (2006.01)
*A61K 9/00* (2006.01)
*A61K 31/216* (2006.01)

(52) U.S. Cl.
CPC ........ *C07C 235/78* (2013.01); *C07B 2200/07* (2013.01); *C07B 2200/13* (2013.01)

(58) Field of Classification Search
USPC .......................................... 560/250; 514/551
See application file for complete search history.

(56) References Cited

U.S. PATENT DOCUMENTS

| | | | |
|---|---|---|---|
| 8,203,019 B2* | 6/2012 | Daugs | C07C 233/18 560/228 |
| 8,507,719 B2* | 8/2013 | Daugs | C07C 233/18 560/250 |
| 8,993,797 B2 | 3/2015 | Daugs et al. | |
| 9,233,914 B2 | 1/2016 | Daugs et al. | |

OTHER PUBLICATIONS

Albers et al., "Characterization of the Polymorphic Behavior of an Organic Compound Using a Dynamic Thermal and X-ray Powder Diffraction Technique", Org. Proc. Res. Dev., vol. 11, pp. 846-860 (2007).

* cited by examiner

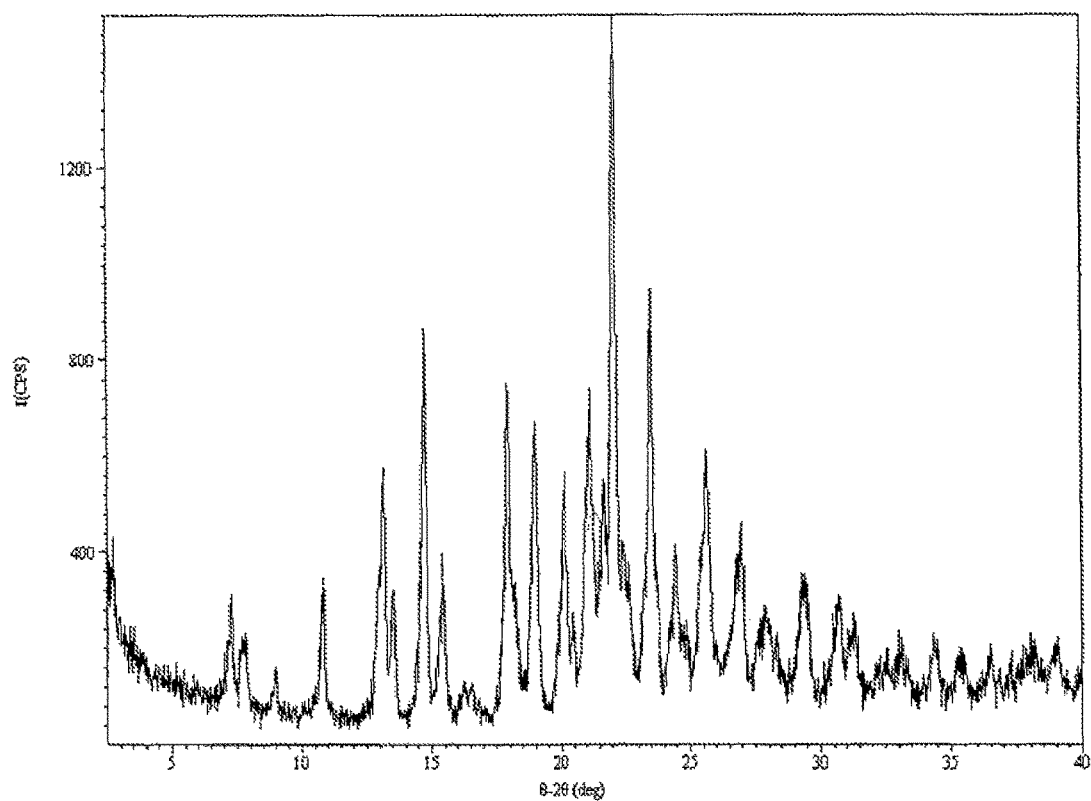
Figure 1. XRPD Pattern of Form A

Figure 2. XRPD Peak Listing for Form A

* Basic Data Process *

```
# Strongest 3 peaks
  no.  peak    2Theta         d         I/I1    FWHM       Intensity   Integrated Int
       no.     (deg)         (A)                (deg)      (Counts)    (Counts)
    1    23    22.0479    4.02836      100     0.21580       363         3833
    2    27    23.4654    3.78812       57     0.21840       208         2325
    3    10    14.7181    6.01389       53     0.21090       192         2010

# Peak Data List
       peak    2Theta         d         I/I1    FWHM       Intensity   Integrated Int
       no.     (deg)         (A)                (deg)      (Counts)    (Counts)
         1     2.7383    32.23835        5     0.14330        19          150
         2     7.2637    12.16033       13     0.20250        47          611
         3     7.7525    11.39468        9     0.29500        32          510
         4     8.9620     9.85940        6     0.20400        22          267
         5    10.7946     8.18933       18     0.20270        64          798
         6    12.8600     6.87834       13     0.16000        47          492
         7    13.0829     6.76165       36     0.30180       131         1601
         8    13.4980     6.55463       17     0.21200        63          689
         9    14.4600     6.12065        9     0.17340        33          448
        10    14.7181     6.01389       53     0.21090       192         2010
        11    15.3965     5.75040       19     0.26300        69         1014
        12    16.2325     5.45608        3     0.37500        12          131
        13    16.5166     5.36286        4     0.19330        14          160
        14    17.6680     5.01813       10     0.10400        35          320
        15    17.9133     4.94774       49     0.23850       178         2127
        16    18.2400     4.85985       15     0.18000        55          770
        17    18.9601     4.67687       41     0.25850       149         2220
        18    19.8200     4.47586        6     0.16000        21          245
        19    20.0869     4.41699       29     0.25380       104         1281
        20    20.4366     4.34219        7     0.15330        26          211
        21    21.0793     4.21122       38     0.32140       138         2332
        22    21.6400     4.10336       26     0.29340        95         1569
        23    22.0479     4.02836      100     0.21580       363         3833
        24    22.4000     3.96583       19     0.25140        70          900
        25    22.6200     3.92775       11     0.18000        40          431
        26    23.1400     3.84065        9     0.10000        34          272
        27    23.4654     3.78812       57     0.21840       208         2325
        28    23.7000     3.75115       14     0.12880        50          459
        29    24.1800     3.67776        6     0.09340        21          133
        30    24.4091     3.64376       18     0.21820        66          685
        31    24.7800     3.59006        7     0.28580        24          363
        32    25.2800     3.52017       10     0.10000        35          277
        33    25.5873     3.47859       33     0.32130       120         1883
        34    25.9810     3.42676        4     0.09800        13           87
        35    26.3800     3.37583        3     0.06660        11           41
        36    26.5600     3.35336        6     0.24000        21          242
        37    26.7800     3.32631       16     0.25340        57          450
        38    26.9200     3.30933       20     0.26660        71          729
        39    27.5400     3.23622        5     0.14000        19          151
        40    27.9143     3.19367        9     0.34860        33          584
        41    28.2875     3.15237        6     0.12500        23          164
        42    29.0600     3.07031        6     0.11200        21          144
        43    29.3328     3.04237       16     0.38570        58         1090
        44    30.4800     2.93043        8     0.15200        30          287
        45    30.6600     2.91363       13     0.23340        49          546
        46    31.0400     2.87882        7     0.17340        24          206
        47    31.2600     2.85906        9     0.29340        32          436
```

Figure 2. (Cont'd) XRPD Peak Listing for Form A

| peak no. | 2Theta (deg) | d (Å) | I/I1 | FWHM (deg) | Intensity (Counts) | Integrated Int (Counts) |
|---|---|---|---|---|---|---|
| 48 | 32.1680 | 2.78040 | 4 | 0.14400 | 14 | 106 |
| 49 | 32.5366 | 2.74974 | 4 | 0.24670 | 14 | 180 |
| 50 | 32.9600 | 2.71538 | 5 | 0.20000 | 19 | 137 |
| 51 | 33.0800 | 2.70580 | 6 | 0.21340 | 21 | 179 |
| 52 | 33.3600 | 2.68373 | 4 | 0.10660 | 13 | 110 |
| 53 | 34.1600 | 2.62268 | 3 | 0.12000 | 11 | 113 |
| 54 | 34.3200 | 2.61082 | 8 | 0.17000 | 30 | 231 |
| 55 | 34.4800 | 2.59907 | 6 | 0.13000 | 22 | 199 |
| 56 | 35.2600 | 2.54334 | 6 | 0.20000 | 21 | 224 |
| 57 | 35.5000 | 2.52670 | 4 | 0.16000 | 16 | 156 |
| 58 | 36.4966 | 2.45996 | 5 | 0.20670 | 18 | 277 |
| 59 | 37.2733 | 2.41046 | 3 | 0.09330 | 11 | 79 |
| 60 | 38.0695 | 2.36186 | 5 | 0.13100 | 17 | 195 |
| 61 | 38.2280 | 2.35243 | 4 | 0.13600 | 13 | 100 |
| 62 | 38.9000 | 2.31332 | 4 | 0.20000 | 15 | 141 |
| 63 | 39.0400 | 2.30535 | 6 | 0.17340 | 20 | 158 |
| 64 | 39.9600 | 2.25437 | 3 | 0.16000 | 12 | 103 |

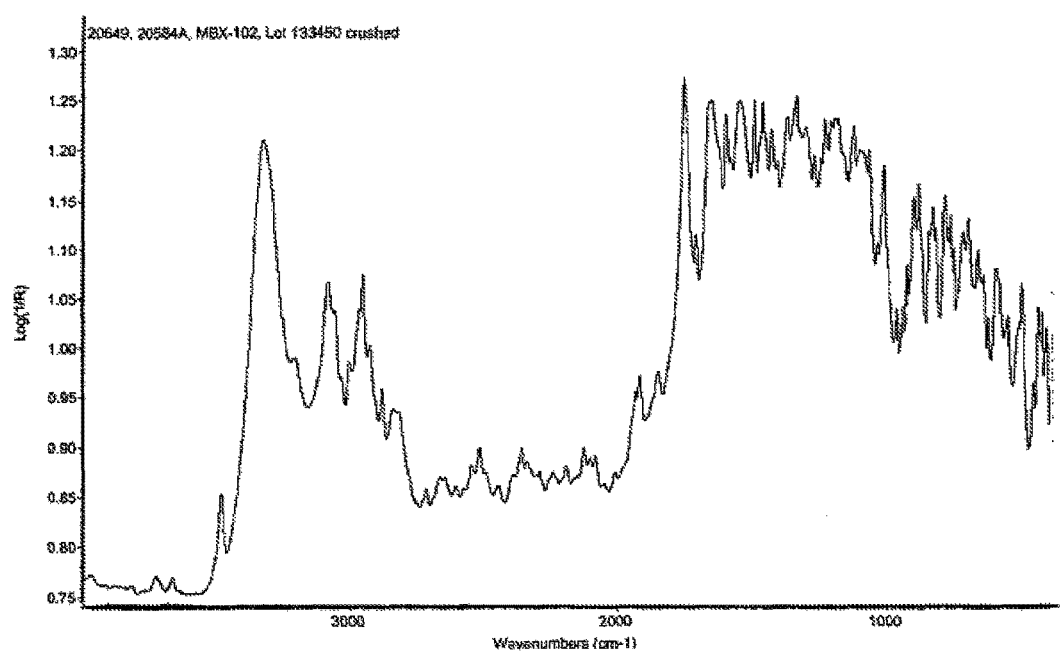
Figure 3. FT-IR Spectrum of Form A

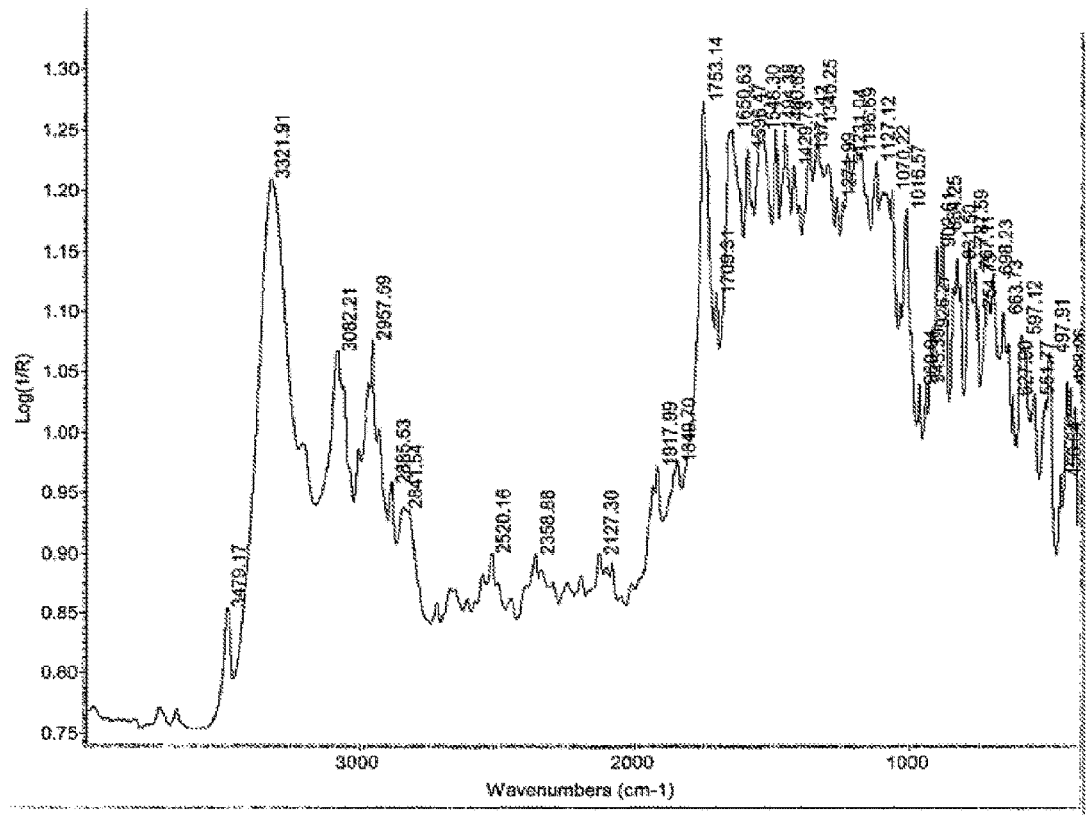

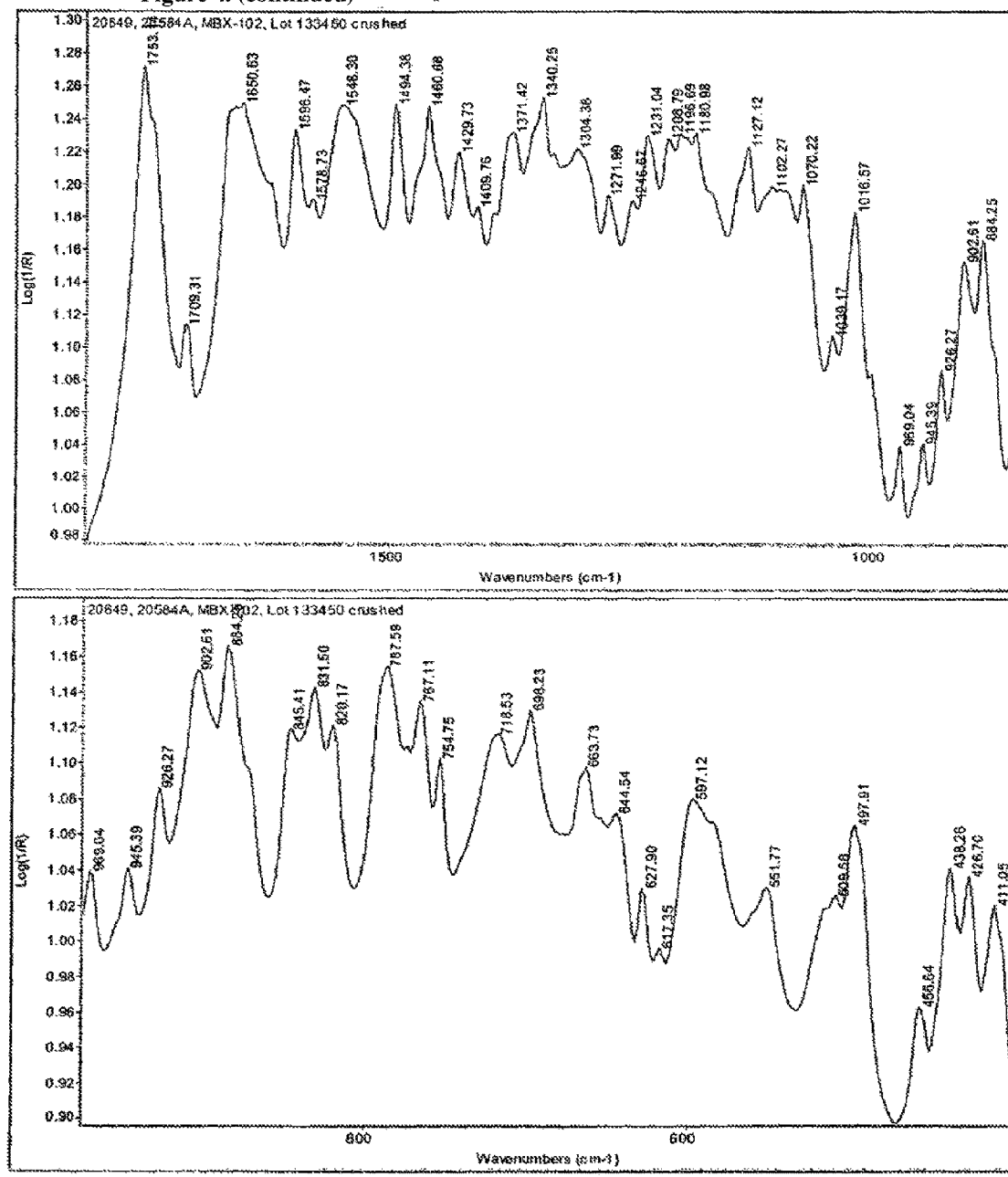
Figure 4. (continued) FT-IR Spectrum of Form A with Labeled Peaks

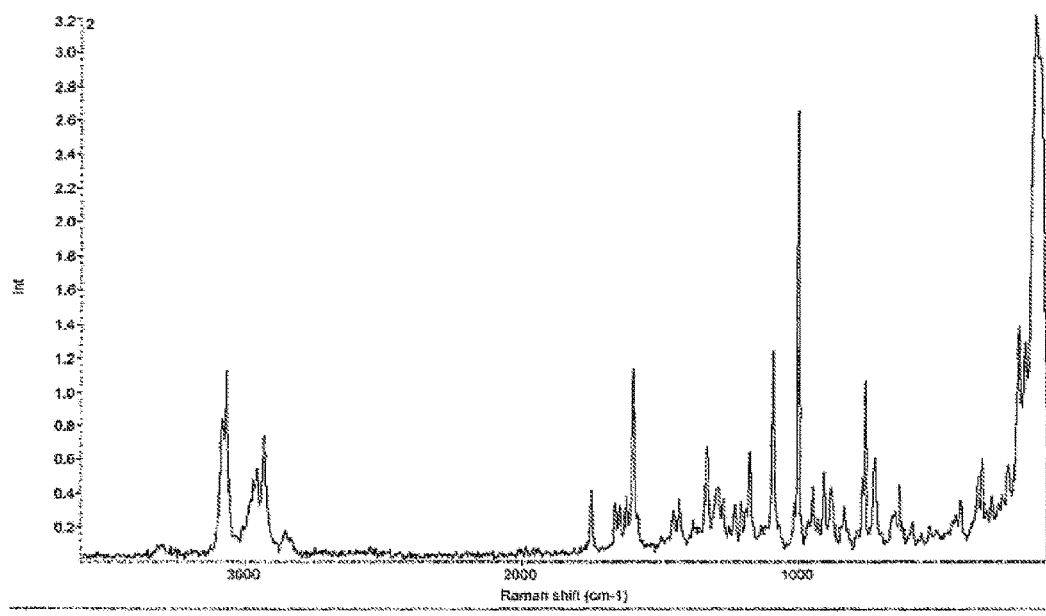
Figure 5. FT-Raman Spectrum of Form A

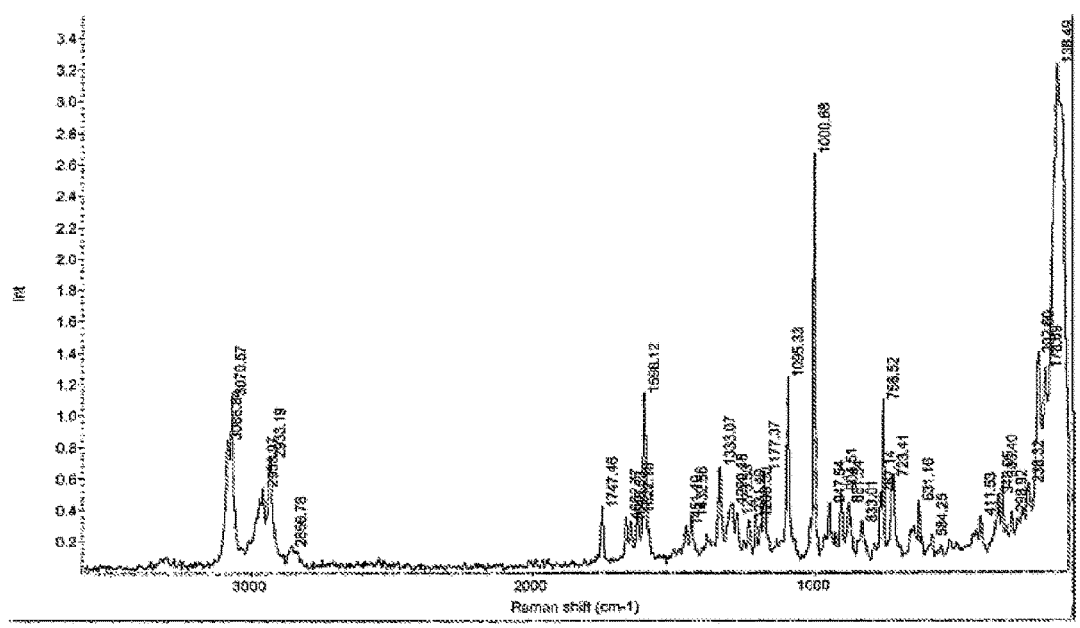
Figure 6. FT-Raman Spectrum of Form A with Labeled Peaks

FT-Raman Spectrum of Form A with Labeled Peaks

Figure 7. Cyclic DSC analysis of MBX-102 (Form A).
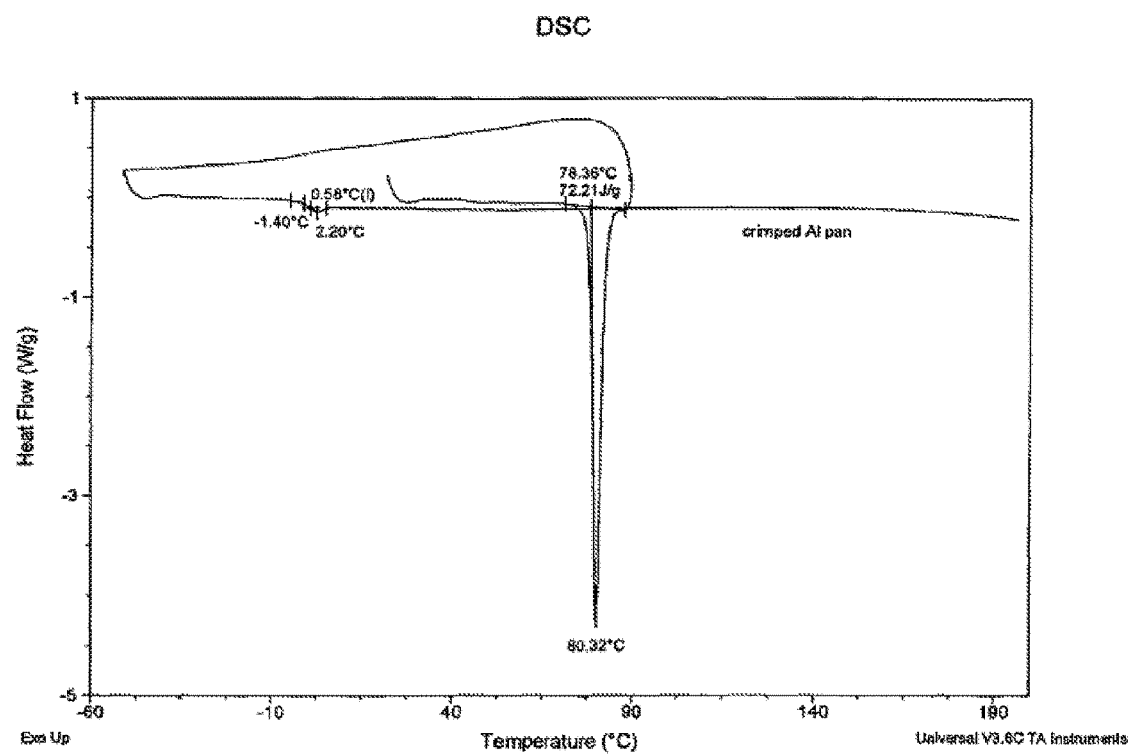

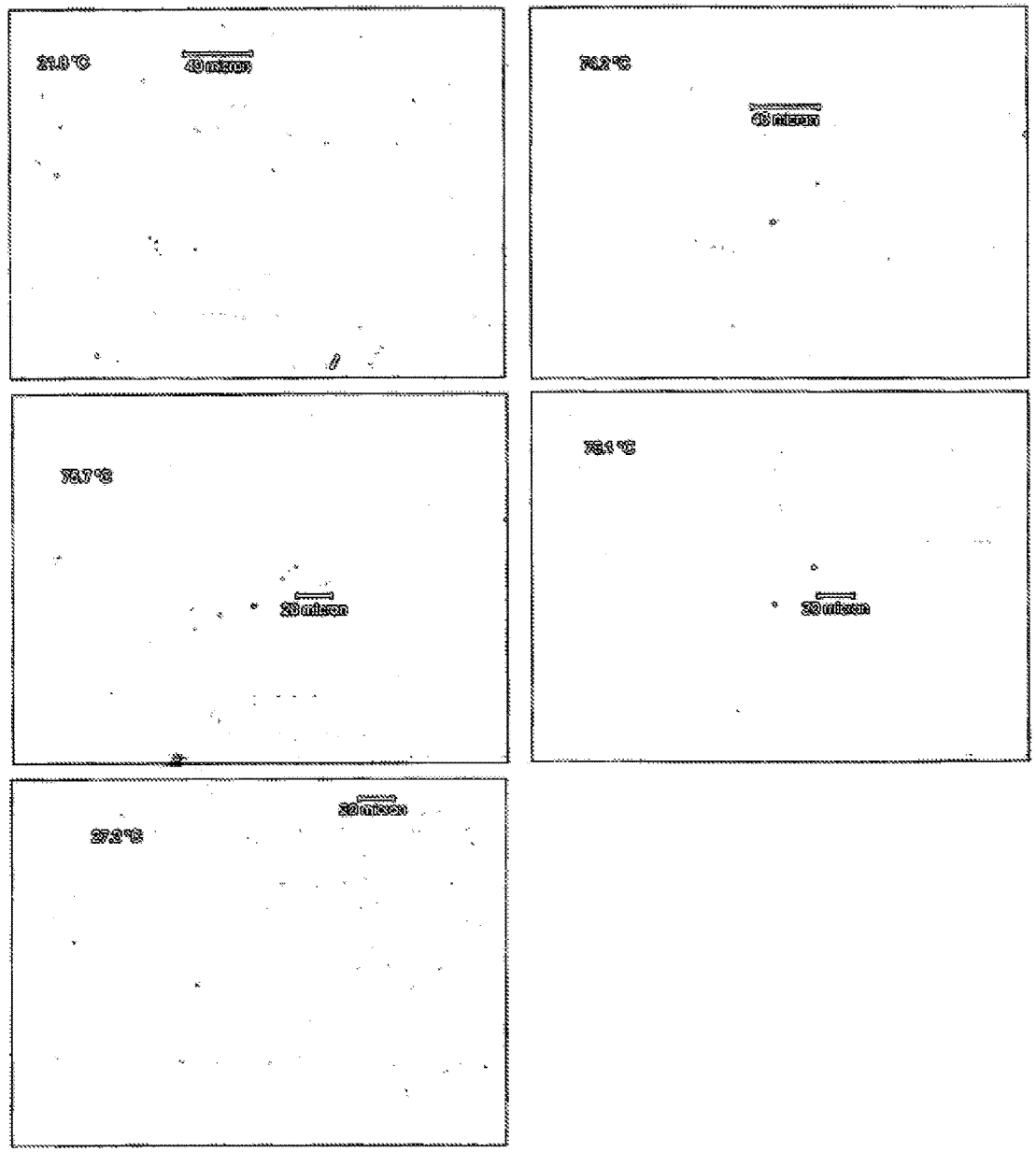
Figure 8. Hot stage microscopy of MBX-102 (Form A).

Figure 9. Microscopy of MBX-102 (Form A) after cyclic DSC.
material on outside of pan
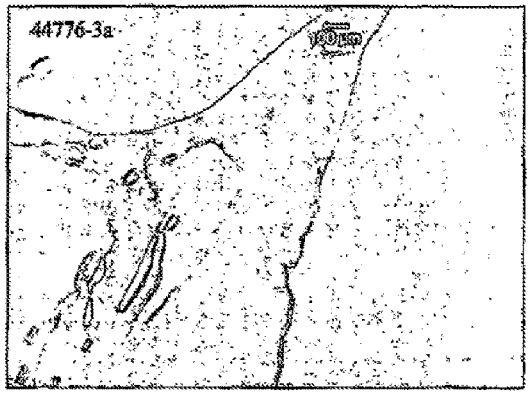
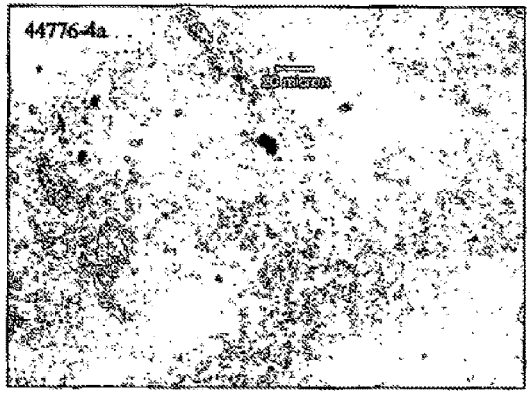
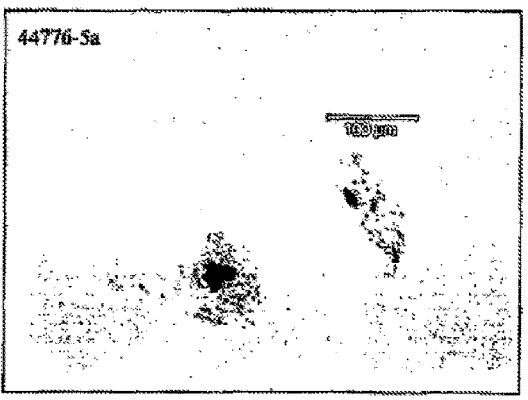
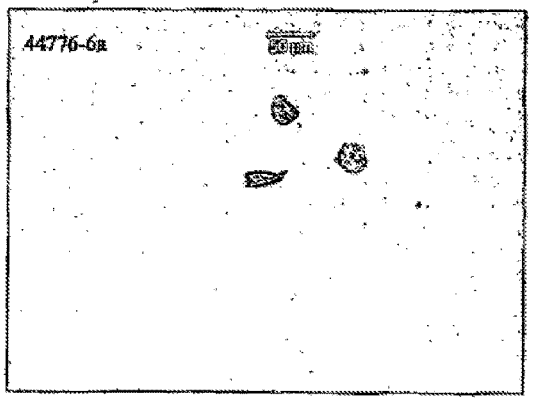
material from inside of pan

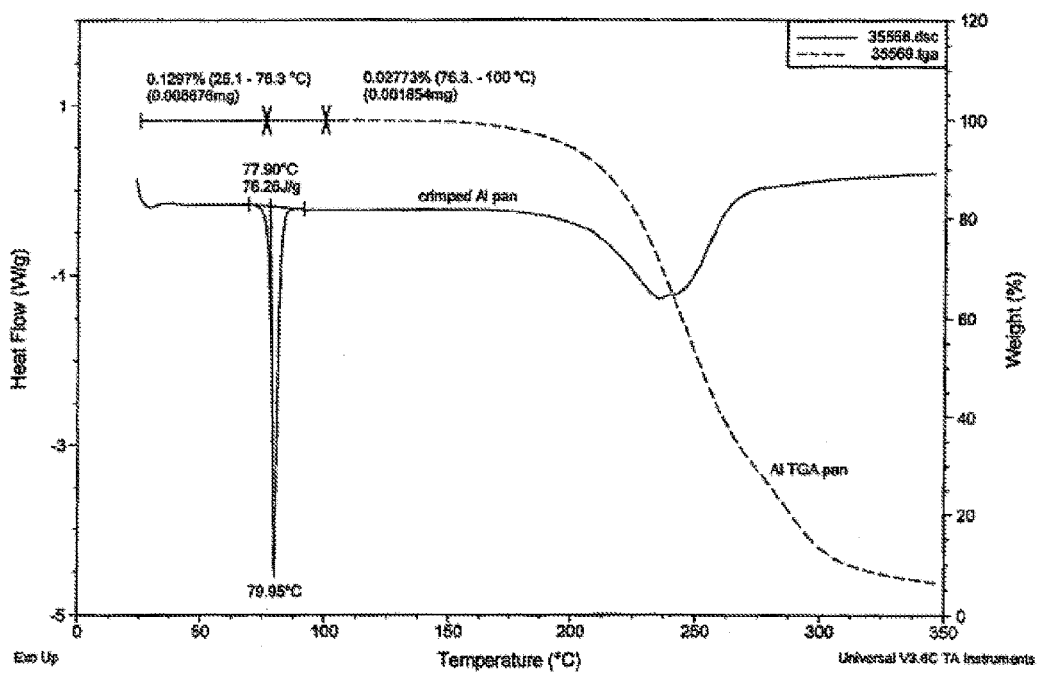
Figure 10. Thermal analysis of MBX-102 (Form A)

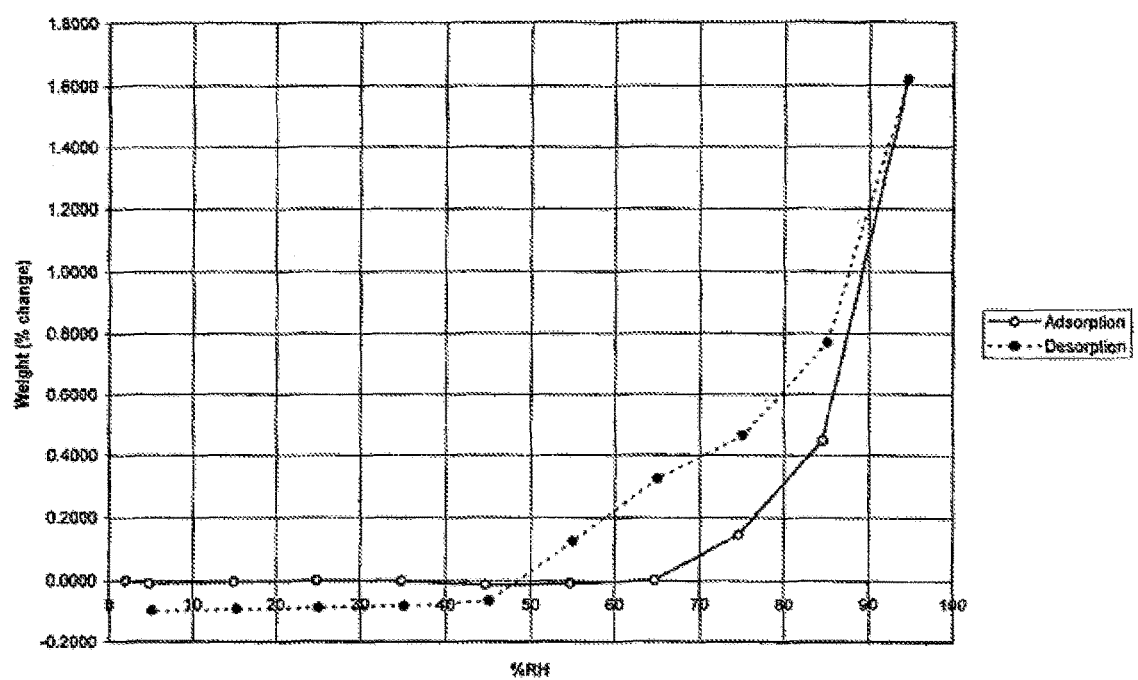
Figure 11. Automated moisture sorption/desorption of MBX-102, (Form A).

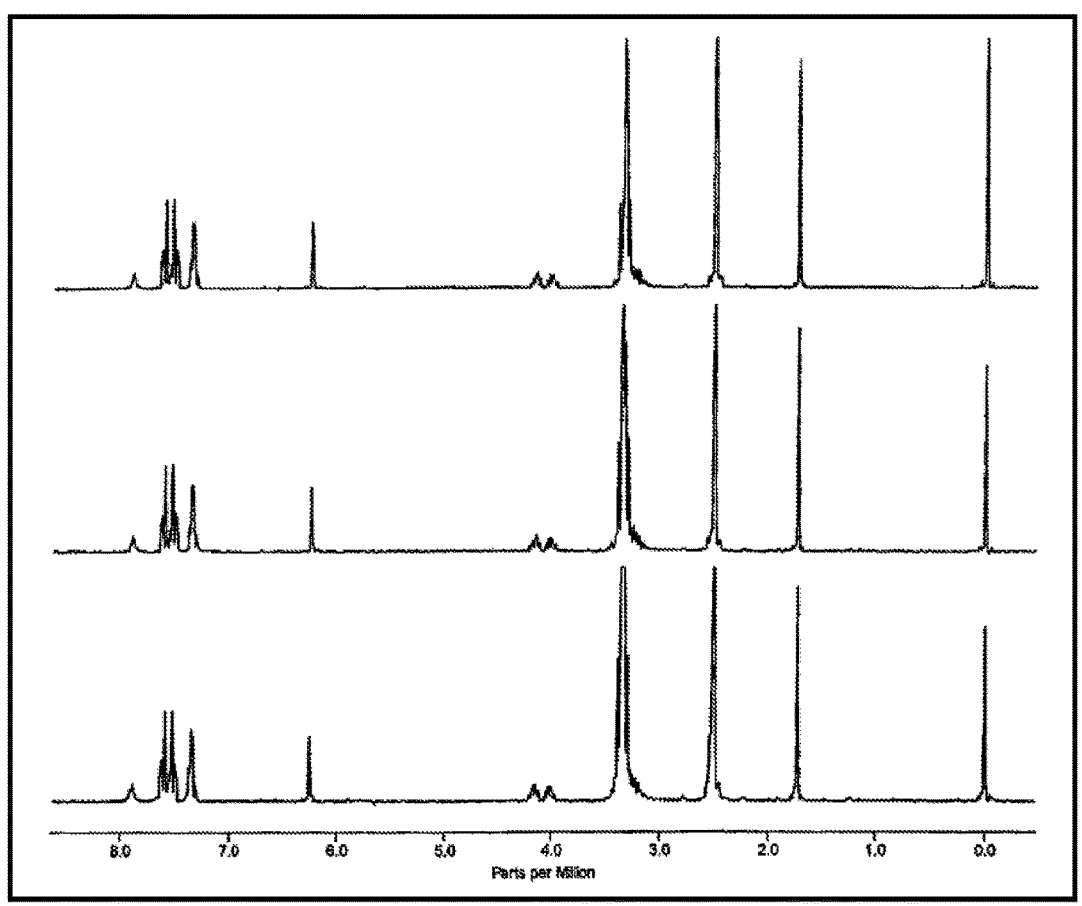
Figure 12. Proton NMR spectra for MBX-102 Form A, Form D, Form E (full spectra).
From top to bottom: A, D, and E.

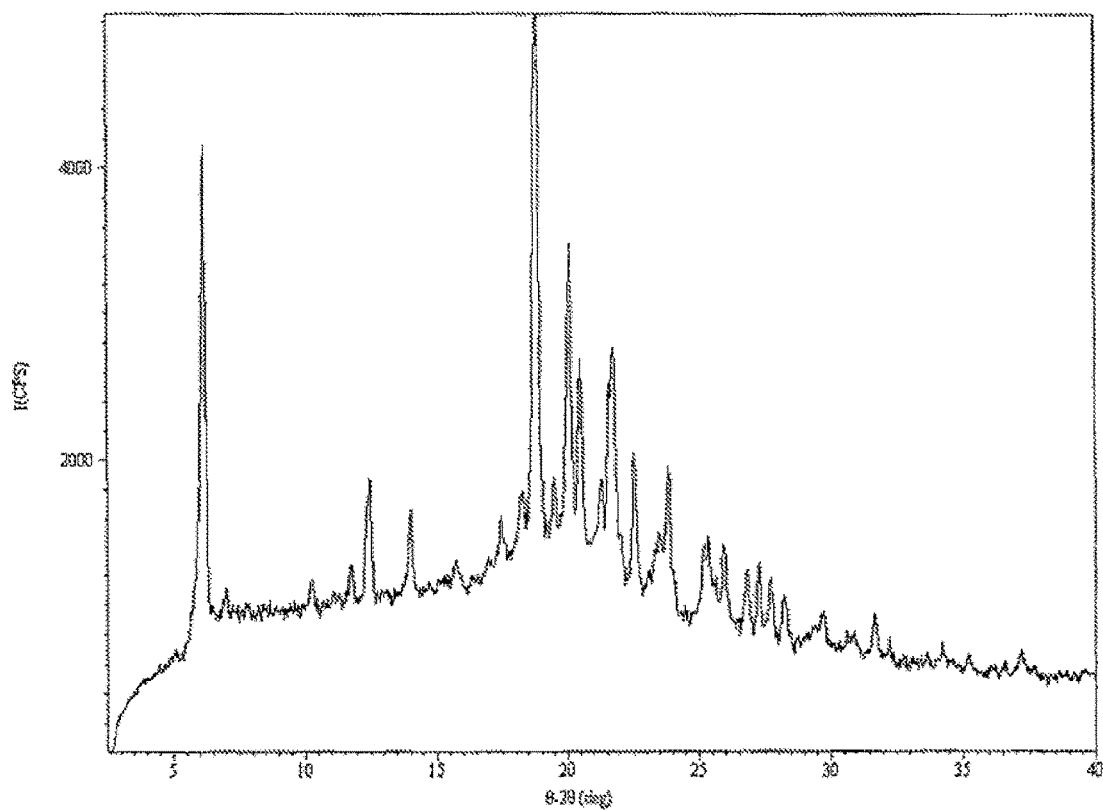
Figure 13. XRPD Pattern of Form B

Figure 14. XRPD Peak Listing for Form B
* Basic Data Process *

```
# Strongest 3 peaks
  no.   peak    2Theta        d         I/I1    FWHM      Intensity    Integrated Int
         no.    (deg)        (A)                (deg)     (Counts)     (Counts)
   1     22    18.7837     4.72039      100     0.28080    2544         37793
   2      9     6.1593    14.33806       81     0.24560    2072         27938
   3     24    20.0647     4.42182       51     0.25910    1304         18590

# Peak Data List
         peak   2Theta        d         I/I1    FWHM      Intensity    Integrated Int
          no.   (deg)        (A)                (deg)     (Counts)     (Counts)
           1     2.9017    30.42331       4     0.22000      95          2992
           2     3.3217    26.57743       5     0.00000     135             0
           3     3.7617    23.46964       6     0.00000     150             0
           4     4.1217    21.42051       5     0.00000     127             0
           5     4.4017    20.05852       5     0.00000     126             0
           6     4.8817    18.08726       5     0.00000     115             0
           7     5.0817    17.37584       5     0.00000     123             0
           8     5.7217    15.43362      10     0.34460     250          8850
           9     6.1593    14.33806      81     0.24560    2072         27938
          10     6.5617    13.45964       7     0.00000     170             0
          11     6.9617    12.68716       9     0.00000     224             0
          12     7.3217    12.06413       5     0.00000     129             0
          13     7.8017    11.32293       5     0.39200     124          3354
          14     8.4217    10.49068       3     1.12000      82          4507
          15    10.2411     8.63066       5     0.23890     123          1831
          16    11.7450     7.52870       6     0.22430     158          2392
          17    12.4245     7.11844      21     0.25350     533          7412
          18    14.0136     6.31460      12     0.21800     313          4128
          19    15.7417     5.62507       4     0.25340      98          1969
          20    17.4478     5.07868       8     0.28120     199          4423
          21    18.2217     4.86469      12     0.30480     315          6439
          22    18.7837     4.72039     100     0.28080    2544         37793
          23    19.4686     4.55585      13     0.27870     338          6794
          24    20.0647     4.42182      51     0.25910    1304         18590
          25    20.5003     4.32884      33     0.23360     828         11020
          26    21.2617     4.17551      15     0.26400     387          6638
          27    21.6833     4.09526      40     0.35040    1011         17170
          28    22.0617     4.02587       6     0.14340     151          1732
          29    22.5440     3.94082      21     0.21820     527          6034
          30    23.1017     3.84693       4     0.22000      94          1107
          31    23.5217     3.77918      12     0.48000     295          5761
          32    23.8172     3.73296      23     0.25890     588          6159
          33    24.0817     3.69255       4     0.11760      95           814
          34    25.2829     3.51978      13     0.43750     340          8286
          35    25.6217     3.47400       7     0.00000     166             0
          36    25.9457     3.43134      14     0.22510     344          5279
          37    26.7987     3.32403       9     0.21750     239          2805
          38    27.2442     3.27068      10     0.19240     262          2603
          39    27.7092     3.21684      10     0.21920     250          2933
          40    28.2401     3.15756       7     0.22600     183          2298
          41    29.3417     3.04147       3     0.20800      81          1313
          42    29.6634     3.00921       6     0.27010     154          2180
          43    31.6671     2.82323       7     0.21350     180          2303
          44    34.2199     2.61823       4     0.21360      97          1987
          45    37.1571     2.41773       4     0.23080     113          2119
          46    40.8093     2.20939       4     0.19970     101          1479
```

(-)-Halofenate, Form B. [Form B → Form A transition is implied.]
DSC

Figure 16. XRPD pattern for Form C.

(-)-Halofenate, Form C. [Form C → Form A transition is implied.]
DSC

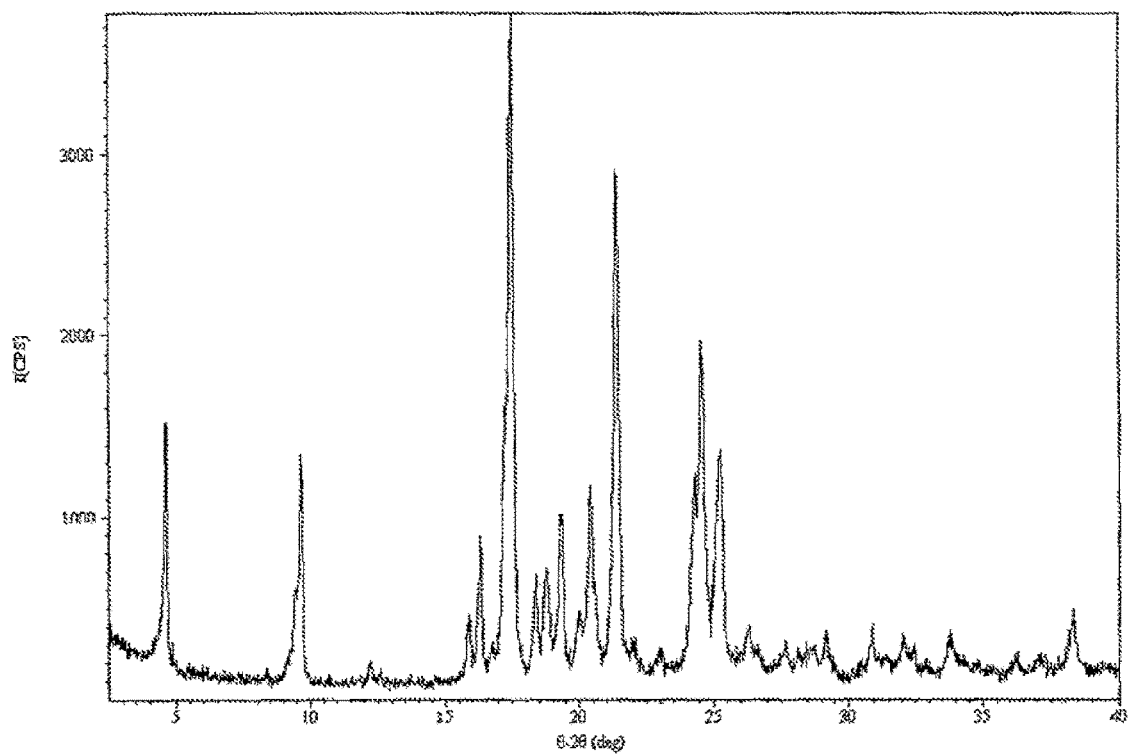
Figure 18. XRPD Pattern for Form D

Figure 19. XRPD Peak Listing for Form D

\*\*\* Basic Data Process \*\*\*

```
# Strongest 3 peaks
   no.   peak    2Theta        d        I/I1     FWHM      Intensity    Integrated Int
         no.     (deg)        (A)                (deg)     (Counts)     (Counts)
    1     10     17.4451     5.07946    100      0.20790     944         10169
    2     19     21.3646     4.15563     76      0.21220     719          7813
    3     25     24.5209     3.62740     51      0.24180     477          5688

# Peak Data List
         peak    2Theta        d        I/I1     FWHM      Intensity    Integrated Int
         no.     (deg)        (A)                (deg)     (Counts)     (Counts)
           1     4.2000     21.02134      3      0.21340      30           664
           2     4.5883     19.24318     34      0.15160     324          2863
           3     9.4000      9.40095     12      0.17340     116          1439
           4     9.6243      9.18235     31      0.18120     293          2723
           5    12.1975      7.25040      3      0.16500      29           401
           6    15.8647      5.58173      8      0.19850      78           842
           7    16.2788      5.44066     18      0.18570     168          1593
           8    16.7138      5.30003      3      0.15640      30           304
           9    17.1600      5.16321     28      0.14980     269          3095
          10    17.4451      5.07946    100      0.20790     944         10169
          11    17.7600      4.99010      3      0.09000      28           387
          12    18.3384      4.83400     12      0.19350     116          1153
          13    18.7413      4.73097     14      0.25330     135          1862
          14    19.2981      4.59571     23      0.20370     216          2406
          15    20.0000      4.43598      7      0.23340      68           943
          16    20.4035      4.34916     27      0.22180     252          2727
          17    20.6400      4.29985      7      0.12400      62           656
          18    21.1000      4.20714      9      0.13500      82           936
          19    21.3646      4.15563     76      0.21220     719          7813
          20    21.7400      4.08471      3      0.20000      29           456
          21    21.9863      4.03951      4      0.26070      37           514
          22    22.9840      3.86636      3      0.20800      30           411
          23    23.9400      3.71409      4      0.11640      35           259
          24    24.2600      3.66582     29      0.26760     271          3446
          25    24.5209      3.62740     51      0.24180     477          5688
          26    25.1736      3.53481     34      0.31170     317          5551
          27    26.2590      3.39111      6      0.23800      56          1069
          28    27.6333      3.22550      4      0.18670      37           547
          29    28.4200      3.13798      3      0.11340      30           312
          30    28.6200      3.11650      3      0.35200      33           546
          31    29.1487      3.06117      6      0.17750      55           700
          32    30.8607      2.89514      7      0.20140      63          1014
          33    32.0229      2.79267      5      0.21590      47           768
          34    32.4187      2.75947      3      0.11750      30           233
          35    33.7956      2.65005      5      0.27330      50          1020
          36    36.2366      2.47701      3      0.15330      29           385
          37    38.2664      2.35016      8      0.26280      79          1393
```

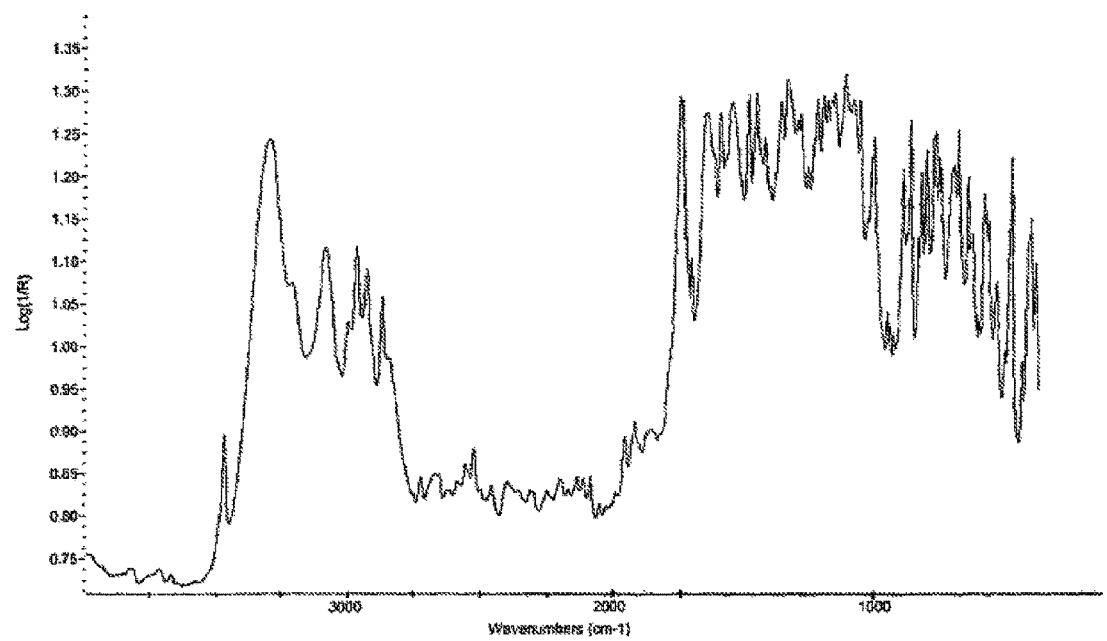
Figure 20 FT-IR Spectrum for Form D

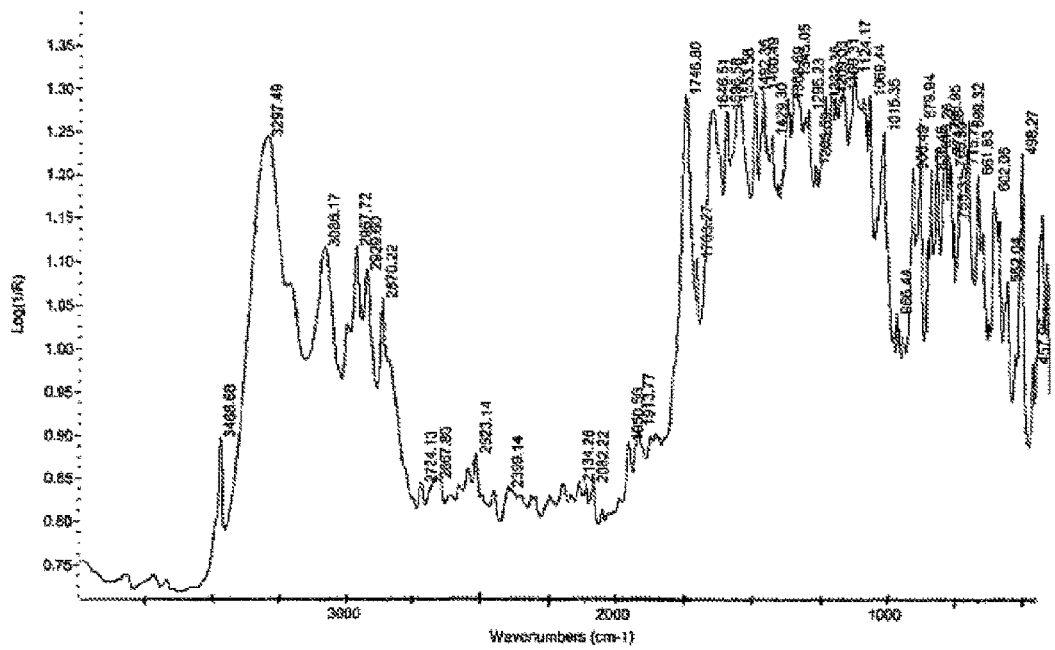
Figure 21. FT-IR Spectrum of Form D with Labeled Peaks

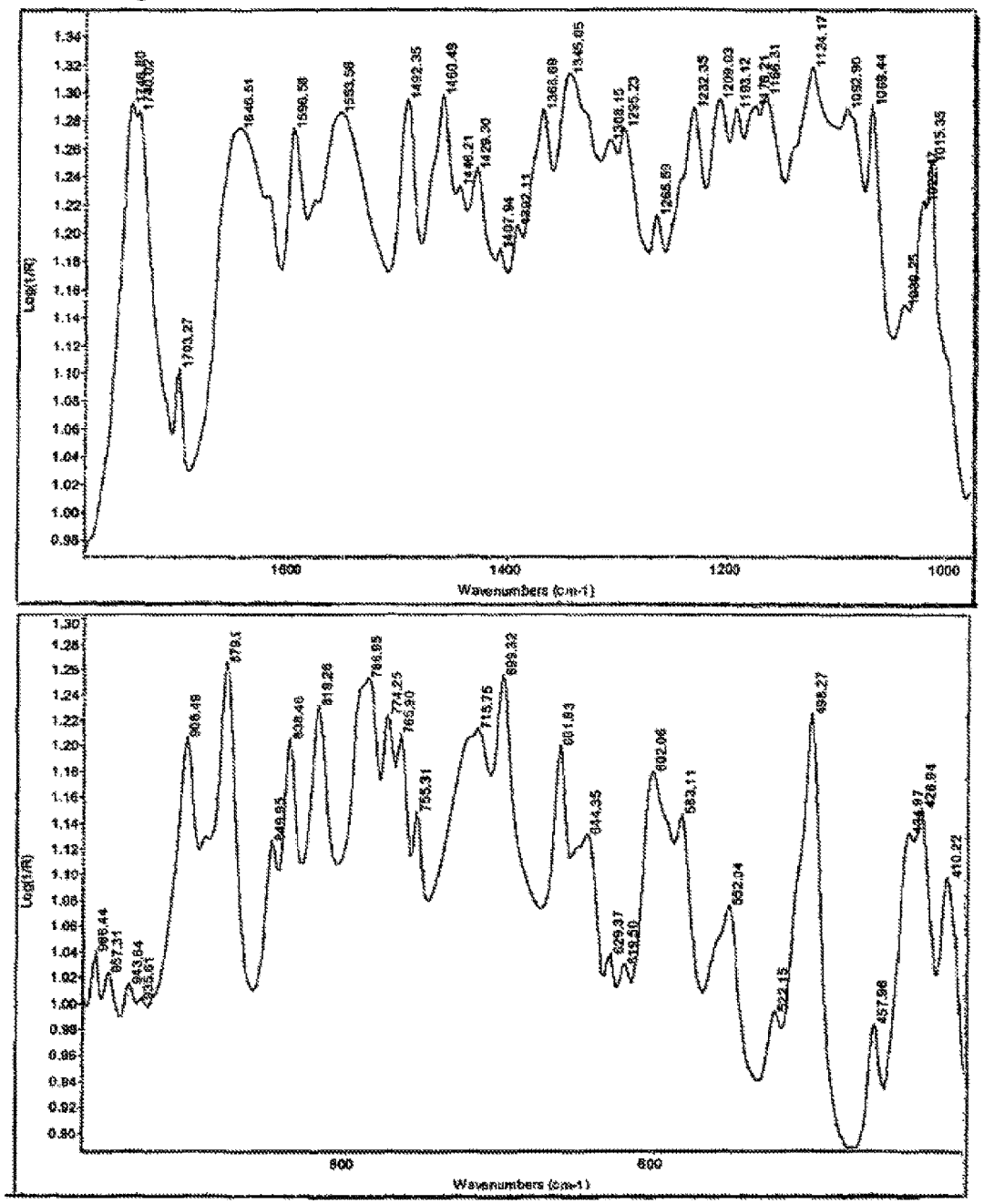
Figure 21. (continued) FT-IR Spectrum of Form D with Labeled Peaks

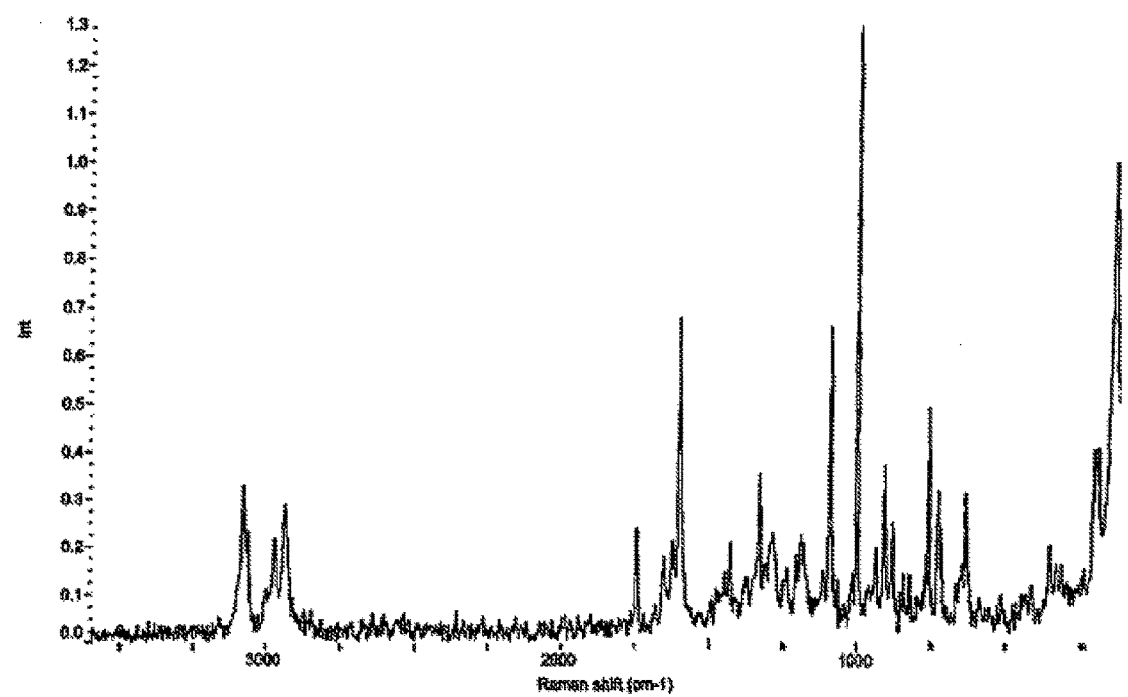
Figure 22. FT-Raman Spectrum of Form D

Figure 23. FT-Raman Spectrum of Form D with Labeled Peaks
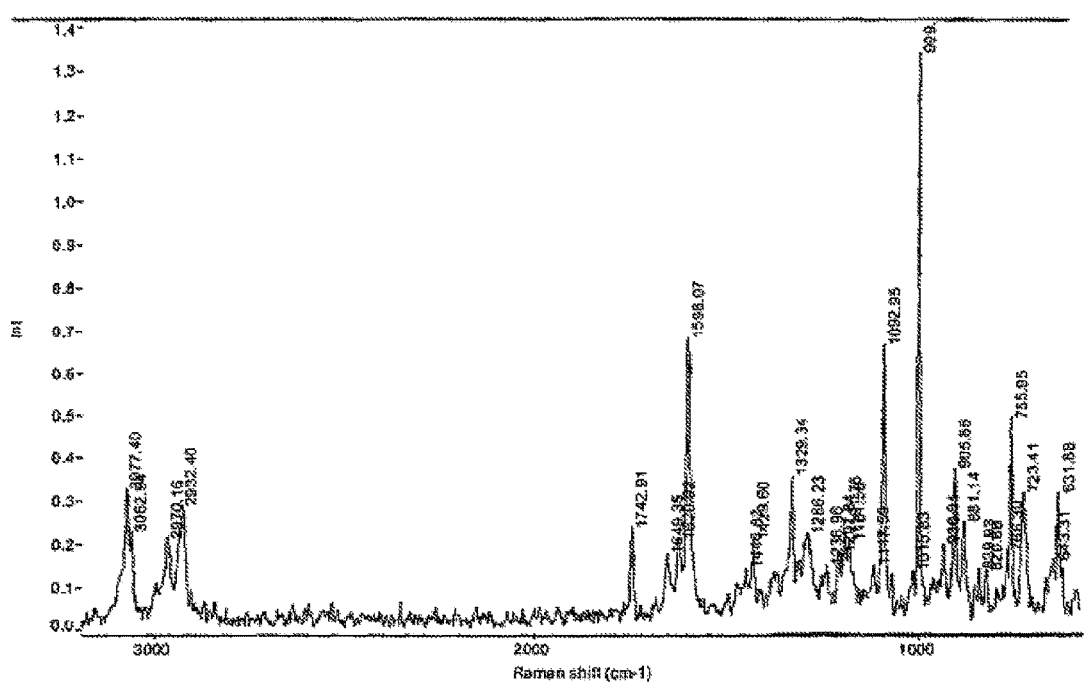

FT-Raman Spectrum of Form D with Labeled Peaks

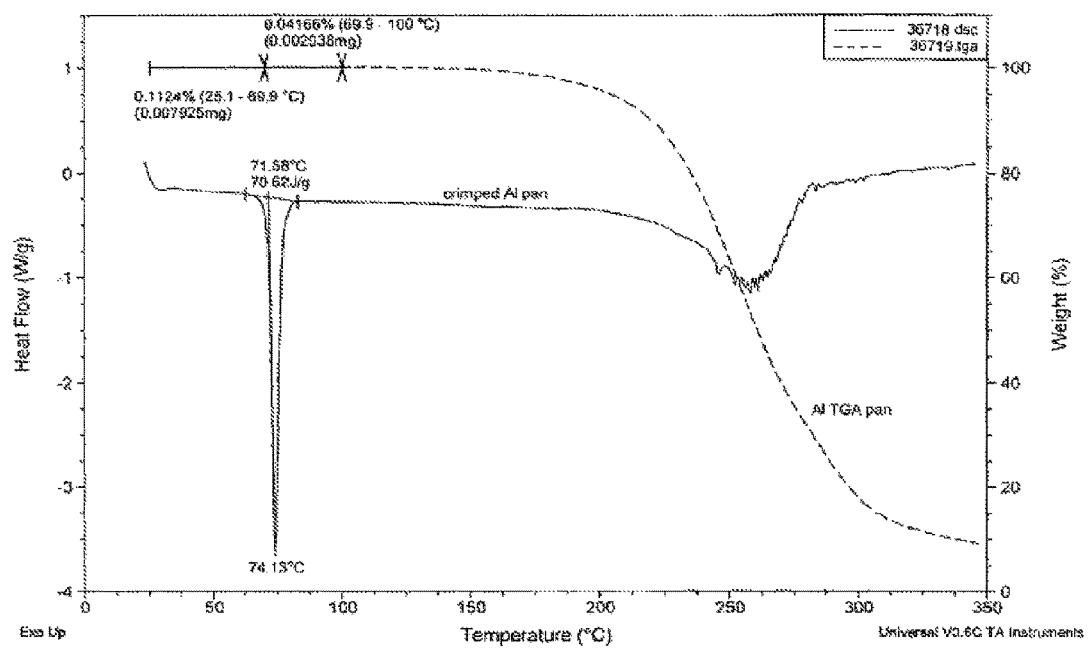
Figure 24. Thermal analysis of MBX-102 Form D

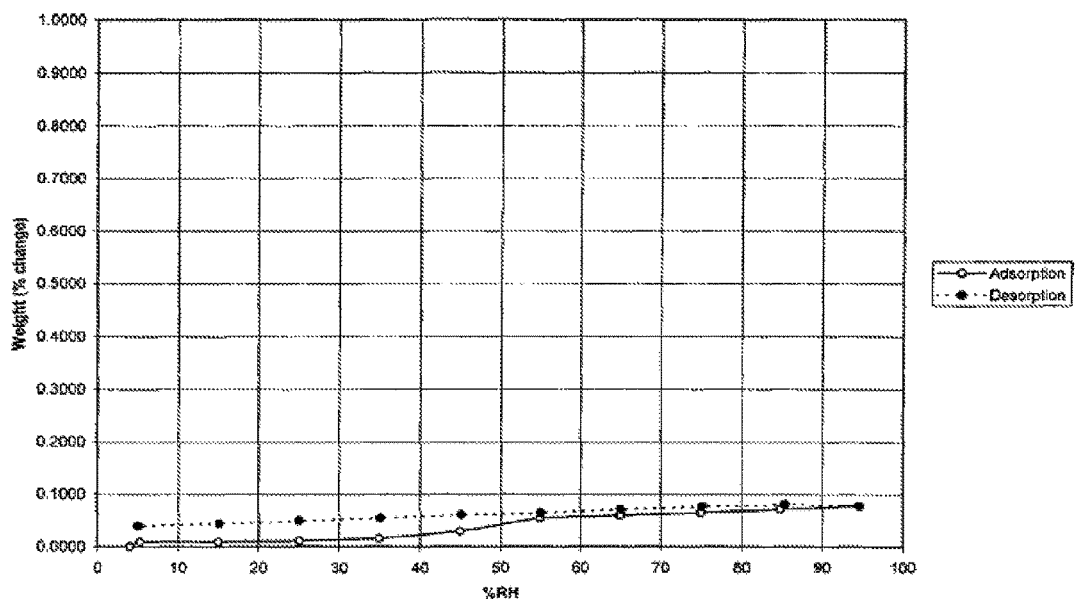
Figure 25. Automatic moisture sorption/desorption of MBX-102 Form D.

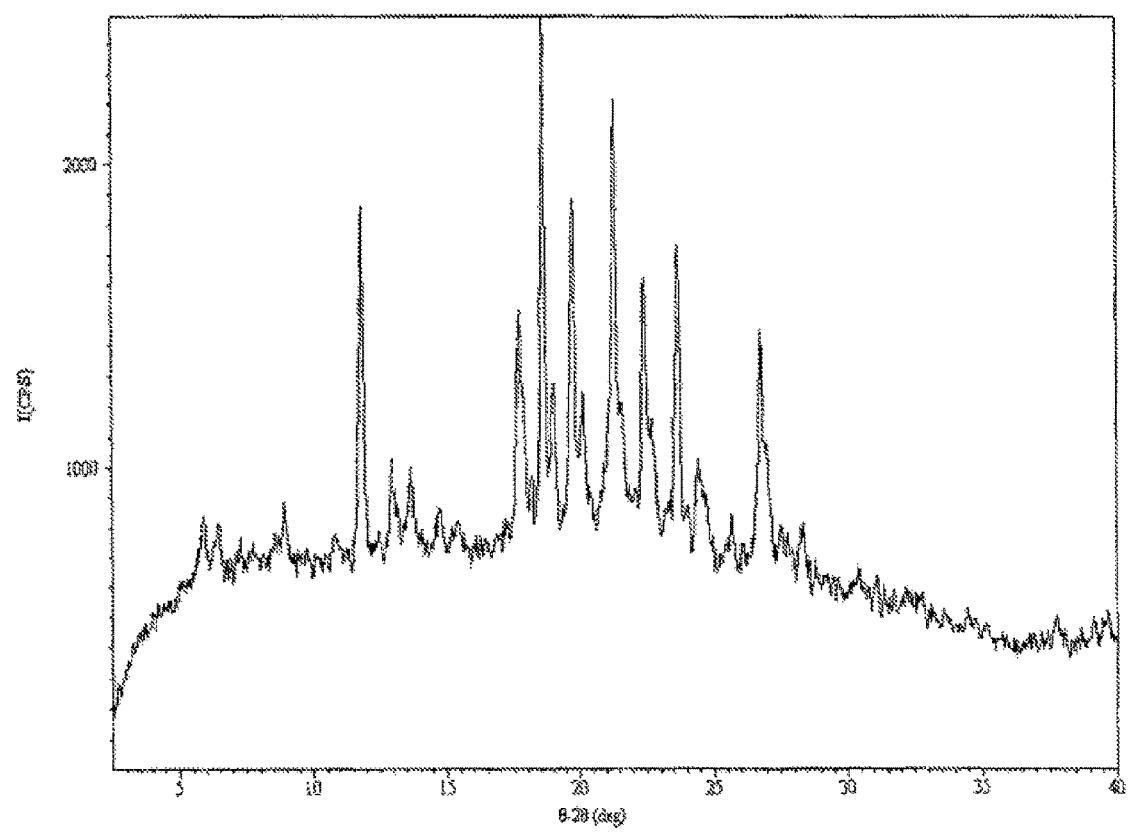
Figure 26. XRPD Pattern for Form E

Figure 27. XRPD Peak Listing for Form E

* Basic Data Process *

```
# Strongest 3 peaks
  no.  peak   2Theta      d         I/I1   FWHM     Intensity    Integrated Int
       no.    (deg)       (A)              (deg)    (Counts)     (Counts)
  1    42     18.5910     4.76888   100    0.18460  1058         10319
  2    49     21.2800     4.17196   85     0.20920  896          8522
  3    28     11.7974     7.49538   70     0.19900  741          7941

# Peak Data List
       peak   2Theta      d         I/I1   FWHM     Intensity    Integrated Int
       no.    (deg)       (A)              (deg)    (Counts)     (Counts)
       1      2.5078      35.20094  6      0.13200  59           990
       2      2.7078      32.60141  9      0.00000  92           0
       3      2.9878      29.54678  9      0.00000  97           0
       4      3.2478      27.18200  11     0.00000  117          0
       5      3.4478      25.60566  12     0.00000  123          0
       6      3.6878      23.93978  10     0.00000  111          0
       7      3.9478      22.36368  10     0.00000  110          0
       8      4.1878      21.08256  10     0.00000  106          0
       9      4.4078      20.03077  9      0.00000  92           0
       10     4.5878      19.24527  8      0.00000  81           0
       11     5.0078      17.63209  9      0.00000  92           0
       12     5.3078      16.63617  7      0.00000  79           0
       13     5.6278      15.69092  10     0.00000  109          0
       14     5.8678      15.04967  17     0.28800  184          3765
       15     6.2478      14.13516  9      0.00000  100          0
       16     6.4278      13.73972  14     0.25400  148          2344
       17     6.7278      13.12771  4      0.00000  44           0
       18     6.8878      12.82312  3      0.16000  34           424
       19     7.2149      12.24247  7      0.28290  76           1297
       20     7.6078      11.61108  4      0.00000  43           0
       21     7.7878      11.34311  5      0.30000  48           749
       22     8.0611      10.95914  3      0.17330  37           332
       23     8.5478      10.33620  6      0.31000  67           1182
       24     8.9402      9.88339   12     0.24630  125          1838
       25     10.8506     8.14719   6      0.35430  67           1438
       26     11.2878     7.83260   3      0.11000  36           268
       27     11.5478     7.65682   5      0.09340  48           379
       28     11.7974     7.49538   70     0.19900  741          7941
       29     12.4189     7.12164   4      0.22220  47           788
       30     12.9678     6.82140   17     0.23520  175          1926
       31     13.1678     6.71824   9      0.14940  91           1138
       32     13.4078     6.59852   6      0.00000  64           0
       33     13.6435     6.48505   17     0.26700  175          2631
       34     14.0478     6.29930   4      0.14000  47           575
       35     14.6959     6.02293   10     0.27910  105          1628
       36     15.1278     5.85193   4      0.15500  41           391
       37     15.4078     5.74621   8      0.23420  80           1332
       38     16.0244     5.52646   3      0.12670  37           550
       39     17.1983     5.15180   3      0.16760  36           498
       40     17.7328     4.99770   43     0.32040  459          7097
       41     18.1249     4.89045   12     0.17830  126          1328
       42     18.5910     4.76888   100    0.18460  1058         10319
       43     18.9695     4.67457   29     0.22870  307          3855
       44     19.7157     4.49930   65     0.21070  690          7704
       45     20.0779     4.41895   24     0.26910  255          3553
       46     20.3878     4.35247   5      0.11380  48           363
       47     20.7678     4.27368   4      0.10720  42           308
```

Figure 27. (continued) XRPD Peak Listing for Form E

| peak no. | 2Theta (deg) | d (A) | I/I1 | FWHM (deg) | Intensity (Counts) | Integrated Int (Counts) |
|---|---|---|---|---|---|---|
| 48 | 21.0078 | 4.22540 | 17 | 0.22860 | 177 | 2612 |
| 49 | 21.2800 | 4.17196 | 85 | 0.20920 | 896 | 8522 |
| 50 | 21.5478 | 4.12071 | 24 | 0.22860 | 251 | 3535 |
| 51 | 22.0746 | 4.02355 | 6 | 0.16920 | 67 | 825 |
| 52 | 22.3836 | 3.96870 | 50 | 0.20140 | 525 | 4697 |
| 53 | 22.6478 | 3.92299 | 20 | 0.33340 | 208 | 3768 |
| 54 | 23.1478 | 3.83937 | 4 | 0.09060 | 47 | 392 |
| 55 | 23.6191 | 3.76382 | 59 | 0.20200 | 629 | 6916 |
| 56 | 23.9816 | 3.70774 | 7 | 0.24100 | 78 | 1036 |
| 57 | 24.3878 | 3.64690 | 17 | 0.21420 | 181 | 2307 |
| 58 | 24.7078 | 3.60038 | 11 | 0.18600 | 120 | 1565 |
| 59 | 24.8878 | 3.57475 | 4 | 0.08000 | 39 | 226 |
| 60 | 25.4278 | 3.50005 | 4 | 0.09840 | 45 | 240 |
| 61 | 25.6324 | 3.47257 | 8 | 0.17430 | 89 | 824 |
| 62 | 26.0744 | 3.41470 | 5 | 0.09330 | 49 | 254 |
| 63 | 26.4678 | 3.36483 | 7 | 0.10220 | 74 | 520 |
| 64 | 26.8012 | 3.32372 | 44 | 0.36080 | 464 | 5891 |
| 65 | 27.0278 | 3.29637 | 18 | 0.24800 | 187 | 2423 |
| 66 | 27.4947 | 3.24144 | 9 | 0.17020 | 94 | 866 |
| 67 | 27.7478 | 3.21245 | 6 | 0.17240 | 60 | 505 |
| 68 | 27.9078 | 3.19440 | 3 | 0.12000 | 33 | 212 |
| 69 | 28.2668 | 3.15464 | 9 | 0.23800 | 99 | 1353 |
| 70 | 30.3778 | 2.94005 | 7 | 0.18000 | 71 | 1043 |
| 71 | 31.0642 | 2.87663 | 6 | 0.16890 | 66 | 791 |
| 72 | 32.1278 | 2.78379 | 4 | 0.20000 | 44 | 707 |
| 73 | 32.3278 | 2.76702 | 3 | 0.10860 | 35 | 205 |
| 74 | 32.6710 | 2.73873 | 4 | 0.30150 | 47 | 861 |
| 75 | 33.5632 | 2.66794 | 4 | 0.12920 | 41 | 397 |
| 76 | 34.4338 | 2.60245 | 5 | 0.18800 | 54 | 631 |
| 77 | 34.6948 | 2.58347 | 3 | 0.17400 | 37 | 320 |
| 78 | 35.1000 | 2.55457 | 3 | 0.24050 | 37 | 567 |
| 79 | 37.7065 | 2.38376 | 6 | 0.27250 | 61 | 1224 |
| 80 | 39.1250 | 2.30054 | 7 | 0.16550 | 74 | 812 |
| 81 | 39.4278 | 2.28356 | 7 | 0.14800 | 69 | 553 |
| 82 | 39.6478 | 2.27140 | 9 | 0.17500 | 94 | 846 |
| 83 | 39.8928 | 2.25801 | 4 | 0.15000 | 40 | 590 |
| 84 | 42.7893 | 2.11163 | 7 | 0.14160 | 69 | 565 |
| 85 | 43.6146 | 2.07356 | 3 | 0.12360 | 33 | 423 |
| 86 | 44.8604 | 2.01883 | 3 | 0.12750 | 37 | 383 |
| 87 | 45.8628 | 1.97701 | 5 | 0.17000 | 48 | 897 |
| 88 | 47.2392 | 1.92257 | 4 | 0.15430 | 40 | 684 |
| 89 | 49.2328 | 1.84928 | 4 | 0.15000 | 46 | 614 |
| 90 | 103.6211 | 0.98006 | 3 | 0.17330 | 37 | 509 |

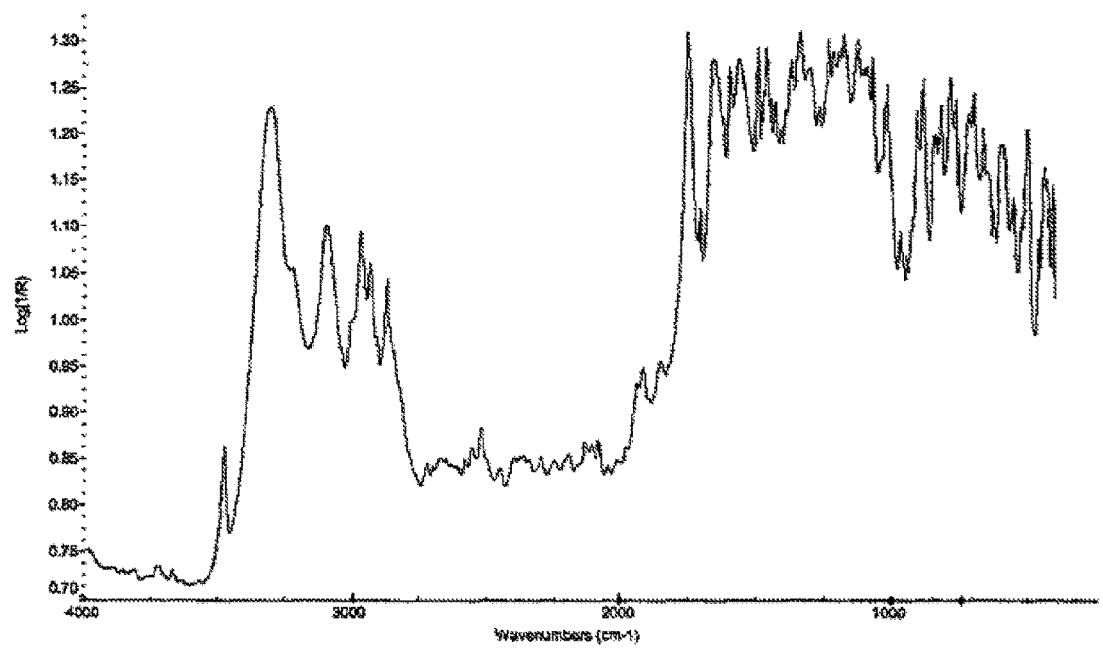
Figure 28. FT-IR Spectrum for Form E

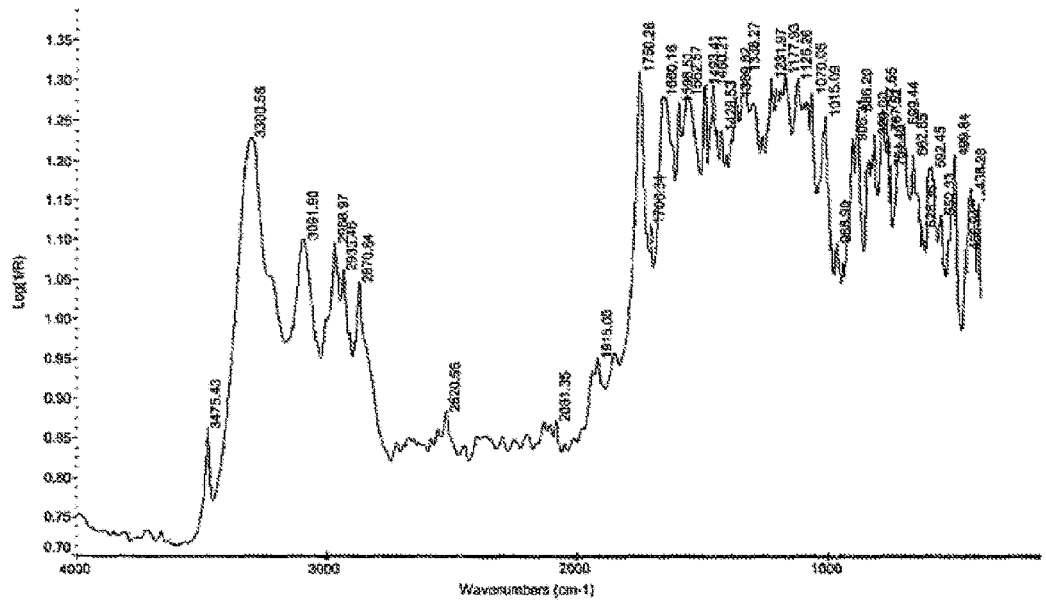
Figure 29. FT-IR Spectrum of Form E with Labeled Peaks

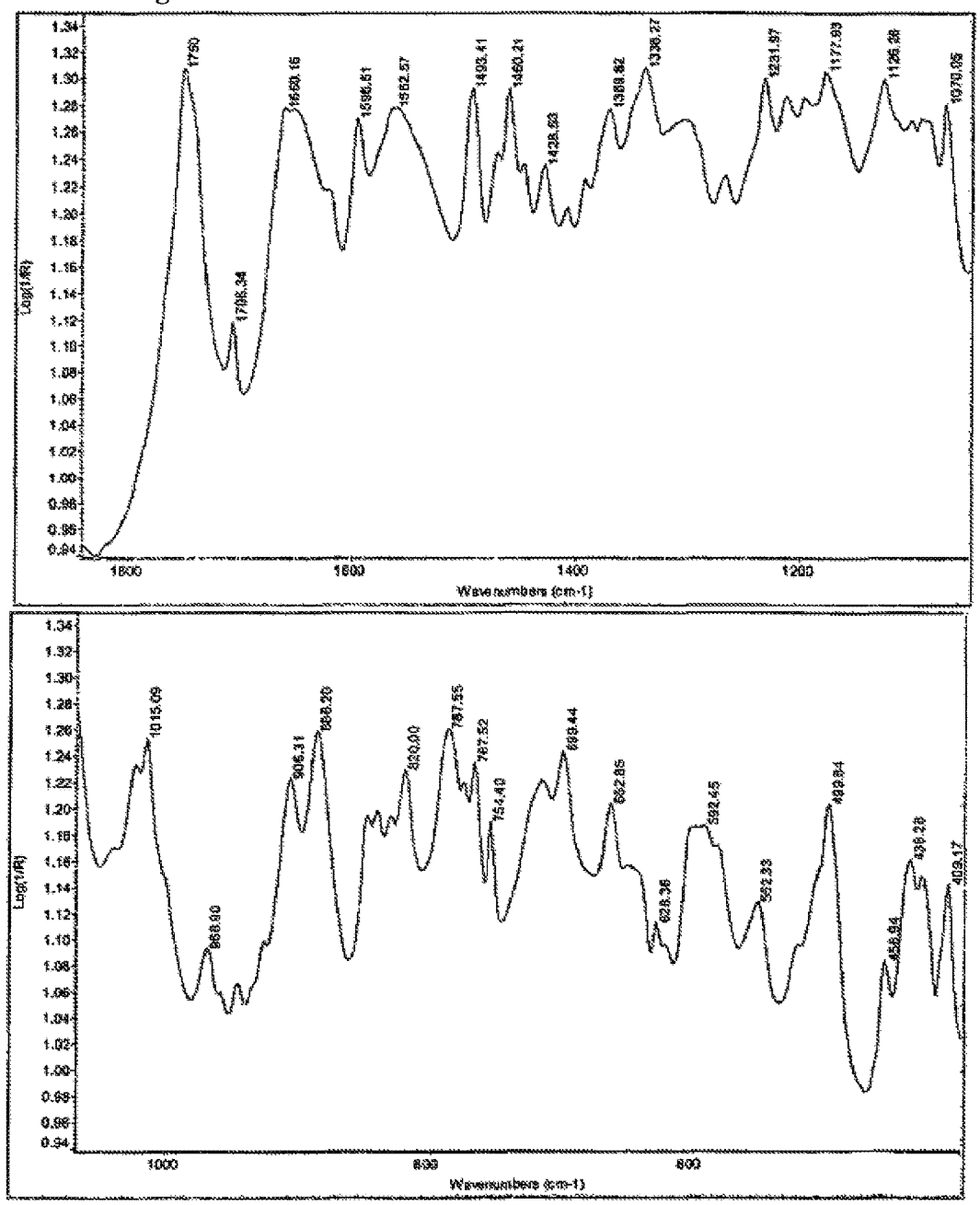
Figure 29. continued FT-IR Spectrum of Form E with Labeled Peaks

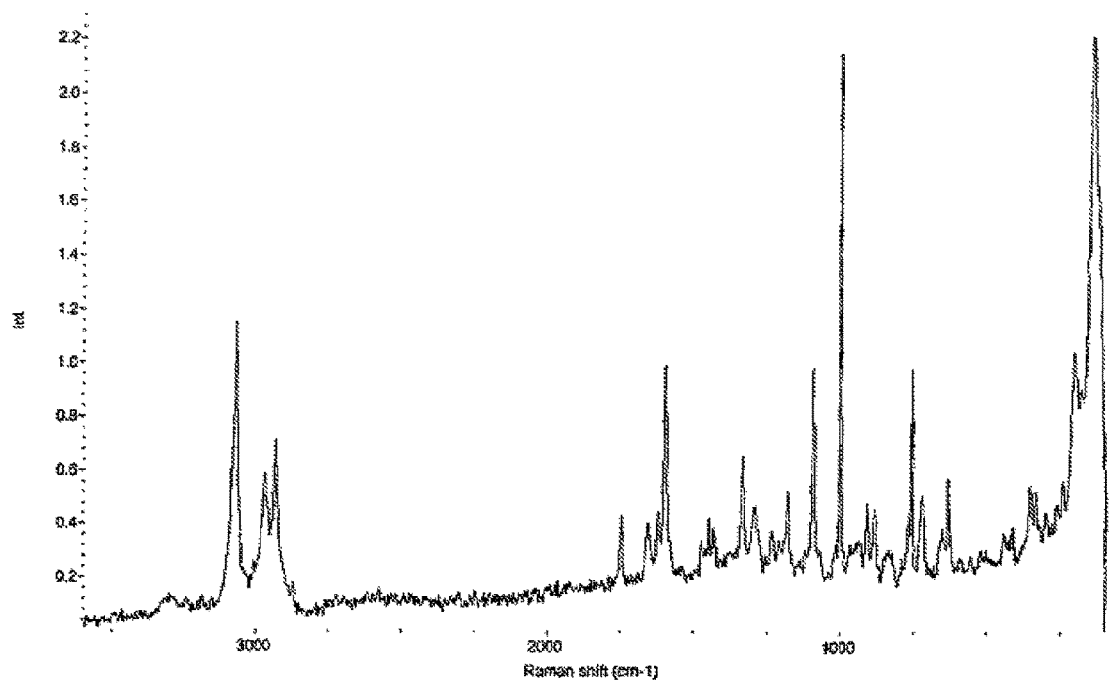
Figure 30. FT-Raman Spectrum of Form E

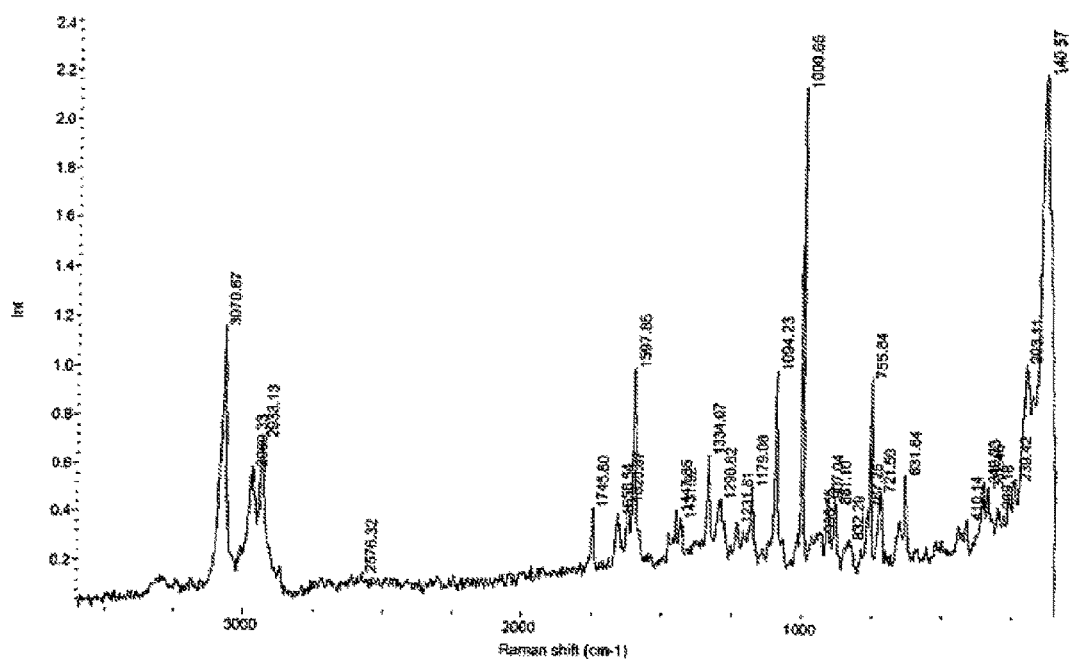
Figure 31. FT-Raman Spectrum of Form E with Labeled Peaks

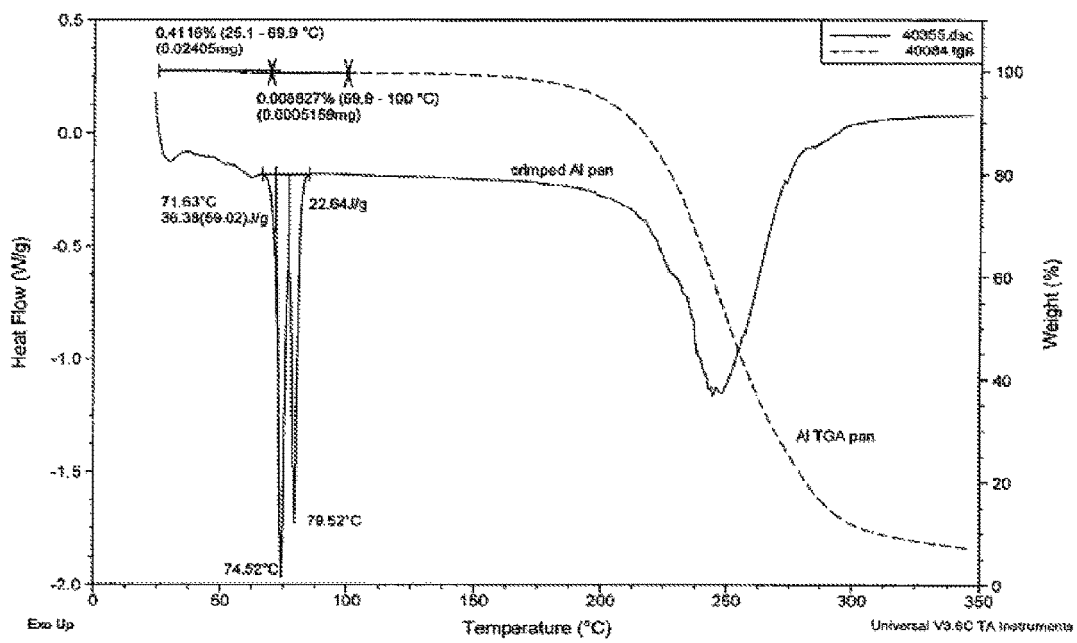
Figure 32. Thermal analysis of MBX-102 Form E

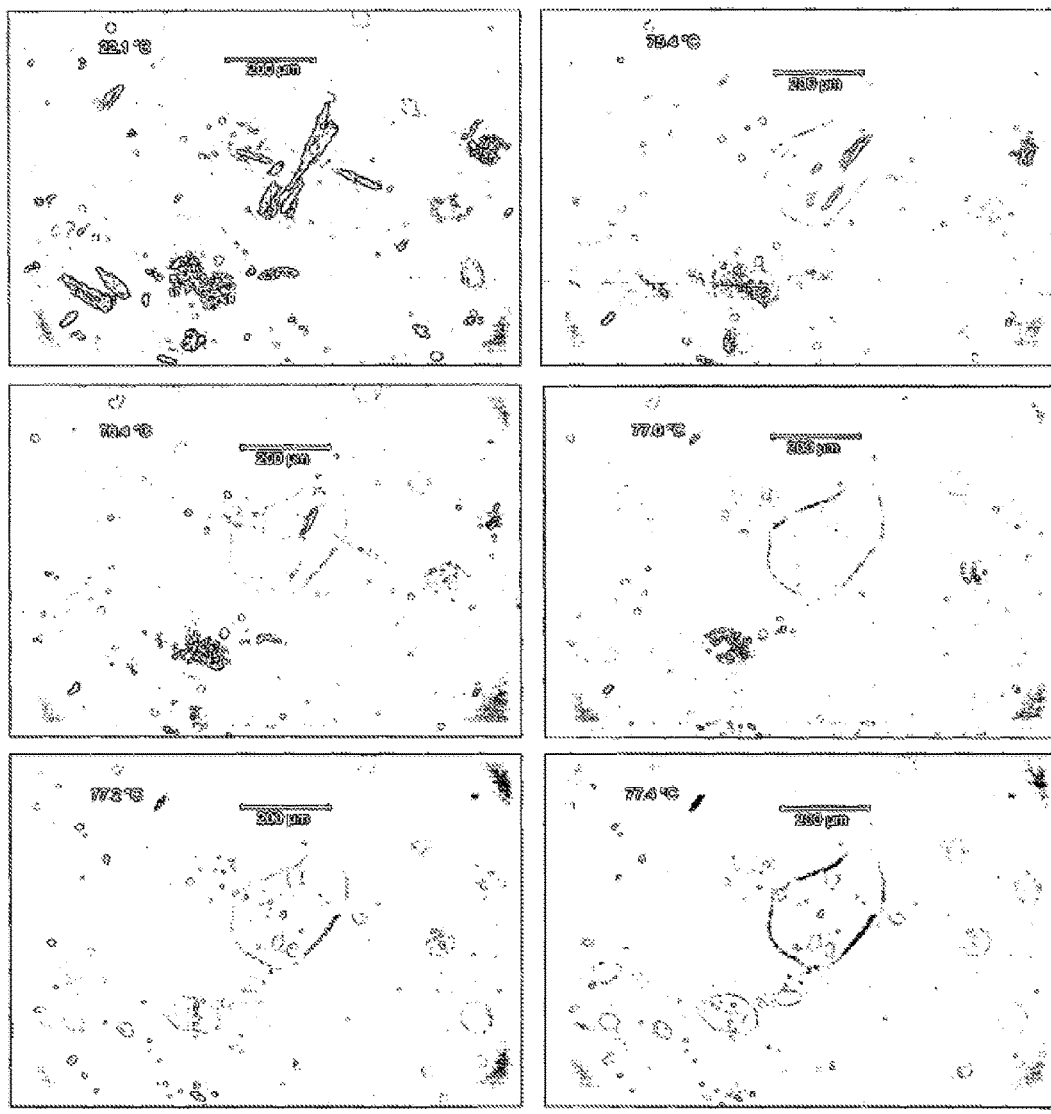
Figure 33. Hot stage microscopy of MBX-102 Form E

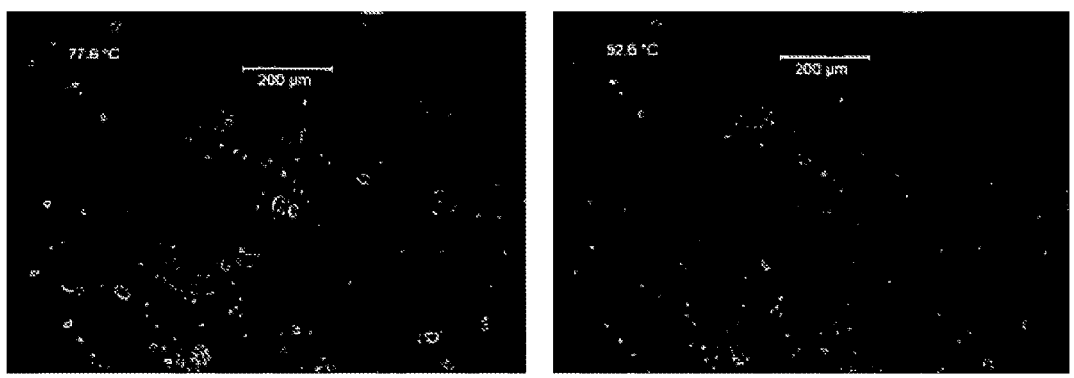
Figure 33.(continued) Hot stage microscopy of MBX-102 Form E

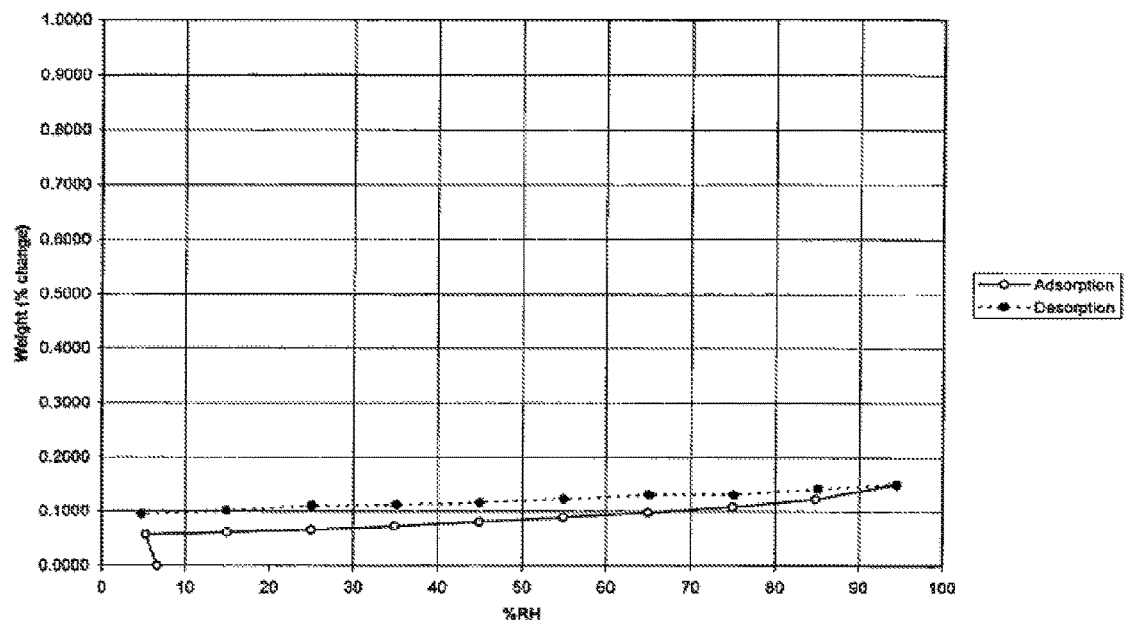
Figure 34. Automatic moisture sorption/desorption of MBX-102 Form E.

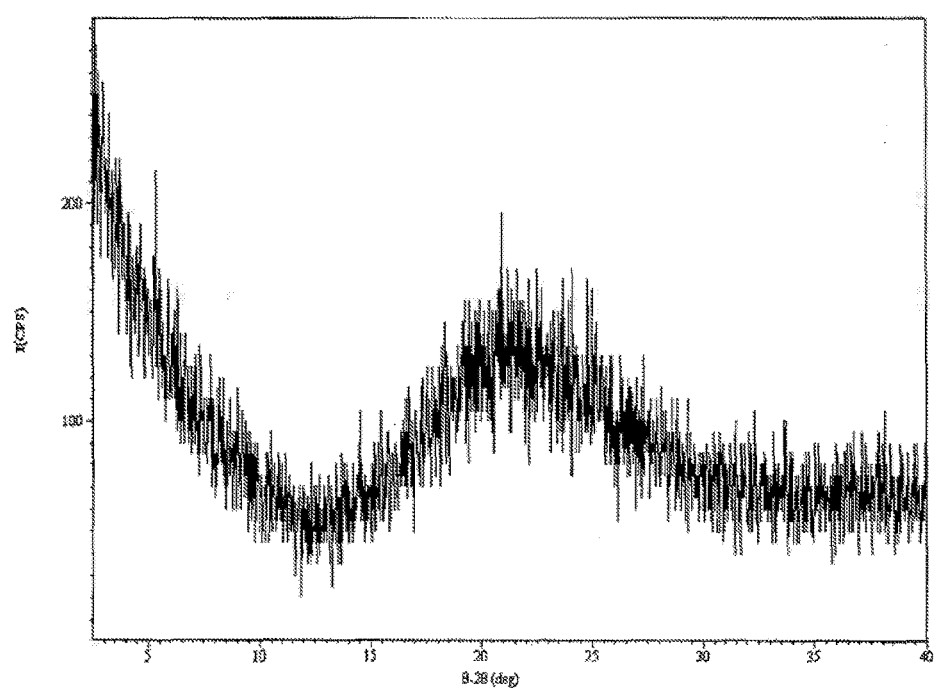
Figure 35. XRPD Pattern for Amorphous Form

Figure 36

Table A Approximate Solubility of MBX-102 (Form A)

| Solvent | Abbreviation | Solubility (mg/mL) |
|---|---|---|
| acetone | - | > 800 |
| acetonitrile | ACN | > 700 |
| benzene | - | > 600 |
| cyclohexane | - | 0.6 |
| cyclohexanol | - | > 300 |
| dichloromethane | DCM | > 600 |
| 1,4-dioxane | dioxane | > 700 |
| ethanol | EtOH | > 600 |
| ethyl acetate | EtOAc | > 800 |
| heptane | - | < 0.5 |
| hexanes | - | < 0.5 |
| methanol | MeOH | > 1000 |
| methyl ethyl ketone | MEK | > 800 |
| methyl tert-butyl ether | MTBE | > 300 |
| nitromethane | - | > 800 |
| 2-propanol | IPA | > 600 |
| tetrahydrofuran | THF | > 700 |
| 2,2,4-trimethylpentane | TMP | < 0.5 |
| toluene | - | > 300 |
| water | - | < 0.5 |

Table B. Approximate Solubility of MBX-102 at 50 °C[a] (Form A)

| Solvent | Abbreviation | Solubility (mg/mL) |
|---|---|---|
| cyclohexane | - | 2 |
| heptane | - | 1 |
| hexanes | - | 1 |
| 2,2,4-trimethylpentane | TMP | 1 |
| water | - | < 0.4 | a. Temperature is approximate.

Figure 37

Interconversion Slurry Experiments in Cyclohexane

| Starting form[a] | Slurry temp.[b] | Method[c] | Visual observation | XRPD results[d] |
|---|---|---|---|---|
| A + D ~40 mg | RT | slurried 6 days, vac filtered[e], vac dried RT | irregular-shaped particles, birefringence, extinction | Form A |
| | 50 °C | slurried 3 days, decant super, vac dried RT | irregular-shaped particles, tiny bent needles, birefringence, extinction | Form A |
| A, E ~20 mg each | RT | slurried 6 days, vac filtered[e], vac dried RT | irregular-shaped particles, narrow fibers, birefringence, extinction | Form A |
| A, E ~20 mg each | 50 °C | slurried 3 days, decant super, vac dried RT | irregular-shaped particles, birefringence, extinction | Form A + E |
| A + E | 50 °C | slurried 3 days, decant super, vac dried RT | irregular-shaped particles needles, fibers, birefringence, extinction | Form A, LC |
| A, B, D, E | RT | slurried 7 days, vac filtered, air-dried residual solid[e] | unknown morphology, birefringence, extinction | Pattern A |
| ~10 mg each | 5 °C | slurried 7 days, vac filtered, air-dried residual solid[e] | unknown morphology, no birefringence | Pattern A | a. The starting solids were combined with approximately 5-6 mL saturated solution (or pure solvent )
b. RT = ambient temperature. Reported temperatures and durations are approximate.
c. Super = supernatant, vac = vacuum.
d. LC = low crystallinity.
e. Re-combined filter solid with residual solid in original vial.

Figure 38. XRPD Peak Listing for Form C.

```
Peak Data List  [Total No. = 30]
No.     2Theta   d         I      I/Io    FWHM      Integrated I
1       9.8627   8.96093   404    19      0.29810   7487
2       13.2964  6.65355   1854   88      0.27570   27123
3       14.0433  6.30131   94     4       0.47330   2466
4       14.6714  6.03293   691    33      0.28070   10534
5       15.0400  5.88589   108    5       0.00000   0
6       15.5283  5.70189   916    43      0.25330   13156
7       15.9400  5.55553   150    7       0.21760   2025
8       16.4226  5.39335   101    5       0.25620   1473
9       19.6600  4.51192   82     4       0.34660   1901
10      20.3790  4.35433   1820   86      0.49450   45849
11      21.3435  4.15969   520    25      0.31370   8825
12      21.8600  4.06256   123    6       0.30000   2958
13      23.1194  3.84403   1227   58      0.29650   19788
14      24.5600  3.62171   95     4       0.16660   1078
15      24.8789  3.57601   334    16      0.36050   6108
16      25.5600  3.48224   225    11      0.14420   2494
17      25.8511  3.44369   2117   100     0.28400   30471
18      26.2400  3.39352   110    5       0.00000   0
19      26.8103  3.32262   800    38      0.31860   14380
20      27.3364  3.25985   444    21      0.32010   7427
21      28.6900  3.10906   196    9       0.23910   3056
22      30.1825  2.95863   439    21      0.22850   5265
23      30.7070  2.90928   377    18      0.25960   5276
24      31.2254  2.86215   281    13      0.35080   5610
25      31.9422  2.79954   703    33      0.28080   9954
26      32.3000  2.76934   110    5       0.29000   2131
27      32.7707  2.73063   377    18      0.26140   5088
28      36.1407  2.48336   129    6       0.28150   2204
29      37.3512  2.40561   73     3       0.29750   1497
30      38.1657  2.35613   339    16      0.22180   4345

Group:              MBX-102
Data:               Form C
File Name:          Form C.PKR Peak Datafile
comment             =
date & time         = 31-Dec-1969 19:00:00

Measurement Condition:

X-ray tube
target              = Cu
voltage             = 40.0 (kV)
current             = 30.0 (mA)

Slits
divergence slit     = 1.00000 (deg)
scatter slit        = 1.00000 (deg)
receiving slit      = 0.15000 (mm)
```

Figure 38 (continued). XRPD Peak Listing for Form C.

```
Scanning
drive axis               = 2Theta/Theta
scan range               = 5.200 - 39.780
scan mode                = Continuous Scan
scan speed               = 214748.3594 (deg/min)
sampling pitch           = 0.0200 (deg)
preset time              = 0.00 (sec)

Data Process Condition:

Smoothing                [AUTO]
smoothing points         = 15

B.G. Subtraction         [AUTO]
sampling points          = 15
repeat times             = 30

Ka1-a2 Separate          [MANUAL]
Ka1 a2 ratio             = 50.0 (%)

Peak Search              [AUTO]
differential points      = 15
FWHM threshold           = 0.050 (deg)
intensity threshold      = 30 (par mil)
FWHM ratio (n-1)/n       = 2

System Error Correction: [NO]
Precise Peak Correction: [NO]
```

CRYSTALLINE SOLID AND AMORPHOUS FORMS OF (−)-HALOFENATE AND METHODS RELATED THERETO

CROSS-REFERENCES TO RELATED APPLICATIONS

This application is a continuation of application Ser. No. 14/631,629, filed Feb. 25, 2015, issued as U.S. Pat. No. 9,233,914; which is a continuation of application Ser. No. 13/938,548, filed Jul. 10, 2013, issued as U.S. Pat. No. 8,993,797; which is a continuation of application Ser. No. 13/470,142, filed May 11, 2012, issued as U.S. Pat. No. 8,507,719; which is a continuation of application Ser. No. 11/408,609, filed Apr. 20, 2006, issued as U.S. Pat. No. 8,203,019. Application Ser. No. 11/408,609 claims the benefit of Application No. 60/673,655, filed Apr. 20, 2005, the content of which is incorporated by reference into application Ser. No. 11/408,609.

BACKGROUND OF THE INVENTION

The present invention relates to crystalline solid and amorphous forms of the title compound which has the chemical structure shown below:

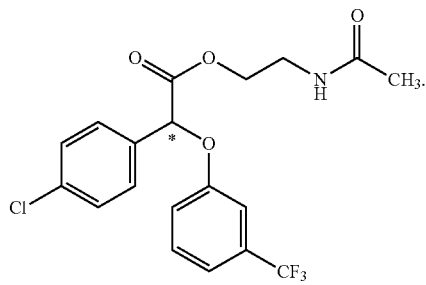 [SMILES: CC(=O)NCCOC(=O)C(Oc1cccc(C(F)(F)F)c1)c1ccc(Cl)cc1]

2-acetamidoethyl 4-chlorophenyl-(3-trifluoromethylphenoxy)-acetate, (3-trifluoromethylphenoxy)-(4-chlorophenyl)acetic acid 2-acetylaminoethyl ester or halofenate is a chiral compound which is useful in ameliorating Type II diabetes and hyperlipidemia (see, for example, U.S. Pat. No. 6,262,118 and U.S. patent application Ser. No. 10/656,567, which are incorporated by reference in their entirety). Halofenate contains a single chiral center at an asymmetrically substituted carbon atom alpha to one of the carbonyl carbon atoms (*), and therefore exists in two enantiomeric forms.

Significant side effects have been noted using racemic halofenate including gastrointestinal bleeding from stomach and peptic ulcers (see, e.g., Friedberg, S. J. et al., *Clin. Res.* (1986) Vol. 34, No. 2: 682A). In addition, there were some indications of drug-drug interactions of racemic halofenate with agents such as warfarin sulfate (also referred to as 3-(alpha-acetonylbenzyl)-4-hydroxycoumarin or COUMADIN™ (Dupont Pharmaceuticals, E.I. Dupont de Nemours and Co., Inc., Wilmington, Del. U.S.A.)) (see, e.g., Vesell, E. S. and Passantanti, G. T., *Fed. Proc.* (1972) 31(2): 538). COUMADIN™ is believed to be stereospecifically metabolized by cytochrome P450 2C9, the principal form of human liver P450 which modulates in vivo drug metabolism of several other drugs (see, e.g., Miners, J. O. et al, *Bri. J. Clin. Pharmacol.* (1998) 45: 525-538). Cytochrome P450 2C9 is inhibited by racemic α-(phenoxy)phenylacetic acid, e.g., halofenic acid. Thus, administration of a racemic halofenate can lead to a variety of drug interaction problems with other drugs, including anticoagulants, anti-inflammatory agents and other drugs that are metabolized by cytochrome P450 2C9.

It has been found that the (−)-enantiomer of halofenic acid is about twenty-fold less active in its ability to inhibit cytochrome P450 2C9 compared to the (+)-enantiomer (see, for example, U.S. Pat. No. 6,262,118). Thus, it is desirable to administer the (−)-enantiomer of halofenic acid or its derivatives which are substantially free of the (+)-enantiomer to reduce the possibility of drug interactions.

While biological activity is a sine non qua for an effective drug, a compound must also be capable of large scale manufacturing and the physical properties of the compound can markedly impact the effectiveness and cost of a formulated active ingredient.

Amorphous and different crystalline solid forms of compounds are frequently encountered among pharmaceutically useful compounds. Physical properties including solubility, melting point/endotherm maximum, density, hardness, crystalline shape and stability can be quite different for different forms of the same chemical compound.

Crystalline solid and amorphous forms may be characterized by scattering techniques, e.g., x-ray diffraction powder pattern, by spectroscopic methods, e.g., infra-red, solid state $^{13}C$ and $^{19}F$ nuclear magnetic resonance spectroscopy and by thermal techniques, e.g, differential scanning calorimetry or differential thermal analysis. Although the intensities of peaks in the x-ray powder diffraction patterns of different batches of a compound may vary slightly, the peaks and the peak locations are characteristic for a specific crystalline solid or amorphous form. Additionally, infrared, Raman and thermal methods have been used to analyze and characterize crystalline and solid amorphous forms. Solid and amorphous forms may be characterized by data from the X-ray powder diffraction pattern determined in accordance with procedures which are known in the art (see J. Haleblian, *J. Pharm. Sci.* 1975 64:1269-1288, and J. Haleblain and W. McCrone, *J. Pharm. Sci.* 1969 58:911-929).

There is a problem identifying a suitable form which (i) possesses adequate chemical stability during the manufacturing process, (ii) is efficiently prepared, purified and recovered, (ii) provides acceptable solubility in pharmaceutically acceptable solvents, (iii) is amenable to manipulation (e.g. flowability and particle size) and formulation with negligible decomposition or change of the physical and chemical characteristics of the compound, (iv) exhibits acceptable chemical stability in the formulation. In addition, forms containing a high molar percent of the active ingredient are highly desirable since they minimize the quantity of material which must be formulated and administered to produce a therapeutically effective dose. These often conflicting requirements make identification of suitable forms a challenging and important problem which must be solved by the skilled pharmaceutical scientist before drug development can proceed in earnest.

Therefore, there is a need for crystalline solid and amorphous forms of (−)-halofenate and an efficient process for producing crystalline solid forms of (−)-halofenate. Solutions to the above difficulties and deficiencies are needed before halofenate becomes effective for routine treatment of insulin resistance, Type 2 diabetes and hyperlipidemia.

Biphenyl compounds are generally crystalline, poorly water soluble and hydrophobic, resulting in difficulties in the preparation of pharmaceutical formulations and problems associated with bioavailability. Accordingly, efforts were made to discover amorphous and crystalline solid forms of (−)-halofenate and to investigate the properties thereof. There were discovered five crystalline solid forms and an amorphous form. The present invention fulfills the above needs by providing amorphous and crystalline solid forms of (−)-halofenate and methods for alleviating insulin resistance, Type 2 diabetes and hyperlipidemia, while presenting a better adverse effect profile.

BRIEF SUMMARY OF THE INVENTION

The invention provides the compound of formula (I):

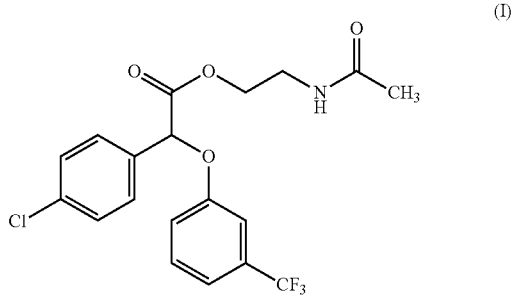 [SMILES: CC(=O)NCCOC(=O)C(Oc1cccc(C(F)(F)F)c1)c1ccc(Cl)cc1]

in substantially pure crystalline solid or amorphous forms.

In one embodiment, the present invention relates to "(−)-2-acetamidoethyl 4-chlorophenyl-(3-trifluoromethylphenoxy)-acetate", "(3-trifluoromethylphenoxy)-(4-chlorophenyl)acetic acid 2-acetylaminoethyl ester" or "(−)-halofenate", in a crystalline solid form, which for purposes of this invention are identified as Forms A, B, C, D and E. Forms A through E are anhydrous. In another embodiment, the present invention relates to (−)-halofenate in a substantially pure amorphous form.

Within each of the above embodiments, the present invention provides each of the crystalline forms and the amorphous form in a substantially pure form.

In another aspect, the present invention provides a method of preparing (−)-halofenate in a crystalline solid form A, including substantially pure forms, comprising at least one of:
(i) heating (−)-halofenate in at least one solvent selected from the group consisting of heptane, 2-propanol, and combinations thereof; crystallizing at a temperature of from about 50° C. to −10° C. and drying until the crystals contain less than 0.05% solvent;
(ii) drying a crystal of crystalline solid form B of (−)-halofenate;
(iii) drying a crystal of crystalline solid form C of (−)-halofenate;
(iv) heating (−)-halofenate in at least one solvent selected from the group consisting of heptane, 2-propanol, and combinations thereof; crystallizing in the presence of a crystal of a solid form of (−)-halofenate at a temperature of from about 50° C. to −10° C. and drying until the crystals contain less than 0.05% solvent; and
(v) crystallizing (−)-halofenate from at least one solvent selected from the group consisting of acetonitrile, benzene, cyclohexanol, t-butyl methyl ether and combinations thereof and drying.

In another aspect, the present invention provides a method of preparing (−)-halofenate in a solid form B, including a substantially pure crystalline solid form B, comprising crystallizing (−)-halofenate from at least one solvent selected from the group consisting of heptane, 2-propanol, and combinations thereof and at a temperature of from about 20° C. to −10° C. and drying until the crystals contain from about 2% to about 3% solvent.

In another aspect, the present invention provides a method of preparing (−)-halofenate in a crystalline solid form C, including a substantially pure crystalline solid form C, comprising crystallizing (−)-halofenate from at least one solvent selected from the group consisting of heptane, 2-propanol, and combinations thereof and at a temperature of from about 20° C. to −10° C. and drying until the crystals contain about 0.05% to about 0.3% solvent.

In another aspect, the present invention provides a method of preparing (−)-halofenate in a crystalline solid form D, including substantially pure crystalline solid form D, comprising crystallizing (−)-halofenate from at least one solvent selected from the group consisting of acetonitrile, benzene, cyclohexanol, t-butyl methyl ether, methanol, water and combinations thereof and drying.

In another aspect, the present invention provides a method of preparing (−)-halofenate in a crystalline solid form E, including substantially pure crystalline solid form E, comprising crystallizing (−)-halofenate from t-butyl methyl ether and heptane and drying.

In another aspect, the present invention provides a method of preparing (−)-halofenate in an amorphous form, including substantially pure amorphous form, comprising heating (−)-halofenate at high humidity.

The present invention also provides pharmaceutical compositions comprising a pharmaceutically acceptable carrier and a therapeutically effective amount of (−)-halofenate containing in a substantially pure form selected from the group consisting of crystalline solid form A, B, C, D, E and amorphous.

In another aspect, the invention provides methods for preventing or treating/modulating Type 2 diabetes in a mammal containing a therapeutically effective amount of an (−)-halofenate in a substantially pure form selected from the group consisting of crystalline solid form A, B, C, D, E and amorphous and a pharmaceutically acceptable carrier. The present invention further provides methods for modulating insulin resistance and alleviating hyperlipidemia in a mammal comprising administering to the mammal a therapeutically effective amount of (−)-halofenate in a substantially pure form selected from the group consisting of crystalline solid form A, B, C, D, E and amorphous.

BRIEF DESCRIPTION OF THE DRAWINGS

FIG. 1: XRPD pattern of crystalline solid form A of (−)-halofenate.
FIG. 2: XRPD peak listing for crystalline solid form A of (−)-halofenate.
FIG. 3: FT-infra red spectrum of crystalline solid form A of (−)-halofenate.
FIG. 4: FT-infra red spectrum with labeled peaks of crystalline solid form A of (−)-halofenate.
FIG. 5: FT-Raman spectrum of crystalline solid form A of (−)-halofenate.
FIG. 7: Cyclic DSC analysis of crystalline solid form A of (−)-halofenate.
FIG. 8: Hot stage microscopy of crystalline solid form A of (−)-halofenate.
FIG. 9: Light microscopy of crystalline solid form A of (−)-halofenate after cyclic DSC.

FIG. 10: Thermal analysis of crystalline solid form A of (−)-halofenate.

FIG. 11: Automated moisture sorption/desorption data of crystalline solid form A of (−)-halofenate.

FIG. 12: $^1$H NMR spectrum of crystalline solid form A, D and E of (−)-halofenate.

FIG. 13: XRPD pattern of crystalline solid form B of (−)-halofenate.

FIG. 14: XRPD peak listing for crystalline solid form B of (−)-halofenate.

FIG. 18: XRPD pattern of crystalline solid form D of (−)-halofenate.

FIG. 19: XRPD peak listing for crystalline solid form D of (−)-halofenate.

FIG. 20: FT-infra red spectrum of crystalline solid form D of (−)-halofenate.

FIG. 21: FT-infra red spectrum with labeled peaks of crystalline solid form D of (−)-halofenate.

FIG. 22: FT-Raman spectrum of crystalline solid form D of (−)-halofenate.

FIG. 24: Thermal analysis of crystalline solid form D of (−)-halofenate.

FIG. 25: Automatic moisture sorption/desorption data of crystalline solid form D of (−)-halofenate.

FIG. 26: XRPD pattern of crystalline solid form E of (−)-halofenate.

FIG. 27: XRPD peak listing of crystalline solid form E of (−)-halofenate.

FIG. 28: FT-infra red spectrum of crystalline solid form E of (−)-halofenate.

FIG. 29: FT-infra red spectrum with peak listing of crystalline solid form E of (−)-halofenate.

FIG. 30: FT-Raman spectrum of crystalline solid form E of (−)-halofenate.

FIG. 31: FT-Raman spectrum with peak listing of crystalline solid form E of (−)-halofenate.

FIG. 32: Thermal analysis of crystalline solid form E of (−)-halofenate.

FIG. 33: Hot stage microscopy of crystalline solid form E of (−)-halofenate.

FIG. 34: Automated moisture sorption/desorption analysis of crystalline solid form E of (−)-halofenate.

FIG. 35: XRPD of amorphous form of (−)-halofenate.

FIG. 36: Approximate solubility of (−)-halofenate in solvents at RT and at 50° C.

FIG. 37: Summary table of interconversion studies.

FIG. 38: XRPD peak listing for crystalline solid form C (−)-halofenate.

DETAILED DESCRIPTION OF THE INVENTION

I. Definitions

Figure 6:
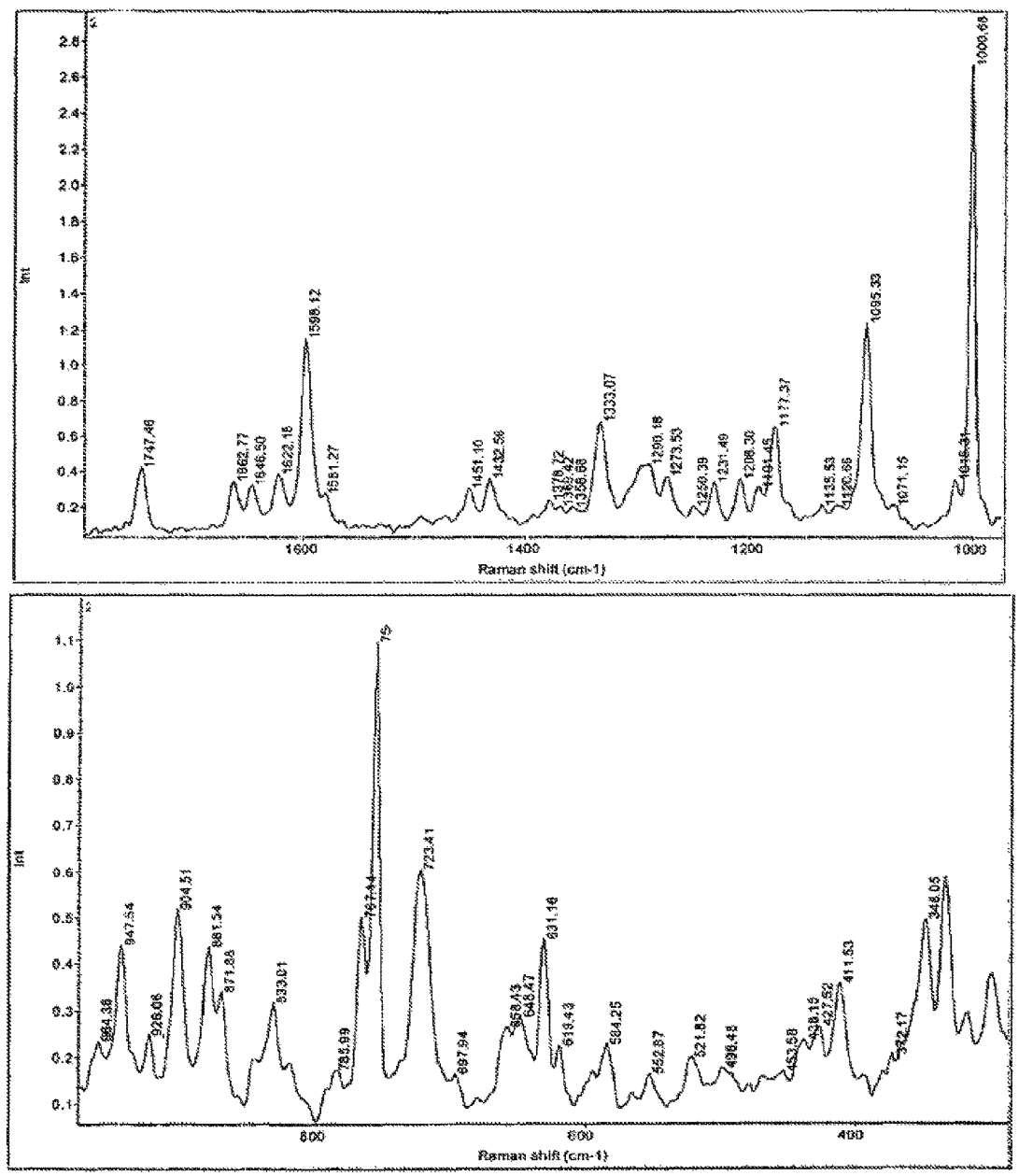
FIG. 6: FT-Raman spectrum with labeled peaks of crystalline solid form A of (−)-halofenate.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "about" as used herein means variation one might see in measurements taken among different instruments, samples, and sample preparations. Such variation may include, for instance, colligative properties for thermal measurements. Typical variation among different x-ray diffractometers and sample preparations for crystalline solid forms is on the order of 0.2° 2θ. Typical variation for Raman and IR spectrometers is on the order of twice the resolution of the spectrometer. The resolution of the spectrometer used was about 2 cm$^{-1}$.

The term "solvate" as used herein means a compound of the invention or a salt, thereof, that further includes a stoichiometric or non-stoichiometric amount of a solvent bound by non-covalent intermolecular forces in an amount of greater than about 0.3% when prepared according to the invention.

The term "hydrate" as used herein means a compound of the invention or a salt thereof, that further includes a stoichiometric or non-stoichiometric amount of water bound by non-covalent intermolecular forces. Hydrates are formed by the combination of one or more molecules of water with one of the substances in which the water retains its molecular state as $H_2O$, such combination being able to form one or more hydrate.

The term "anhydrous" as used herein means a compound of the invention or a salt thereof that contains less than about 3% by weight water or solvent when prepared according to the invention.

The term "drying" as used herein means a method of removing solvent and/or water from a compound of the invention which, unless otherwise specified, may be done at atmospheric pressure or under reduced pressure and with or without heating until the level of solvent and/or water contained reached an acceptable level.

The term "polymorphs" as used herein means crystal structures in which a compound can crystallize in different crystal packing arrangements, all of which have the same elemental composition. Different crystal forms usually have different X-ray diffraction patterns, infrared spectra, melting points/endotherm maximums, density hardness, crystal shape, optical and electrical properties, stability and solubility. Recrystallization solvent, rate of crystallization, storage temperature, and other factors may cause one crystal form to dominate.

The term "solid form" as used herein means crystal structures in which compounds can crystallize in different packing arrangements. Solid forms include polymorphs, hydrates, and solvates as those terms are used in this invention. Different solid forms, including different polymorphs, of the same compound exhibit different x-ray powder diffraction patterns and different spectra including infra-red, Raman, and solid-state NMR. Their optical, electrical, stability, and solubility properties may also differ.

The term "characterize" as used herein means to select data from an analytical measurement such as X-ray powder diffraction, infra-red spectroscopy, Raman spectroscopy, and/or solid-state NMR to distinguish one solid form of a compound from other solid forms of a compound.

The term "mammal" includes, without limitation, humans, domestic animals (e.g., dogs or cats), farm animals (cows, horses, or pigs), monkeys, rabbits, mice, and laboratory animals.

The term "insulin resistance" can be defined generally as a disorder of glucose metabolism. More specifically, insulin resistance can be defined as the diminished ability of insulin to exert its biological action across a broad range of concentrations producing less than the expected biologic effect (see, e.g., Reaven, G. M., *J. Basic & Clin. Phys. & Pharm.* (1998) 9: 387-406 and Flier, *J. Ann Rev. Med.* (1983) 34:145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plaminogen activator inhibitor-1), has been referred to as "Syndrome X" (see, e.g., Reaven, G. M., *Physiol. Rev.* (1995) 75: 473-486).

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described above, Type 1 diabetes is generally the result of an absolute deficiency of insulin, the hormone which regulates glucose utilization. Type 2 diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many Type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of Type 1 or Type 2 diabetes.

The term "secondary diabetes" is diabetes resulting from other identifiable etiologies which include: genetic defects of β cell function (e.g., maturity onset-type diabetes of youth, referred to as "MODY," which is an early-onset form of Type 2 diabetes with autosomal inheritance; see, e.g., Fajans S. et al., *Diabet. Med.* (1996) (9 Suppl 6): S90-5 and Bell, G. et al., *Annu. Rev. Physiol.* (1996) 58: 171-86;) genetic defects in insulin action; diseases of the exocrine pancreas (e.g., hemochromatosis, pancreatitis, and cystic fibrosis); certain endocrine diseases in which excess hormones interfere with insulin action (e.g., growth hormone in acromegaly and cortisol in Cushing's syndrome); certain drugs that suppress insulin secretion (e.g., phenytoin) or inhibit insulin action (e.g., estrogens and glucocorticoids); and diabetes caused by infection (e.g., rubella, Coxsackie, and CMV); as well as other genetic syndromes. The guidelines for diagnosis for Type 2 diabetes, impaired glucose tolerance, and gestational diabetes have been outlined by the American Diabetes Association (see, e.g., The Expert Committee on the Diagnosis and Classification of Diabetes Mellitus, *Diabetes Care*, (1999) Vol 2 (Suppl 1): S5-19).

Many organic compounds exist in optically active forms, i.e., they have the ability to rotate the plane of plane-polarized light. In describing an optically active compound, the prefixes R and S are used to denote the absolute configuration of the molecule about its chiral center(s). The prefixes "d" and "l" or (+) and (−) are employed to designate the sign of rotation of plane-polarized light by the compound, with (−) or l meaning that the compound is "levorotatory" and with (+) or d is meaning that the compound is "dextrorotatory". There is no correlation between nomenclature for the absolute stereochemistry and for the rotation of an enantiomer. For a given chemical structure, these compounds, called "stereoisomers," are identical except that they are mirror images of one another. A specific stereoisomer can also be referred to as an "enantiomer," and a mixture of such isomers is often called an "enantiomeric" or "racemic" mixture. See, e.g., Streitwiesser, A. & Heathcock, C. H., INTRODUCTION TO ORGANIC CHEMISTRY, $2^{nd}$ Edition, Chapter 7 (MacMillan Publishing Co., U.S.A. 1981). The optical rotation $[\alpha]_D$ of (−)-halofenate was measured in methyl alcohol.

"Chiral" or "chiral center" refers to a carbon atom having four different substituents. However, the ultimate criterion of chirality is non-superimposability of mirror images.

The terms "CPTA" and "halofenic acid" refer to the acid form of 4-Chlorophenyl-(3-trifluoromethylphenoxy)-acetic acid.

"Enantiomeric mixture" means a chiral compound having a mixture of enantiomers, including a racemic mixture. Preferably, enantiomeric mixture refers to a chiral compound having a substantially equal amounts of each enantiomers. More preferably, enantiomeric mixture refers to a racemic mixture where each enantiomer is present in an equal amount.

"Enantiomerically enriched" refers to a composition where one enantiomer is present in a higher amount than prior to being subjected to a separation process.

"Enantiomeric excess" or "% ee" refers to the amount of difference between the first enantiomer and the second enantiomer. Enantiomeric excess is defined by the equation: % ee=(% of the first enantiomer)−(% of the second enantiomer). Thus, if a composition comprises 98% of the first enantiomer and 2% of the second enantiomer, the enantiomeric excess of the first enantiomer is 98%-2% or 96%.

"Optical purity" refers to the amount of a particular enantiomer present in the composition. For example, if a composition comprises 98% of the first enantiomer and 2% of the second enantiomer, the optical purity of the first enantiomer is 98%.

"Derivative" refers to compounds such as those disclosed in U.S. Pat. No. 3,517,050.

The term "rate" when referring to a formation of a salt refers to kinetic and/or thermodynamic rates.

As used herein, the terms "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "substantially free of its (+) stereoisomer," as used herein, means that the compositions contain a substantially greater proportion of the (−) isomer of halofenate in relation to the (+) isomer. In the present invention the term "(−)-halofenate" means that it is substantially free of its (+)

isomer. In one embodiment, the term "substantially free of its (+) stereoisomer," as used herein, means that the composition is at least 90% by weight of the (−) isomer and 10% by weight or less of the (+) isomer. In another embodiment, the term "substantially free of its (+) stereoisomer," as used herein, means that the composition contains at least 91% by weight of the (−) isomer and 9% by weight or less of the (+) isomer. In another embodiment, the term "substantially free of its (+) stereoisomer," as used herein, means that the composition contains at least 92% by weight of the (−) isomer and 8% by weight or less of the (+) isomer. In another embodiment, the term "substantially free of its (+) stereoisomer," as used herein, means that the composition contains at least 93% by weight of the (−) isomer and 7% by weight or less of the (+) isomer. In another embodiment, the term "substantially free of its (+) stereoisomer," as used herein, means that the composition contains at least 94% by weight of the (−) isomer and 6% by weight or less of the (+) isomer. In another embodiment, the term "substantially free of its (+) stereoisomer," as used herein, means that the composition contains at least 95% by weight of the (−) isomer and 5% by weight or less of the (+) isomer. In another embodiment, the term "substantially free of its (+) stereoisomer," as used herein, means that the composition contains at least 96% by weight of the (−) isomer and 4% by weight or less of the (+) isomer. In another embodiment, the term "substantially free of its (+) stereoisomer," as used herein, means that the composition contains at least 97% by weight of the (−) isomer and 3% by weight or less of the (+) isomer. In another embodiment, the term "substantially free of its (+) stereoisomer," as used herein, means that the composition contains at least 98% by weight of the (−) isomer and 2% by weight or less of the (+) isomer. In another embodiment, the term "substantially free of its (+) stereoisomer," means that the composition contains greater than 99% by weight of the (−) isomer. These percentages are based upon the total amount of halofenate in the composition.

The term "substantially pure," as used herein without reference to the (+) isomer, means that the compositions contain a substantially greater proportion of the (−)-halofenate in relation to the sum of other chemical compounds, other than solvent, including the (+)-isomer of halofenate, other crystalline solid forms of (−)-halofenate and the amorphous form, and chemical impurities, collectively "non-solvent compounds." In one embodiment, the term "substantially pure," as used herein, means that the composition is at least 90% by weight of (−)-halofenate and 10% by weight or less of other non-solvent compounds. In one embodiment, the term "substantially pure," as used herein, means that the composition is at least 91% by weight of (−)-halofenate and 9% by weight or less of other non-solvent compounds. In one embodiment, the term "substantially pure," as used herein, means that the composition is at least 92% by weight of (−)-halofenate and 8% by weight or less of other non-solvent compounds. In one embodiment, the term "substantially pure," as used herein, means that the composition is at least 93% by weight of (−)-halofenate and 7% by weight or less of other non-solvent compounds. In one embodiment, the term "substantially pure," as used herein, means that the composition is at least 94% by weight of (−)-halofenate and 6% by weight or less of other non-solvent compounds. In one embodiment, the term "substantially pure," as used herein, means that the composition is at least 95% by weight of (−)-halofenate and 5% by weight or less of other non-solvent compounds. In one embodiment, the term "substantially pure," as used herein, means that the composition is at least 96% by weight of (−)-halofenate and 4% by weight or less of other non-solvent compounds. In one embodiment, the term "substantially pure," as used herein, means that the composition is at least 97% by weight of (−)-halofenate and 3% by weight or less of other non-solvent compounds. In one embodiment, the term "substantially pure," as used herein, means that the composition is at least 98% by weight of (−)-halofenate and 2% by weight or less of other non-solvent compounds. In one embodiment, the term "substantially pure," as used herein, means that the composition is at least 99% by weight of (−)-halofenate and 1% by weight or less of other non-solvent compounds. In one embodiment, the term "substantially pure," as used herein, means that the composition is at least 99.5% by weight of (−)-halofenate and 0.5% by weight or less of other non-solvent compounds. In another embodiment, the term "substantially pure," as used herein, means that the composition contains at least 90% by weight of a particular crystalline solid or amorphous form of the (−)-isomer and 10% by weight or less of other crystalline solid or amorphous forms of the (−)-isomer. In another embodiment, the term "substantially pure," as used herein, means that the composition contains at least 90% by weight of a particular crystalline solid or amorphous form of the (−)-isomer and 10% by weight or less of other crystalline solid or amorphous forms of the (−)-isomer. In another embodiment, the term "substantially pure," as used herein, means that the composition contains at least 91% by weight of a particular crystalline solid or amorphous form of the (−)-isomer and 9% by weight or less of other crystalline solid or amorphous forms of the (−)-isomer. In another embodiment, the term "substantially pure," as used herein, means that the composition contains at least 92% by weight of a particular crystalline solid or amorphous form of the (−)-isomer and 8% by weight or less of other crystalline solid or amorphous forms of the (−)-isomer. In another embodiment, the term "substantially pure," as used herein, means that the composition contains at least 93% by weight of a particular crystalline solid or amorphous form of the (−)-isomer and 7% by weight or less of other crystalline solid or amorphous forms of the (−)-isomer. In another embodiment, the term "substantially pure," as used herein, means that the composition contains at least 94% by weight of a particular crystalline solid or amorphous form of the (−)-isomer and 6% by weight or less of other crystalline solid or amorphous forms of the (−)-isomer. In another embodiment, the term "substantially pure," as used herein, means that the composition contains at least 95% by weight of a particular crystalline solid or amorphous form of the (−)-isomer and 5% by weight or less of other crystalline solid or amorphous forms of the (−)-isomer. In another embodiment, the term "substantially pure," as used herein, means that the composition contains at least 96% by weight of a particular crystalline solid or amorphous form of the (−)-isomer and 4% by weight or less of other crystalline solid or amorphous forms of the (−)-isomer. In another embodiment, the term "substantially pure," as used herein, means that the composition contains at least 97% by weight of a particular crystalline solid or amorphous form of the (−)-isomer and 3% by weight or less of other crystalline solid or amorphous forms of the (−)-isomer. In another embodiment, the term "substantially pure," as used herein, means that the composition contains at least 98% by weight of a particular crystalline solid or amorphous form of the (−)-isomer and 2% by weight or less of other crystalline solid or amorphous forms of the (−)-isomer. In another embodiment, the term "substantially pure," as used herein, means that the composition contains at least 99% by weight of a particular crystalline solid or amorphous form of the (−)-isomer and 1% by weight or less of other crystalline solid or amorphous forms of the (−)-isomer. In another embodiment, the term "substantially pure," as used herein, means that the composition contains at least 99.5% by weight of a particular crystalline solid or amorphous form of the (−)-isomer and 0.5% by weight or less of other crystalline solid or amorphous forms of the (−)-isomer. These percentages are based upon the total amount of halofenate in the composition.

The term "in an isolated form" means unmixed or unformulated with pharmaceutically acceptable excipients or carriers.

The term "hyperinsulinemia" refers to the presence of an abnormally elevated level of insulin in the blood.

The term "secretagogue" means a substance or compound that stimulates secretion. For example, an insulin secretagogue is a substance or compound that stimulates secretion of insulin.

The term "hemoglobin" or "Hb" refers to a respiratory pigment present in erythrocytes, which is largely responsible for oxygen transport. A hemoglobin molecule comprises four polypeptide subunits (two α chain systems and two β chain systems, respectively). Each subunit is formed by association of one globin protein and one heme molecule which is an iron-protoporphyrin complex. The major class of hemoglobin found in normal adult hemolysate is adult hemoglobin (referred to as "HbA"; also referred to $HbA_0$ for distinguishing it from glycated hemoglobin, which is referred to as "$HbA_1$," described infra) having $\alpha_2\beta_2$ subunits. Trace components such as $HbA_2$ ($\alpha_2\delta_2$) can also be found in normal adult hemolysate.

Among classes of adult hemoglobin HbAs, there is a glycated hemoglobin (referred to as "$HbA_1$," or "glycosylated hemoglobin"), which may be further fractionated into $HbA_{1a1}$, $HbA_{1a2}$, $HbA_{1b}$, and $HbA_{1c}$ with an ion exchange resin fractionation. All of these subclasses have the same primary structure, which is stabilized by formation of an aldimine (Schiff base) by the amino group of N-terminal valine in the β subunit chain of normal hemoglobin HbA and glucose (or, glucose-6-phosphate or fructose) followed by formation of ketoamine by Amadori rearrangement.

The term "glycosylated hemoglobin" (also referred to as "$HbA_{1c}$,", "GHb", "hemoglobin-glycosylated", "diabetic control index" and "glycohemoglobin"; hereinafter referred to as "hemoglobin $A_{1c}$") refers to a stable product of the nonenzymatic glycosylation of the β-chain of hemoglobin by plasma glucose. Hemoglobin $A_{1c}$ comprises the main portion of glycated hemoglobins in the blood. The ratio of glycosylated hemoglobin is proportional to blood glucose level. Therefore, hemoglobin $A_{1c}$ rate of formation directly increases with increasing plasma glucose levels. Since glycosylation occurs at a constant rate during the 120-day lifespan of an erythrocyte, measurement of glycosylated hemoglobin levels reflect the average blood glucose level for an individual during the preceding two to three months. Therefore determination of the amount of glycosylated hemoglobin $HbA_{1c}$ can be a good index for carbohydrate metabolism control. Accordingly, blood glucose levels of the last two months can be estimated on the basis of the ratio of $HbA_{1c}$ to total hemoglobin Hb. The analysis of the hemoglobin $A_{1c}$ in blood is used as a measurement enabling long-term control of blood glucose level (see, e.g., Jain, S., et al., *Diabetes* (1989) 38: 1539-1543; Peters A., et al., *JAMA* (1996) 276: 1246-1252).

The term "symptom" of diabetes, includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea, and ketoacidosis (enhanced production of ketone bodies in the blood).

The term "complication" of diabetes includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications which generally result from large blood vessel damage. These complications include, e.g., cardiovascular disease and peripheral vascular disease. Cardiovascular disease refers to diseases of blood vessels of the heart. See. e.g., Kaplan, R. M., et al., "Cardiovascular diseases" in HEALTH AND HUMAN BEHAVIOR, pp. 206-242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "antihyperlipidemic" refers to the lowering of excessive lipid concentrations in blood to desired levels.

The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "modulate" refers to the treating, prevention, suppression, enhancement or induction of a function or condition. For example, the compounds of the present invention can modulate hyperlipidemia by lowering cholesterol in a human, thereby suppressing hyperlipidemia.

The term "treating" also means the management and care of a human subject for the purpose of combating the disease, condition, or disorder and includes the administration of a compound of the present invention to prevent the onset of the symptoms or complications, alleviating the symptoms or complications, or eliminating the disease, condition, or disorder.

The term "cholesterol" refers to a steroid alcohol that is an essential component of cell membranes and myelin sheaths and, as used herein, incorporates its common usage. Cholesterol also serves as a precursor for steroid hormones and bile acids.

The term "triglyceride(s)" ("TGs"), as used herein, incorporates its common usage. TGs consist of three fatty acid molecules esterified to a glycerol molecule and serve to store fatty acids which are used by muscle cells for energy production or are taken up and stored in adipose tissue.

Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small of the intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form the low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

The term "dyslipidemia" refers to abnormal levels of lipoproteins in blood plasma including both depressed and/or elevated levels of lipoproteins (e.g., elevated levels of LDL, VLDL and depressed levels of HDL).

Exemplary Primary Hyperlipidemia include, but are not limited to, the following:

(1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels;

(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of Type 1 diabetes, Type 2 diabetes, Cushing's syndrome, hypothroidism and certain types of renal failure; (2) drug risk factors, which include, birth control pills; hormones, such as estrogen, and corticosteroids; certain diuretics; and various β blockers; (3) dietary risk factors include dietary fat intake per total calories greater than 40%; saturated fat intake per total calories greater than 10%; cholesterol intake greater than 300 mg per day; habitual and excessive alcohol use; and obesity.

The terms "obese" and "obesity" refers to, according to the World Health Organization, a Body Mass Index (BMI) greater than 27.8 $kg/m^2$ for men and 27.3 $kg/m^2$ for women (BMI equals weight (kg)/height ($m^2$). Obesity is linked to a variety of medical conditions including diabetes and hyperlipidemia. Obesity is also a known risk factor for the development of Type 2 diabetes (See, e.g., Barrett-Conner, E., *Epidemol. Rev.* (1989) 11: 172-181; and Knowler, et al., *Am. J Clin. Nutr.* (1991) 53:1543-1551).

II. Solid and Amorphic Embodiments of the Invention and their Preparation

The present invention is directed to (−)-halofenate in a substantially pure crystalline solid and/or amorphous form and processes for their preparation and pharmaceutical compositions comprising these forms and these forms in an isolated form. (−)-Halofenate has the following general formula:

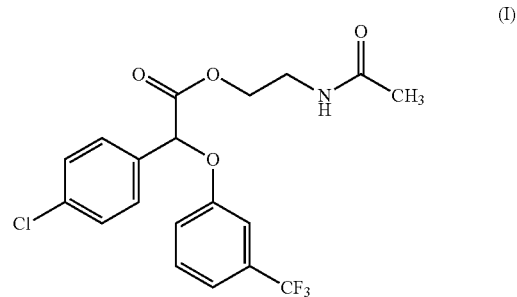

(I)

The chemical synthesis of the racemic mixture of halofenate can be performed by the methods described in U.S. Pat. No. 3,517,050, the teaching of which is incorporated herein by reference. The individual enantiomers can be obtained by resolution of the racemic mixture of enantiomers by the methods described in U.S. Pat. No. 6,262,118 and U.S. Patent Application Ser. No. 60/608,927, and using conventional means known to and used by those of skill in the art (see, e.g., Jaques, J., et al., in ENANTIOMERS, RACEMATES, AND RESOLUTIONS, John Wiley and Sons, New York (1981), the teachings of which are incorporated herein by reference). Other standard methods of resolution known to those skilled in the art, including but not limited to, simple crystallization and chromatographic resolution, can also be used (see, e.g., STEREOCHEMISTRY OF CARBON COMPOUNDS (1962) E. L. Eliel, McGraw Hill; Lochmuller, *J. Chromatography* (1975) 113, 283-302). Additionally, optically pure isomers can be prepared from the racemic mixture by enzymatic biocatalytic resolution. Enzymatic biocatalytic resolution has been described previously (see, e.g., U.S. Pat. Nos. 5,057,427 and 5,077,217, the disclosures of which are incorporated herein by reference).

Other methods of obtaining enantiomers include stereospecific synthesis (see, e.g., Li, A. J. et al., *Pharm. Sci.* (1997) 86:1073-1077).

In developing a process for production of (−)-halofenate as an active pharmaceutical ingredient (API), two factors were of great importance: the impurity profile and the crystal morphology of (−)-halofenate. The results from initial isolation and crystallization work showed that the impurity profile of (−)-halofenate mainly consisted of CPTA whose abundances ranged from 1.07 to 3.9%. Preferably the API has levels of impurities below 0.2% and is in the most thermodynamically stable crystalline solid form. The difficulty in controlling the level of impurities and the crystalline solid nature of the API required the development of a process for the production of (−)-halofenate to provide the requisite purity and the proper crystal form. Subsequent isolation and crystallization work indicated that there were at least five crystalline solid forms (designated as Forms A, B, C, D and E) and an amorphous form of the API. In one embodiment, the present invention provides (−)-halofenate in new crystalline forms designated as Form A, Form B, Form C, Form D, Form E as well as an amorphous form.

The solid forms of the invention may be described by one or more of several techniques including X-ray powder diffraction, Raman spectroscopy, IR spectroscopy, and thermal methods. Further, combinations of such techniques may be used to describe the invention. For example, one or more X-ray powder diffraction peaks combined with one or more Raman peaks may be used to describe one or more solid forms of the invention in a way that differentiates it from the other solid forms.

Although it characterizes a form, it is not necessary to rely only upon an entire diffraction pattern or spectrum to characterize a solid form. Those of ordinary skill in the pharmaceutical arts recognize that a subset of a diffraction pattern or spectrum may be used to characterize a solid form provided that subset distinguishes the solid form from the other forms being characterized. Thus, one or more X-ray powder diffraction peaks alone may be used to characterize a solid form. Likewise, one or more IR peaks alone or Raman peaks alone may be used to characterize a solid form. Such characterizations are done by comparing the X-ray, Raman, and IR data amongst the forms to determine characteristic peaks.

One may also combine data from other techniques in such a characterization. Thus, one may rely upon one or more peaks from an x-ray powder diffraction and for example, Raman or IR data, to characterize a form. For example, if one or more x-ray peaks characterize a form, one could also consider Raman or IR data to characterize the form. It is sometimes helpful to consider Raman data, for example, in pharmaceutical formulations.

Initial examination of the D morphology of (−)-halofenate identified the first three distinct crystal forms: forms A, B and C. The polymorphs were identified at three stages of the crystallization process from 6/1 (v/v) heptane/2-propanol. (1) Crystalline form B was isolated after crystallization of the crude wet-cake from 25% aqueous isopropyl alcohol, (2) crystalline form C was formed after drying the crude wet-cake to effect solvent removal, and (3) crystalline solid form A was formed after complete solvent removal. Using the protocols described in the Examples, these three polymorphs could be generated and interconverted, demonstrating the concurrency between solvent incorporation and polymorph interconversion.

Figure 15:
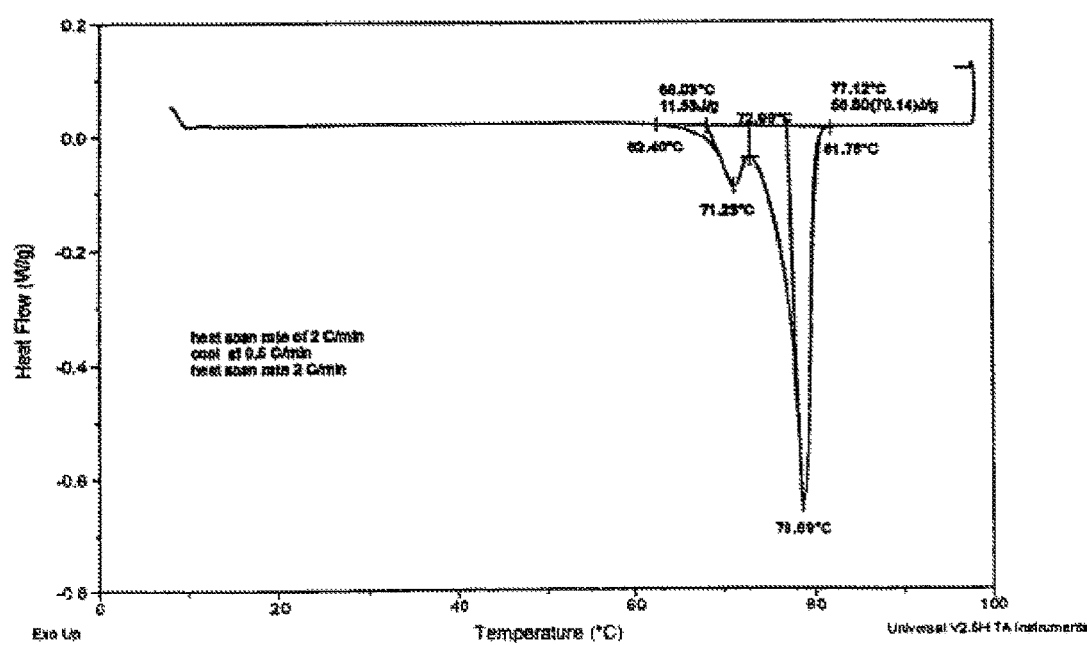
FIG. 15: DSC analysis of crystalline solid form B of (−)-halofenate.

Thus filtration of a slurry of (−)-halofenate in 6/1 heptane/2-propanol (IPA) followed by drying the isolated white crystalline solid at room temperature under reduced pressure gave the morphologically distinct crystalline solid (−)-halofenate/form B. FIGS. 15 and 13 respectively show the DSC trace and the X-ray powder pattern for the cystalline solid. In the DSC trace, the sharpness of the endotherm peak at about 71° C. is particularly noteworthy, and in the X-ray powder diffraction pattern, the peaks at about 6.2° 2θ and about 12.4° 2θ are characteristic peaks of the pattern (for a discussion of the theory of X-ray powder diffraction patterns see "X-ray diffraction procedures" by H. P. Klug and L. E. Alexander, J. Wiley, New York (1974)). The peaks at about 6.2° 2θ and about 12.4° 2θ characterize Form B with respect to Forms A, C, D, and E because none of those forms have peaks to within 0.4 2θ, twice approximate precision of X-ray powder diffraction peaks, of the two Form B peaks.

Because the typical variation in any given x-ray powder diffraction peak is on the order of 0.2° 2θ, when selecting peaks to characterize a polymorph, one selects peaks that are at least twice that value (i.e., 0.4° θ) from a peak from another polymorph. Thus, in a particular polymorph x-ray pattern, a peak that is at least 0.4° θ from a peak in another polymorph is eligible to be considered as a peak that can either alone or together with another peak be used to characterize that polymorph. In the case of Form B, the set of peaks at about 6.2° 2θ and about 12.4° 2θ are at least 0.4° θ away from peaks in any of Forms A, C, D, or E as illustrated in table 1. Tables 1 and 2 identify the main peaks of Forms A, B, C, D and E.

The data in those tables come from FIGS. 2, 14, 19, 27 and 32 which report two-theta angles to four decimal places. Because the variability of x-ray data is in the first decimal place, the invention is described to one decimal point. For example, the peak listed in table 2 as 22.05 originates in FIG. 2 as 22.0479° 2θ. To one decimal point, this value is 22.0° 2θ, not 22.1° 2θ. Thus, the value of "about 22.0° 2θ" is used to help describe the invention where appropriate not "about 22.1° 2θ." Likewise, the value of 17.45° 2θ in table 2 originates from FIG. 19 as 17.4451° 2θ and, therefore, is rounded to 17.4° 2θ and not 17.5° 2θ. From that list, one sees that the peak at about 6.2° 2θ (on the table listed as 6.16° 2θ), when taken to one decimal point, is greater than 0.4° 2θ away from any peak in Forms A, C or D. Thus, the peak at about 6.2° 2θ can be used to distinguish Form B from Form A, C and D. It cannot, by itself, be used to distinguish over Form E because that form contains a peak at about 6.4° 2θ (6.43° 2θ in Tables 1 and 2). Thus, more data is required to differentiate Form B from Form E. The peak at about 12.4° 2θ (12.42° 2θ in Tables 1 and 2) is more than 0.4° 2θ away from any peak in Form E.

Although the peak list for Form E in FIG. 27 lists a peak at about 12.4° 2θ, intensity at that position in the actual pattern in FIG. 26 is not discernable from noise and indeed the intensity of the listed peak in FIG. 27 is only 4% of the maximum peak. For this reason, what FIG. 27 calls a peak at about 12.4° 2θ is not a peak and was not included in the peak list of table 1. By comparison, the X-ray powder diffraction pattern of Form B in FIG. 13 has a clearly discernable peak at about 12.4° 2θ. Thus, the peak at about 12.4° 2θ can be used to distinguish Form B from Form E. Thus, the Form B peaks at about 6.2° 2θ and 12.4° 2θ characterize Form B with respect to Forms A, C, D, and E. The solid form isolated at this stage in the process contained between about 2% and about 3% solvent by weight and could be converted to other solid forms upon drying or slurrying.

TABLE 1

(−)-Halofenate XRPD Peak (°2θ) and Relative Intensity Listing (I/I₁)

| Form A | | Form B | | Form C | | Form D | | Form E | | Amorphous Broad peak |
|---|---|---|---|---|---|---|---|---|---|---|
| °2θ | I/I₁ | °2θ | I/I₁ | °2θ | I/I₁ | °2θ | I/I₁ | °2θ | I/I₁ | between (°2θ): |
| 7.26 | 13 | 6.16 | 81 | 9.86 | 19 | 4.59 | 34 | 5.87 | 17 | 15 and 30 |
| 7.75 | 9 | 6.96 | 9 | 13.30 | 88 | 9.62 | 31 | 6.43 | 14 | |
| 8.96 | 6 | 10.24 | 5 | 14.04 | 4 | 15.86 | 8 | 8.94 (broad) | 12 | |
| 10.79 | 18 | 11.75 | 6 | 14.67 | 33 | 16.28 | 18 | 10.85 (broad) | 6 | |
| 13.08 | 36 | 12.42 | 21 | 15.53 | 43 | 17.45 | 100 | 11.79 | 70 | |
| 13.50 | 17 | 14.01 | 12 | 15.94 | 7 | 18.34 | 12 | 12.97 | 17 | |
| 14.72 | 53 | 15.74 | 4 | 16.42 | 5 | 18.74 | 14 | 13.64 | 17 | |
| 15.40 | 19 | 17.45 | 8 | 20.38 | 86 | 19.30 | 23 | 14.70 | 10 | |
| 17.91 | 49 | 18.22 | 12 | 21.34 | 25 | 20.00 | 7 | 15.41 (broad) | 8 | |
| 18.96 | 41 | 18.78 | 100 | 21.86 | 6 | 20.40 | 27 | 17.73 | 43 | |
| 20.09 | 29 | 19.47 | 13 | 23.12 | 58 | 21.36 | 76 | 18.12 | 12 | |
| 21.08 | 38 | 20.06 | 51 | 24.88 | 16 | 24.26 | 29 | 18.59 | 100 | |
| 21.64 | 26 | 20.50 | 33 | 25.85 | 100 | 24.52 | 51 | 18.97 | 29 | |
| 22.05 | 100 | 21.26 | 15 | 26.81 | 38 | 25.17 | 34 | 19.72 | 65 | |
| 22.40 | 19 | 22.54 | 21 | 27.34 | 21 | 26.26 (broad) | 6 | 20.08 | 24 | |
| 23.47 | 57 | 23.52 | 12 | 28.69 | 9 | | | 21.28 | 85 | |
| 24.41 | 18 | 23.82 | 23 | 30.18 | 21 | | | 22.38 | 50 | |
| 25.59 | 33 | 25.28 | 13 | 30.71 | 18 | | | 23.62 | 59 | |
| 26.92 (broad) | 20 | 25.95 | 14 | 31.23 | 13 | | | 24.39 (broad) | 17 | |
| 27.91 (broad) | 9 | 26.80 | 9 | 31.94 | 33 | | | 26.80 | 44 | |
| 29.33 (broad) | 16 | 27.24 | 10 | 32.77 | 18 | | | | | |
| 30.66 (broad) | 13 | 27.71 | 10 | 36.14 | 6 | | | | | |
| 31.26 (broad) | 9 | 28.24 | 7 | 37.35 (broad) | 3 | | | | | |
| | | 29.66 (broad) | 6 | 38.17 | 16 | | | | | |
| | | 31.67 | 7 | | | | | | | |

TABLE 2

Unique Crystalline (−)-Halofenate XRPD Peaks (no other peaks within ±0.4 °2θ make up a unique set for each crystalline form) to two significant figures after the decimal point

| Form A °2θ | Form B °2θ | Form C °2θ | Form D °2θ | Form E °2θ |
|---|---|---|---|---|
| 10.79 | 6.16 | 9.86 | 9.62 | 11.79 |
| 22.05 | 12.42 | 13.30 | 17.45 | 12.97 |
| 29.33 | | | | |

Preferred orientation can affect peak intensities, but not peak positions, in XRPD patterns. In the case of (−)-halofenate, preferred orientation has the most effect on the region of 22-30° 2θ. Preferred orientation causes some peaks in this region to be diminished (or increased) and less resolved from each other. Crystal habit does not clearly differentiate between the solid forms; a variety of habits have been observed for each of the forms, including needles, blades, plates, and irregular-shaped particles.

Thus in one embodiment, the invention relates to (−)-halofenate in a crystalline solid form, including a substantially pure form, which provides at least one of:
(i) an X-ray powder diffraction pattern substantially in accordance with FIG. 13; and
(ii) a DSC scan substantially in accordance with FIG. 15;
herein designated as Form B.

In another embodiment, the invention relates to (−)-halofenate in a crystalline solid form, including a substantially pure form, which provides at least one of:
(i) an X-ray powder diffraction pattern comprising peaks at about 6.2° 2θ and about 12.4° 2θ; and
(ii) a DSC endotherm maximum of about 71° C.;
herein designated as Form B.

In another embodiment, the invention relates to (−)-halofenate in a crystalline solid form, including a substantially pure form, which provides an X-ray powder diffraction pattern comprising peaks at about 6.2° 2θ and about 12.4° 2θ herein designated as Form B.

In yet another embodiment of the invention, the invention relates to (−)halofenate in a crystalline solid form, including a substantially pure form, which provides an x-ray powder diffraction pattern comprising peaks at about 6.2° 2θ, about 12.4° 2θ, and at least one peak selected from about 18.8° 2θ, about 20.1° 2θ, and about 14.0° 2θ; herein designated as Form B.

In another embodiment, the invention relates to (−)-halofenate in a crystalline solid form, including a substantially pure form, which provides a DSC endotherm maximum of about 71° C.;
herein designated as Form B.

Figure 16:
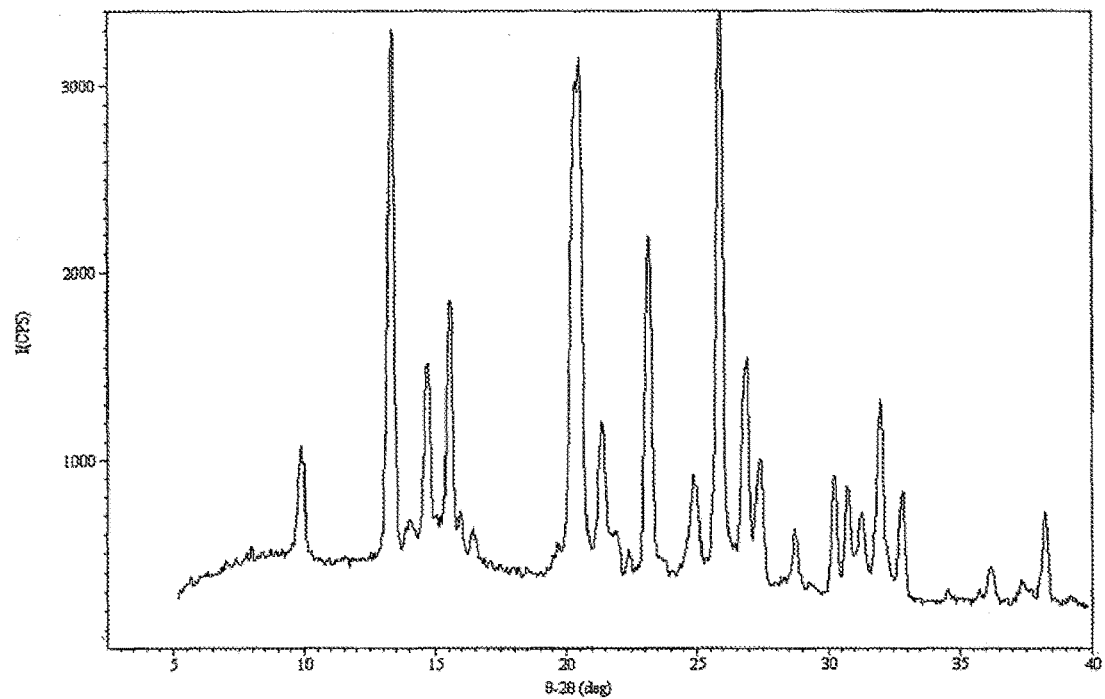
FIG. 16: XRPD pattern of crystalline solid form C of (−)-halofenate.
Figure 17:
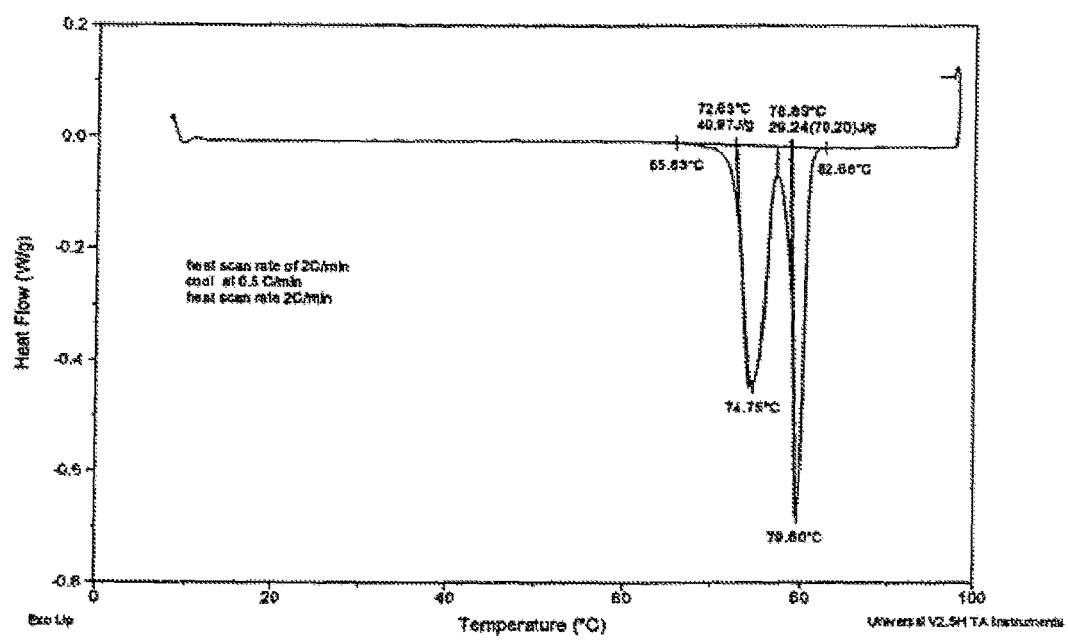
FIG. 17: DSC analysis of crystalline solid form C of (−)-halofenate.

When the resultant wetcake was further dried under reduced pressure at 50° C., a white crystalline solid, polymorph C was isolated. FIGS. 17 and 16 respectively show the DSC trace and the X-ray powder pattern for this crystalline solid. These results were observed when the level of heptane was lowered to at about 0.3 wt %. This data shows that 0.3 wt % or more of heptane was necessary to cause polymorph interconversion from form C to form A. In the DSC trace, a weak transition at about 75° C. is noteworthy, however the peaks at about 9.9° 2θ and about 13.3° 2θ in the X-ray powder diffraction pattern characterize Form C with respect to Forms A, B, D, and E. Because none of those forms have peaks to within 0.4 2θ, the approximate precision of X-ray powder diffraction peaks, of the two characteristic Form C peaks (see Tables 1 and 2). From that list, one sees that the peaks at about 9.9° 2θ and 13.3° 2θ (in Tables 1 and 2 listed as 9.86° 2θ and 13.30° 2θ, respectively), when taken to one decimal point, is greater than 0.4° 2θ away from any peak in Forms A, B, D or E. Thus, the peaks at about 9.9° 2θ and 13.3° 2θ can be used to distinguish Form B from Forms A, B, D and E. Form C could be converted to other forms upon drying or slurrying.

Thus in one embodiment, the invention relates to (−)-halofenate in a crystalline solid form, including a substantially pure form, wherein the compound provides at least one of:
(i) an X-ray powder diffraction pattern substantially in accordance with FIG. 17; and
(ii) a DSC scan substantially in accordance with FIG. 16;
herein designated as Form C.

In another embodiment, the invention relates to (−)-halofenate in a crystalline solid form, including a substantially pure form, which provides wherein the compound provides an X-ray powder diffraction pattern comprising peaks at about 9.9° 2θ and about 13.3° 2θ; herein designated as Form C.

In yet another embodiment of the invention, the invention relates to (−)halofenate in a crystalline solid form, including a substantially pure form, which provides an x-ray powder diffraction pattern comprising peaks at about 9.9° 2θ, about 13.3° 2θ, and at least one peak selected from about 15.5° 2θ, about 23.1° 2θ, about 14.7° 2θ, and about 25.9° 2θ; herein designated as Form C.

The conversion of form C to form A was effected by further drying the white, crystalline solid at 50° C. under reduced pressure. FIGS. 3, 7 and 1 respectively show the IR spectrum, the DSC trace, and the X-ray powder pattern for this cystalline solid. These results were observed when the remaining solvent was removed. A comparison of these data with the data presented for other crystalline solid forms of (−)-halofenate clearly indicates that this crystalline solid has a unique crystalline solid form. Differential scanning calorimetry (DSC) of form A of (−)-halofenate defined an endothermic onset of melting at 78° C. with an endotherm maximum of approximately 80° C. (see FIG. 10). Hot stage microscopy showed an onset of melting at approximately 73° C. with completion of melt at approximately 76° C. (See FIG. 8). The strong transition at 80° C. in the DSC trace contrasts with the peaks at 71 and 75° C. shown in FIGS. 15 and 17. Decomposition occurred with an onset at approximately 200° C. The melted solid did not recrystallize upon cooling as evidenced by the lack of an exothermic event during cyclic DSC experiments, but the material appears to crystallize from a melt in a closed system as examined by light microscopy (see FIG. 9). The X-ray powder diffraction pattern definitively proves that this crystalline solid is unique when compared to polymorph B. The pattern is characterized by peaks at about 10.8°, 2θ about 22.0° 2θ, and about 29.3° 2θ which are clearly different from those obtained for form B (see Tables 1 and 2). The peaks at about 10.8° 2θ, about 22.0° 2θ, and at about 29.3° 2θ characterize Form A because none of Forms B, D, or E contain three peaks that are within 0.4° 2θ of about 10.8° 2θ, about 22.0° 2θ, and about 29.3° 2θ, respectively. Form A exhibits an endotherm maximum at about 80° C. by DSC and Form C melts at about 75° C. by DSC. Thus, one can use DSC, when the measurement is done according to the operating parameters of the invention, to distinguish Form A from Form C. Accordingly, the Form A X-ray diffraction peaks at about 10.8° 2θ, about 22.0° 2θ, and about 29.3° 2θ together with a DSC maximum endotherm at about 80° C. characterize Form A with respect to Forms B, C, D, and E. It is an anhydrous material as indicated by the 0.16% weight loss from 25 to 100° C. in the TGA. The material was also shown to be non-hygroscopic with no weight gain at 65% relative humidity (RH) and only 1.6% weight gain at 65-95% RH, which was essentially unchanged after moisture sorption analysis. All of the weight gain was lost in a desorption study at 5% RH (see FIG. 11). The solution phase $^1$H NMR spectra showed Form A contained less than 0.05% solvents (see FIG. 12). The crystalline solid isolated at this stage in the process provided the most thermodynamically stable crystalline white solid and could be stored for long periods (months) without decomposition.

Generation of the crystal form A also occurred by crystallization from acetonitrile, benzene, cyclohexanol, t-butyl methyl ether, methanol, methyl ethyl ketone, toluene, tetrahydrofuran and combinations thereof.

Thus in one embodiment, the invention relates to (−)-halofenate in a crystalline solid form, including a substantially pure form, which provides at least one of:
(i) an infra red spectrum substantially in accordance with FIG. 3;
(ii) a Raman spectrum substantially in accordance with FIG. 5;
(iii) an X-ray powder diffraction pattern substantially in accordance with FIG. 1; and
(iv) a DSC scan substantially in accordance with FIG. 7;
herein designated as Form A.

Thus in one embodiment, the invention relates to (−)-halofenate in a crystalline solid form, including a substantially pure form, which provides an IR spectrum substantially in accordance with FIG. 3; herein designated as Form A.

Thus in one embodiment, the invention relates to (−)-halofenate in a crystalline solid form, including a substantially pure form, which provides a Raman spectrum substantially in accordance with FIG. 5; herein designated as Form A.

In another embodiment, the invention relates to (−)-halofenate in a crystalline solid form, including a substantially pure form, which provides at least one of:
(i) an infra red spectrum comprising absorption peaks at about 3479, 3322, 3082, 2886, 2842, 1918, 1850, 1753, 1709, 1651, 1596, 1548, 1494, 1461, 1430, 1371, 1340, 1272, 1231, 1127, 1070, 1017, 926, 903 and 884 expressed in wave number cm$^{-1}$;
(ii) a Raman spectrum comprising absorption peaks at about 3087, 3071, 2959, 2933, 2857, 1747, 1663, 1647, 1622, 1598, 1451, 1433, 1333, 1290, 1274, 1231, 1208, 1177, 1095, 1015, 1001, 964, 948, 926, 905, 882, 872, 833, 767, 757, 723 and 631 expressed in wave number cm$^{-1}$;
(iii) an X-ray powder diffraction pattern comprising peaks at about 10.8° 2θ about 22.0° 2θ, and about 29.3° 2θ and
(iv) a DSC endotherm maximum of about 80° C.
herein designated as Form A.

In another embodiment, the invention relates to (−)-halofenate in a crystalline solid form, including a substantially pure form, which provides an X-ray powder diffraction pattern comprising peaks at about 10.8° 2θ, about 22.0° 2θ and about 29.3° 2θ herein designated as Form A.

In yet another embodiment of the invention, the invention relates to (−)-halofenate in a crystalline solid form, including a substantially pure form, which provides an x-ray powder diffraction pattern comprising peaks at about 10.8° 2θ, about 22.0° 2θ, about 29.3° 2θ, and an infrared spectrum comprising at lease one peak selected from about 3322 cm$^{-1}$ and about 2886 cm$^{-1}$; herein designated as Form A.

In a further embodiment of the invention, the invention relates to (−)-halofenate in a crystalline solid form, including a substantially pure form, which provides an x-ray powder diffraction pattern comprising peaks at about 10.8° 2θ, about 22.0° 2θ, about 29.3° 2θ, and a Raman spectrum comprising at least one peak selected from about 3087 cm$^{-1}$ and about 1663 cm$^{-1}$; herein designated as Form A.

In an additional embodiment of the invention, the invention relates to (−)halofenate in a crystalline solid form, including a substantially pure form, which provides an x-ray powder diffraction pattern comprising peaks at about 10.8° 2θ, about 22.0° 2θ, about 29.3° 2θ, an infrared spectrum comprising at lease one peak selected from about 3322 cm-1 and about 2886 cm-1, and a Raman spectrum comprising at least one peak selected from about 3087 cm-1 and about 1663 cm-1 herein designated as Form A.

In another embodiment, the invention relates to (−)-halofenate in a crystalline solid form, including a substantially pure form, which provides a DSC endotherm maximum of about 80° C.; herein designated as Form A.

The interconversion of forms B and C to A can also be effected by crystallizing the respective melts. Thus B may be converted to A either directly or B may be converted to A via C by these newly discovered processes. Both processes produce the single, thermodynamically most stable polymorph A of (−)-halofenate in greater than 99% chemical purity. Later analysis of a sample of crystal form C also showed that over time conversion to crystal form E (below) occurred.

The dependence of the process on the solvent system was studied and two additional solid forms D and E were identified. Solubility studies were done on Form A in water and a variety of organic solvents. The data is summarized in FIG. 36. In general, (−)-halofenate was fairly soluble in (greater than 300 mg/mL) in most organic solvents tested, the exceptions being water and very non-polar solvents (i.e. cyclohexane, hexanes, heptanes and 2,2,4-trimethylpentane). For these solvents, ambient solubility was less than 1 mg/mL. Solubility was also determined in these solvents at approximately 50° C. (see FIG. 36). In general, elevating the temperature increased the solubility of (−)-halofenate except in water for which there was no measurable increase. While Form A is preferred for formulations, it exhibits lower solubility and therefore requires higher temperatures and longer times to dissolve in some crystallization solvents.

Figure 23:
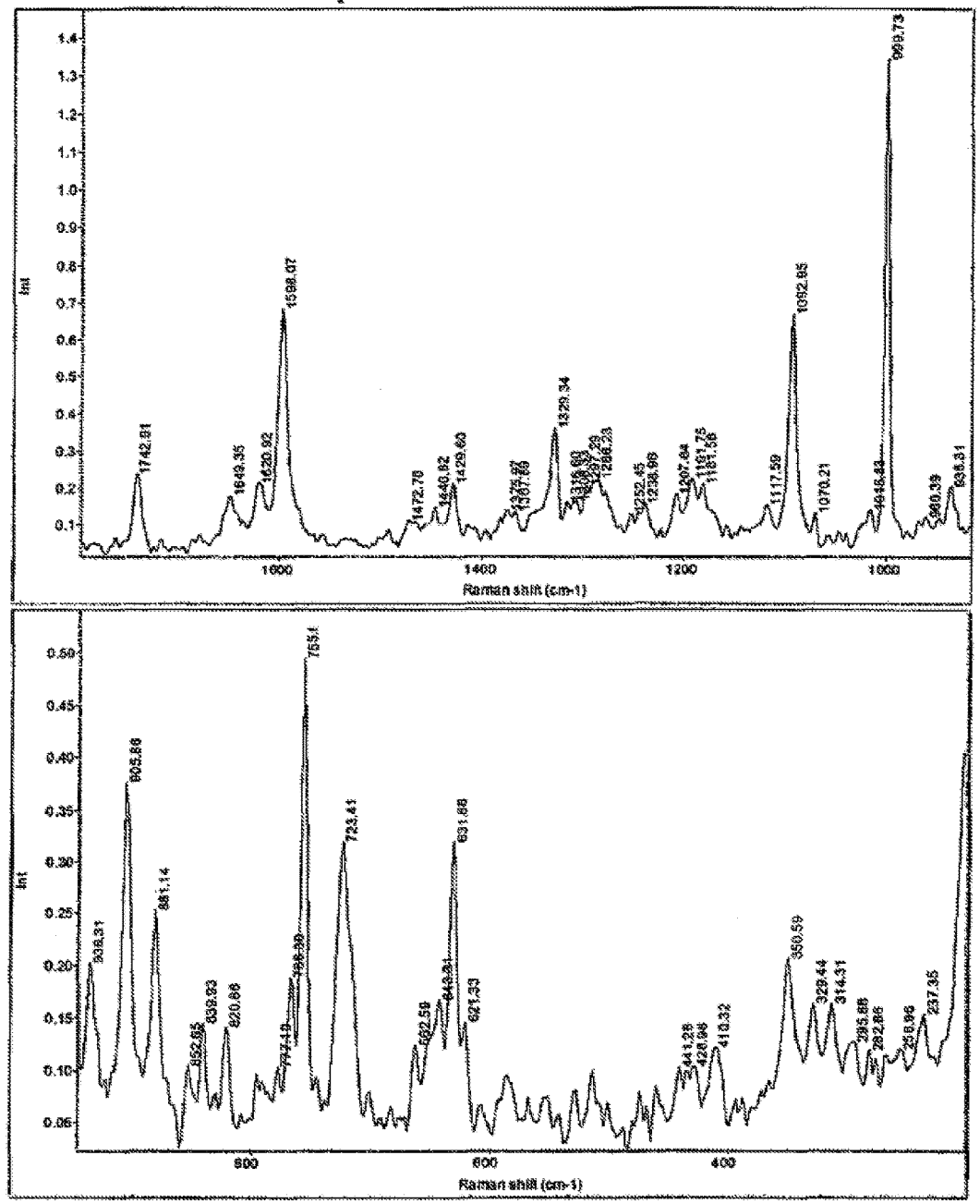
FIG. 23: FT-Raman spectrum with labeled peaks of crystalline solid form D of (−)-halofenate.

Generation of the crystal form D occurred by crystallization from acetone or ethanol. FIGS. 20, 24 and 18 respectively show the IR spectrum, the DSC trace and the X-ray powder pattern for this crystalline solid. All of the characterization data was obtained using a sample prepared from dichloromethane. A comparison of these data with the data presented above clearly indicates that this crystalline solid has a unique solid form. A comparison of the XRPD pattern of Form D to other forms of (−)-halofenate is shown in Table 2. The X-ray powder diffraction pattern definitively proves that this crystalline solid is unique when compared to polymorphs A, B, C and E. The pattern is characterized by peaks at about 9.6° 2θ and about 17.4° 2θ clearly different from those obtained for forms A, B C and E. The peaks at about 9.6° 2θ and at about 17.4° 2θ characterize Form D with respect to Forms A, B, C and E because none of these other forms contain two peaks that are within 0.4° 2θ of 9.6° 2θ and 17.4° 2θ respectively. The DSC of form D of (−)-halofenate defined an endothermic onset of melting at about 72° C. with a endotherm maximum of approximately about 74° C. (see FIG. 24). Hot stage microscopy showed an onset of melting at approximately 73° C. with a complete melt at approximately 74° C. Decomposition occurred with on onset at approximately 225° C. The transition at 74° C. in the DSC trace contrasts with those at 80° C., 71° C., 75° C. and 75° C. shown for Forms A-C and E. Form D exhibited an approximate 0.15% weight loss from approximately 25-100° C. (FIG. 25). The TGA weight loss is probably due to trace amounts of surface water as seen in $^1$H NMR spectrum (FIG. 12). No other solvent was detected by NMR, which confirms that Form D is anhydrous. The non-hygroscopicity of Form D was established by a moisture sorption/desorption study. A sample of Form D showed negligible weight gain (less than 0.1% at 95% RH (see FIG. 25). The crystalline solid resulting from the moisture sorption/desorption remained Form D. Other spectroscopic data acquired for Form D: FT-IR (see FIGS. 21-22) and FT-Raman (see FIGS. 23-24) showed that form D is distinguishable from other forms by these methods (see Tables 3 and 4). Form D could be converted to Form A upon slurring.

TABLE 3

IR Peak Listing for (−)-Halofenate (peaks > 400 cm$^{-1}$)
Peak Positions in Wavenumbers (cm$^{-1}$)

| Form A | Form D | Form E |
|---|---|---|
| 3479 | 3469 | 3475 |
| 3322 | 3297 | 3301 |
| 3082 | 3086 | 3092 |
| 2886 | 2968 | 2969 |
| 2842 | 2930 | 2933 |
| 1918 | 2870 | 2871 |
| 1850 | 1747 | 1750 |
| 1753 | 1740 | 1706 |
| 1709 | 1703 | 1660 |
| 1651 | 1647 | 1597 |
| 1596 | 1597 | 1563 |
| 1548 | 1554 | 1493 |
| 1494 | 1492 | 1460 |
| 1461 | 1460 | 1429 |
| 1430 | 1429 | 1370 |
| 1371 | 1369 | 1338 |
| 1340 | 1345 | 1232 |
| 1272 | 1295 | 1178 |
| 1231 | 1232 | 1126 |
| 1127 | 1209 | 1070 |
| 1070 | 1193 | 1015 |
| 1017 | 1124 | 906 |
| 926 | 1069 | 886 |
| 903 | 1015 | 820 |
| 884 | 906 | |
| | 880 | |
| | 838 | |
| | 819 | |

TABLE 4

Raman Peak Listing for (−)-Halofenate (peaks > 400 cm$^{-1}$)
Peak Positions in Wavenumbers (cm$^{-1}$)

| Form A | Form D | Form E |
|---|---|---|
| 3087 | 3077 | 3071 |
| 3071 | 3063 | 2969 |

TABLE 4-continued

Raman Peak Listing for (−)-Halofenate (peaks > 400 cm$^{-1}$)
Peak Positions in Wavenumbers (cm$^{-1}$)

| Form A | Form D | Form E |
|---|---|---|
| 2959 | 2970 | 2933 |
| 2933 | 2932 | 1746 |
| 2857 | 1743 | 1657 |
| 1747 | 1649 | 1621 |
| 1663 | 1621 | 1598 |
| 1647 | 1598 | 1448 |
| 1622 | 1430 | 1432 |
| 1598 | 1329 | 1334 |
| 1451 | 1208 | 1291 |
| 1433 | 1192 | 1232 |
| 1333 | 1182 | 1179 |
| 1290 | 1093 | 1094 |
| 1274 | 1000 | 1001 |
| 1231 | 936 | 907 |
| 1208 | 906 | 881 |
| 1177 | 881 | 767 |
| 1095 | 756 | 756 |
| 1015 | 723 | 722 |
| 1001 | 632 | 632 |
| 964 | | |
| 948 | | |
| 926 | | |
| 905 | | |
| 882 | | |
| 872 | | |
| 833 | | |
| 767 | | |
| 757 | | |
| 723 | | |
| 631 | | |

Thus in one embodiment, the invention relates to (−)-halofenate in a crystalline solid form, including a substantially pure form, which provides at least one of:
(i) an infra red spectrum substantially in accordance with FIG. 20;
(ii) a Raman spectrum substantially in accordance with FIG. 22; and
(iii) an X-ray powder diffraction pattern substantially in accordance with FIG. 18; and
(iv) a DSC scan substantially in accordance with FIG. 24;
herein designated as Form D.

Thus in one embodiment, the invention relates to (−)-halofenate in a crystalline solid form, including a substantially pure form, which provides an infra red spectrum substantially in accordance with FIG. 20;
herein designated as Form D.

Thus in one embodiment, the invention relates to (−)-halofenate in a crystalline solid form, including a substantially pure form, which provides a Raman spectrum substantially in accordance with FIG. 22;
herein designated as Form D.

In another embodiment, the invention relates to (−)-halofenate in a crystalline solid form, including a substantially pure form, which provides at least one of:
(i) an infra red spectrum comprising absorption peaks at about 3469, 3297, 3086, 2968, 2930, 2870, 1747, 1740, 1703, 1647, 1597, 1554, 1492, 1460, 1429, 1369, 1345, 1295, 1232, 1209, 1193, 1124, 1069, 1015, 906, 880, 838 and 819 cm$^{-1}$;
(ii) a Raman spectrum comprising absorption peaks at about 3077, 3063, 2970, 2932, 1743, 1649, 1621, 1598, 1430, 1329, 1208, 1192, 1182, 1093, 1000, 936, 906, 881, 756, 723 and 632 cm$^{-1}$;
(iii) an X-ray powder diffraction pattern comprising peaks at about 9.6° 2θ and about 17.4° 2θ; and
(iv) a DSC endotherm maximum at about 74° C.;
herein designated as Form D.

In another embodiment, the invention relates to (−)-halofenate in a crystalline solid form, including a substantially pure form, which provides an X-ray powder diffraction pattern comprising peaks at about 9.6° 2θ and about 17.4° 2θ; herein designated as Form D.

In another embodiment, the invention relates to (−)-halofenate in a crystalline solid form, including a substantially pure form, which provides a DSC endotherm maximum at about 74° C.;
herein designated as Form D.

In yet another embodiment of the invention, the invention relates to (−)-halofenate in a crystalline solid form, including a substantially pure form, which provides an x-ray powder diffraction pattern comprising peaks at about 9.6° 2θ, about 17.4° 2θ, and an infrared spectrum comprising peaks at least one peak selected from about 3469 cm$^{-1}$ and about 2870 cm$^{-1}$; herein designated as Form D.

In a further embodiment of the invention, the invention relates to (−)-halofenate in a crystalline solid form, including a substantially pure form, which provides an x-ray powder diffraction pattern comprising peaks at about 9.6° 2θ, about 17.4° 2θ, and a Raman spectrum comprising at least one peak selected from about 3077 cm$^{-1}$ and about 1329 cm$^{-1}$; herein designated as Form D.

In an additional embodiment of the invention, the invention relates to (−)halofenate in a crystalline solid form, including a substantially pure form, which provides an x-ray powder diffraction pattern comprising peaks at about 9.6° 2θ, about 17.4° 2θ, an infrared spectrum comprising peaks at least one peak selected from about 3469 cm$^{-1}$ and about 2870 cm$^{-1}$, and a Raman spectrum comprising at least one peak selected from about 3077 cm$^{-1}$ and about 1329 cm$^{-1}$; herein designated as Form D.

Generation of the crystal form E occurred by crystallization from heptane and t-butyl methyl ether. FIGS. 28, 32 and 26 respectively show the IR spectrum, the DSC trace, and the X-ray powder pattern for this crystalline solid. A comparison of the XRPD pattern of Form E to other forms of (−)-halofenate is shown in Tables 1 and 2 and clearly indicates that this crystalline solid has a unique solid form. The pattern is characterized by peaks at about 11.8° 2θ, and about 13.0° 2θ which are different from those obtained for forms A-D. The peaks at about 11.8° 2θ, and about 13.0° 2θ characterize Form E because none of Forms A, B, C or D contain a peak that is within 0.4° 2θ of about 11.8° 2θ and about 13.0° 2θ. The DSC shows major endotherms at 75 and 80° C. The first endothermic transition at 75° C. was shown to be the onset of a melting transition by hot stage microscopy (FIG. 33) and therefore after the first melt, form interconversion may occur. The second endotherm possibly corresponds to the melting of Form A at 80° C. Decomposition occurred with on onset at approximately 225° C. Form E exhibited an approximate 0.42% with loss from approximately 25-100° C. (FIG. 34) The TGA weight loss is probably due to trace amounts of surface water as seen in NMR spectrum (see FIG. 12). No other solvent was detected by NMR, which confirms that Form E is anhydrous. The non-hygroscopicity of Form E was established by a moisture sorption/desorption study. A sample of Form E showed negligible weight gain (less than 0.2% at 95% RH, see FIG. 34). The crystalline solid resulting from the moisture sorption/desorption remained Form E. Other spectroscopic data acquired for Form E (FT-IR, FIGS. 28-29 and FT-Raman, FIGS. 30-31) showed that Form E can be distinguished by these methods. Form E could be converted to Form A upon slurring.

Thus in one embodiment, the invention relates to (−)-halofenate in a crystalline solid form, including a substantially pure form, which provides at least one of:
(i) a infra red spectrum substantially in accordance with FIG. 28;
(ii) a Raman spectrum substantially in accordance with FIG. 30; and
(iii) a X-ray powder diffraction pattern substantially in accordance with FIG. 26;
herein designated as Form E.

Thus in one embodiment, the invention relates to (−)-halofenate in a crystalline solid form, including a substantially pure form, which provides a infra red spectrum substantially in accordance with FIG. 28;
herein designated as Form E.

Thus in one embodiment, the invention relates to (−)-halofenate in a crystalline solid form, including a substantially pure form, which provides a Raman spectrum substantially in accordance with FIG. 30;
herein designated as Form E.

In another embodiment, the invention relates to (−)-halofenate in a crystalline solid form, including a substantially pure form, which provides at least one of:
(i) an infra red spectrum comprising absorption peaks at about 3475, 3301, 3092, 2969, 2933, 2871, 1750, 1706, 1660, 1597, 1563, 1493, 1460, 1429, 1370, 1338, 1232, 1178, 1126, 1070, 1015, 906, 886 and 820 $cm^{-1}$;
(ii) a Raman spectrum comprising absorption peaks at about 3071, 2969, 2933, 1746, 1657, 1621, 1598, 1448, 1432, 1334, 1291, 1232, 1179, 1094, 1001, 907, 881, 767, 756, 722 and 632 $cm^{-1}$;
(iii) an X-ray powder diffraction pattern comprising peaks at about 11.8° 2θ, and about 13.0° 2θ;
herein designated as Form E.

In another embodiment, the invention relates to (−)-halofenate in a crystalline solid form, including a substantially pure form, which provides an X-ray powder diffraction pattern comprising peaks at about 11.8° 2θ and about 13.0° 2θ; herein designated as Form E.

In yet another embodiment of the invention, the invention relates to (−)-halofenate in a crystalline solid form, including a substantially pure form, which provides an x-ray powder diffraction pattern comprising peaks at about 11.8° 2θ, about 13.0° 2θ and an infrared spectrum comprising at least one peak selected from about 3092 $cm^{-1}$, about 2871 $cm^{-1}$, and about 1563 $cm^{-1}$; herein designated as Form E.

In a further embodiment of the invention, the invention relates to (−)-halofenate in a crystalline solid form, including a substantially pure form, which provides an x-ray powder diffraction pattern comprising peaks at about 11.8° 2θ and about 13.0° 2θ, and a Raman spectrum comprising at least one peak selected from about 2969 $cm^{-1}$, about 1746 $cm^{-1}$, and about 1657 $cm^{-1}$; herein designated as Form E.

In an additional embodiment of the invention, the invention relates to (−)-halofenate in a crystalline solid form, including a substantially pure form, which provides an x-ray powder diffraction pattern comprising peaks at about 11.8° 2θ, about 13.0° 2θ and an infrared spectrum comprising at least one peak selected from about 3092 $cm^{-1}$, about 2871 $cm^{-1}$, and about 1563 $cm^{-1}$, and a Raman spectrum comprising at least one peak selected from about 2969 $cm^{-1}$, about 1746 $cm^{-1}$, and about 1657 $cm^{-1}$; herein designated as Form E.

Further embodiments of the invention include the compound of (−)-halofenate in a crystalline solid Form A characterized by an X-ray powder diffraction pattern comprising a peak at about 10.8° 2θ and an infrared spectrum comprising at least one peak selected from about 3322 $cm^{-1}$ and about 2886 $cm^{-1}$; the compound of (−)-halofenate in a crystalline solid Form A characterized by a an X-ray powder diffraction pattern comprising a peak at about 10.8° 2θ, and a Raman spectrum comprising at least one peak selected from about 3087 $cm^{-1}$ and about 1663 $cm^{-1}$; and the compound of (−)-halofenate in a crystalline solid Form A characterized by an X-ray powder diffraction pattern comprising a peak at about 10.8° 2θ, an infrared spectrum comprising at least one peak selected from about 3322 $cm^{1}$ and about 2886 $cm^{-1}$, and a Raman spectrum comprising at least one peak selected from about 3087 $cm^{-1}$ and about 1663 $cm^{-1}$.

Form A can be generated in higher purity than forms B and C, and form A is the most stable crystalline solid form. Taking these factors into consideration, an optimized crystallization process has been developed wherein (1) (−)-halofenate is dissolved in 6/1 heptane/isopropyl alcohol (2) the solution is seeded with crystals of (−)-halofenate (insoluble at 30° C.), and (3) the solution is cooled and/or concentrated and the API is isolated as crystalline solid form A. Implementation of this process reproducibly provides polymorph A with the level of any single impurity <0.2%.

After many trials it was unexpectedly discovered that when the slurry of the crude product was seeded with Form A, impurities were lowered to 0.04 and 0.11%, respectively. The results are shown below in the Examples.

The optimized process uses a controlled manipulation of the crystalline solid and amorphous forms of (−)-halofenate as the method for providing the API with <0.2% of any single impurity and in the most thermodynamically stable crystal form A.

In another embodiment of the present invention there is provided (−)-halofenate in a crystalline solid form A, including a substantially pure form A, which is obtained by at least one of:
(i) heating (−)-halofenate in at least one solvent selected from the group consisting of heptane, 2-propanol, and combinations thereof; crystallizing at a temperature of from about 50° C. to −10° C. and drying until the crystals contain less than 0.05% solvent;
(ii) drying a crystal of solid form B of (−)-halofenate;
(iii) drying a crystal of solid form C of (−)-halofenate;
(iv) heating (−)-halofenate in at least one solvent selected from the group consisting of heptane, 2-propanol, and combinations thereof; crystallizing in the presence of a crystal of a solid form of (−)-halofenate at a temperature of from about 50° C. to −10° C. and drying until the crystals contain less than 0.05% solvent; and
(v) crystallizing (−)-halofenate from at least one solvent selected from the group consisting of acetonitrile, benzene, cyclohexanol, t-butyl methyl ether and combinations thereof and drying.

Furthermore, the present invention is directed to processes for the preparation of solid forms A, B, C, D and E and an amorphous form. Thus in another embodiment, the invention relates to process for the preparation of (−)-halofenate in a crystalline solid form A, including a substantially pure form A, comprising at least one of:
(i) heating (−)-halofenate in at least one solvent selected from the group consisting of heptane, 2-propanol, and combinations thereof; crystallizing at a temperature of from about 50° C. to −10° C. and drying until the crystals contain less than 0.05% solvent;
(ii) drying a crystal of solid form B of (−)-halofenate;
(iii) drying a crystal of solid form C of (−)-halofenate;
(iv) heating (−)-halofenate in at least one solvent selected from the group consisting of heptane, 2-propanol, and combinations thereof; crystallizing in the presence of a crystal of a solid form of (−)-halofenate at a temperature of from about 50° C. to −10° C. and drying until the crystals contain less than 0.05% solvent; and
(v) crystallizing (−)-halofenate from at least one solvent selected from the group consisting of acetonitrile, benzene, cyclohexanol, t-butyl methyl ether and combinations thereof and drying.

In another embodiment of the present invention there is provided (−)-halofenate in a crystalline solid form B, including a substantially pure form B, which is obtained by crystallizing (−)-halofenate from at least one solvent selected from the group consisting of heptane, 2-propanol, and combinations thereof and at a temperature of from about 20° C. to −10° C. and drying until the crystals contain from about 2 to about 3% solvent.

In another embodiment, the invention relates to process for the preparation of (−)-halofenate in a crystalline solid form B, including a substantially pure form B, comprising crystallizing (−)-halofenate from at least one solvent selected from the group consisting of heptane, 2-propanol, and combinations thereof and at a temperature of from about 20° C. to −10° C. and drying until the crystals contain from about 2 to about 3% solvent.

In another embodiment of the present invention there is provided (−)-halofenate in a crystalline solid form C, including a substantially pure form C, which is obtained by crystallizing (−)-halofenate from at least one solvent selected from the group consisting of heptane, 2-propanol, and combinations thereof and at a temperature of from about 50° C. to 0° C. and drying until the crystals contain about 0.05% to about 0.3% solvent.

In another embodiment, the invention relates to process for the preparation of (−)-halofenate in a crystalline solid form C, including a substantially pure form C, comprising crystallizing (−)-halofenate from at least one solvent selected from the group consisting of heptane, 2-propanol, and combinations thereof and at a temperature of from about 50° C. to 0° C. and drying until the crystals contain about 0.05% to about 0.3% solvent.

In another embodiment of the present invention there is provided (−)-halofenate in a crystalline solid form D, including a substantially pure form D, which is obtained by crystallizing (−)-halofenate from at least one solvent selected from the group consisting of acetone, ethanol, dichloromethane and combinations thereof and drying.

In another embodiment, the invention relates to process for the preparation of (−)-halofenate in a crystalline solid form D, including a substantially pure form D, comprising crystallizing (−)-halofenate from at least one solvent selected from the group consisting of acetone, ethanol, dicloromethane and combinations thereof and drying.

In another embodiment of the present invention there is provided (−)-halofenate in a crystalline solid form E, including a substantially pure form E, which is obtained by crystallizing (−)-halofenate from t-butyl methyl ether and heptane and drying.

In another embodiment, the invention relates to process for the preparation of (−)-halofenate in a crystalline solid form E, including a substantially pure form E, comprising crystallizing (−)-halofenate from t-butyl methyl ether and heptane and drying.

In one embodiment, the invention relates (−)-halofenate in an amorphous form, including a substantially pure form.

In one embodiment, the invention relates (−)-halofenate in an amorphous form, including a substantially pure form, which provides an X-ray powder diffraction pattern substantially in accordance with FIG. 35.

In another embodiment, the invention relates (−)-halofenate in an amorphous form, including a substantially pure form, which provides an X-ray powder diffraction pattern comprising a broad peak substantially between about 15 and about 30° 2θ.

In another embodiment of the present invention there is provided (−)-halofenate in an amorphous form, including a substantially pure form, obtained by heating (−)-halofenate in high humidity.

In another embodiment of the present invention there is provided (−)-halofenate in an amorphous form, including a substantially pure form, obtained by heating (−)-halofenate at greater than about 60° C. for at least about 3 weeks in at least about 74% humidity.

Accordingly in other embodiments, there is provided (−)-halofenate in an isolated form selected from the group consisting of crystalline solid form A, B, C, D, E and amorphous form. Within each of the above embodiments the compound is individually substantially pure form A, is substantially pure form B, is substantially pure form C, is substantially pure form D, is substantially pure form E or amorphous form.

In other embodiments, the invention relates to (−)-halofenate in a substantially pure solid form consisting of greater than 91% (−)-halofenate and less than 9% of chemical impurities other than (−)-halofenate based on the total weight of (−)-halofenate. Within each of the above embodiments, the compound in individual embodiments is greater than 92%, 93%, 94%, 95%, 96%, 97%, 98% and 99% by weight (−)-halofenate.

In another embodiment, the invention relates to (−)-halofenate in a substantially pure solid form consisting of greater than 91% (−)-halofenate form A and less than 9% of other forms of (−)-halofenate based on the total weight of (−)-halofenate. Within each of the above embodiments, the compound in individual embodiments is greater than 92%, 93%, 94%, 95%, 96%, 97%, 98% and 99% of crystalline solid form A by weight of (−)-halofenate.

In another embodiment, the invention relates to (−)-halofenate substantially in a substantially pure solid form which is also substantially free of the (+) isomer. In one embodiment the compound is greater than 91% of the (−)-isomer and less than 9% of the (+) isomer based on the total weight of halofenate. Within each of the above embodiments, the compound in individual embodiments is greater than 92%, 93%, 94%, 95%, 96%, 97%, 98% and 99% of the (−) isomer by weight of halofenate.

In another embodiment the present invention provides a method of enantiomerically enriching (−)-halofenate comprising heating (−)-halofenate in a solvent; crystallizing at a temperature of from about 50° C. to −10° C. and drying until the crystals contain less than 0.05% solvent.

In another embodiment the present invention provides method provides (−)-halofenate in a solvent having an enantiomeric excess of at least about 95%.

A major advantage of these crystalline solid forms is that they are less hygroscopic than the amorphous form. Therefore, the crystalline forms can be better handled and are more stable at normal environmental humidity levels. Because of its non-hygroscopic nature anhydrous crystalline Form A retains a better physical appearance and handling properties over a longer period of time. An improvement in the physical appearance of a dosage form of a drug enhances both physician and patient acceptance and increases the likelihood of success of the treatment.

Further embodiments of the invention include mixtures of the different crystalline solid forms, and the amorphous form, of (−) halofenate. Such mixtures include compositions comprising at least one solid form or at least two solid forms selected from Form A, Form B, Form C, Form D, Form E, and the amorphous form. Any of the analytical techniques described herein may be used to detect the presence of the solid forms in such compositions. Detection may be done qualitatitvely, quantitatively, or semi-quantitatively as those terms as used and understood by those of skill in the solid-state analytical arts.

For these analyses, use of standard analytical techniques involving reference standards may be used. Further, such methods may include use of techniques such as partial-lease squares in conjunction with a diffractive or spectroscopic analytical technique. These techniques may also be used in pharmaceutical compositions of the invention.

Because enantiomers have the same crystalline solid state properties, like X-ray and Raman data (see for example Z. Jane Li et al., *J. Pharm. Sci.,* 1999, 88, pages 337-346) the above invention also relates to the corresponding (+) enantiomer. For the purposes of the present invention, the above crystalline polymorphs and amorphous forms of the (−)-enantiomer are preferred.

(−)-Halofenate in a crystalline solid or amorphous form may be prepared by various methods as further described below in the Examples. The examples illustrate, but do not limit the scope of the present invention. (−)-Halofenate in crystalline solid or amorphous forms may be isolated using typical isolation and purification techniques known in the art, including, for example, chromatographic, recrystallization and other crystallization procedures as well as modification of the procedures outlined above.

III. Pharmaceutical Formulations and Methods of Administration

Besides being directed to different solid forms of (−) halofenate as described herein which includes such forms in an isolated form, in other embodiments there is provided a pharmaceutical composition comprising a therapeutically effective amount of (−)-halofenate of any of the above embodiments in admixture with at least one pharmaceutically acceptable carrier or excipient.

The (−)-halofenate in a substantially pure crystalline solid and/or amorphic form may be used as single components or mixtures. For example, any combinations of Form A, Form B, Form C, Ford D, Form E, and amorphous form may be combined with at least one pharmaceutically acceptable carrier or excipient in a pharmaceutical composition.

As to pharmaceutical compositions of (−)-halofenate it is preferred that these contain 25-100% by weight, especially 50-100% by weight, of a substantially pure form of (−)-halofenate of any of the above embodiments or combinations thereof, based on the total amount of (−)-halofenate. Preferably, such an amount of (−)-halofenate in a substantially pure crystalline solid and/or amorphic form is 75-100% by weight, especially 90-100% by weight. Highly preferred is an amount of 95-100% by weight.

The invention further includes pharmaceutical compositions comprising mixtures of therapeutic amounts of the solid forms of (−)-halofenate which are substantially free of its (+) stereoisomer. For example, therapeutically effective amounts of Form A together with therapeutically effective amounts of at least one of Form B, Form C, Form D, Form E, and the amorphous form, each of which are substantially free of their corresponding (+) stereoisomer could be combined together in a pharmaceutical composition which would then further include at least one pharmaceutically acceptable carrier or excipient.

The invention also includes pharmaceutical compositions containing therapeutically effective amounts of at least one solid form of (−)-halofenate substantially free of its corresponding (+) stereoisomer together with at least one other solid form of (−)-halofenate, substantially free of its corresponding stereoisomer, in a sub-therapeutic dose. Such a sub-therapeutic dose could include, for example, a trace impurity of one of the other solid forms of (−)-halofenate. Such pharmaceutical compositions would further include at least one pharmaceutically acceptable carrier or excipient.

Further embodiments of the invention include as follows.

A pharmaceutical composition comprising a therapeutically effective amount of (−) halofenate in crystalline solid Form A characterized by an X-ray Powder diffraction pattern comprising peaks at about 10.8° 2θ, about 22.0° 2θ, about 29.3° 2θ, and a Raman spectrum comprising at least one peak selected from about 3087 $cm^{-1}$ and about 1663 $cm^{-1}$; and at least one pharmaceutically acceptable carrier or excipient.

A pharmaceutical composition comprising a therapeutically effective amount of (−) halofenate in crystalline solid Form B characterized by an X-ray Powder diffraction pattern comprising peaks at about 6.2° 2θ, about 12.4° 2θ, and at least one peak selected from about 18.8° 2θ, about 20.1° 2θ, and about 14.0° 2θ' and least one pharmaceutically acceptable carrier or excipient.

A pharmaceutical composition comprising a therapeutically effective amount of (−) halofenate in crystalline solid Form C characterized by an X-ray Powder diffraction pattern comprising peaks at about 9.9° 2θ, about 13.3° 2θ, and at least one peak selected from about 15.5° 2θ, about 23.1° 2θ, about 14.7° 2θ, and about 25.9° 2θ; and at least one pharmaceutically acceptable carrier or excipient.

A pharmaceutical composition comprising a therapeutically effective amount of (−) halofenate in crystalline solid Form D characterized by an X-ray Powder diffraction pattern comprising peaks at about 9.6° 2θ and about 17.4° 2θ, and a Raman spectrum comprising at least one peak selected from about 3077 $cm^{-1}$ and about 1329 $cm^{-1}$; and at least one pharmaceutically acceptable carrier or excipient.

A pharmaceutical composition comprising a therapeutically effective amount of (−) halofenate in crystalline solid Form E characterized by an X-ray Powder diffraction pattern comprising peaks at about 11.8° 2θ and about 13.0° 2θ and a Raman spectrum comprising at least one peak selected from about 2969 $cm^{-1}$, about 1746 $cm^{-1}$, and about 1657 $cm^{-1}$; and at least one pharmaceutically acceptable carrier or excipient.

A pharmaceutical composition comprising a therapeutically effective amount of (−) halofenate in an amorphous form characterized by a broad peak between about 15° 2θ and about 30° 2θ; and at least one pharmaceutically acceptable carrier or excipient.

In the methods of the present invention, the (−)-halofenate in a substantially pure crystalline solid and/or amorphic form can be delivered or administered to a mammal, e.g., a human patient or subject, alone, in the form of a pharmaceutically acceptable salt or hydrolyzable precursor thereof, or in the form of a pharmaceutical composition where the compound is mixed with suitable carriers or excipient(s) in a therapeutically effective amount. By a "therapeutically effective dose", "therapeutically effective amount", or, interchangeably, "pharmacologically acceptable dose" or "pharmacologically acceptable amount", it is meant that a sufficient amount of the compound of the present invention, alternatively, a combination, for example, a compound of the present invention, which is substantially free of its (+) stereoisomer, and a pharmaceutically acceptable carrier, will be present in order to achieve a desired result, e.g., alleviating a symptom or complication of Type 2 diabetes. In another example, more than one solid form of (−)halofenate substantially free of its (+) stereoisomer may be prepared in combination with a pharmaceutically acceptable carrier in a sufficient amount to achieve a desired result, e.g., alleviating a symptom or complication of Type 2 diabetes.

The (−)-halofenate in at least one substantially pure crystalline solid and/or amorphic form that are used in the methods of the present invention can be incorporated into a variety of formulations for therapeutic administration. More particularly, the (−)-halofenate in a substantially pure crystalline solid and/or amorphic form can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the (−)-halofenate in at least one substantially pure crystalline solid and/or amorphic form can be achieved in various ways, including oral, buccal, rectal, parenteral, intraperitoneal, intradermal, transdermal, intratracheal administration. Moreover, the (−)-halofenate in a substantially pure crystalline solid and/or amorphic form can be administered in a local rather than systemic manner, in a depot or sustained release formulation. In addition, the compounds can be administered in a liposome.

In addition, the (−)-halofenate in at least one substantially pure crystalline solid and/or amorphic form can be formulated with common excipients, diluents or carriers, and compressed into tablets, or formulated as elixirs or solutions for convenient oral administration, or administered by the intramuscular or intravenous routes. The (−)-halofenate in at least one substantially pure crystalline solid and/or amorphic form can be administered transdermally.

Further embodiments of the invention include pharmaceutical compositions of (−) halofenate, including in therapeutically effective amounts of Form A, and at least one of Form B, Form C, Form D, Form E, and the amorphous form. Said amounts of the at least one of Form B, Form C, Form D, Form E, and the amorphous form may or may not be in therapeutically effective amounts. Such pharmaceutical compositions may be in the form of a solid oral composition such as a tablet or a capsule or as a dry powder for inhalation.

(−)-Halofenate in at least one substantially pure crystalline solid and/or amorphic form can be administered alone, in combination with each other, or they can be used in combination with other known compounds including other therapeutic agents (discussed supra). In pharmaceutical dosage forms, the (−)-halofenate in at least one substantially pure crystalline solid and/or amorphic form can be administered in the form of their pharmaceutically acceptable salts thereof. They can contain hydrolyzable moieties. They can also be used alone or in appropriate association, as well as in combination with, other pharmaceutically active compounds.

Suitable formulations for use in the present invention are found in *Remington's Pharmaceutical Sciences* (Mack Publishing Company (1985) Philadelphia, Pa., 17th ed.), which is incorporated herein by reference. Moreover, for a brief review of methods for drug delivery, see, Langer, *Science* (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the (−)-halofenate in a substantially pure crystalline solid and/or amorphic form can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the (−)-halofenate in a substantially pure crystalline solid and/or amorphic form of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the (−)-halofenate in a substantially pure crystalline solid and/or amorphic form can be formulated readily by combining with pharmaceutically acceptable carriers that are well known in the art. Such carriers enable the (−)-halofenate in a substantially pure crystalline solid and/or amorphic form to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the (−)-halofenate in a substantially pure crystalline solid and/or amorphic form with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different dose combinations of (−)-halofenate in a substantially pure crystalline solid and/or amorphic form.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The (−)-halofenate in a substantially pure crystalline solid and/or amorphous form can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oily or aqueous vehicles, and can contain formulator agents such as suspending, stabilizing and/or dispersing agents.

Pharmaceutical formulations for parenteral administration include aqueous solutions of the (−)-halofenate in a substantially pure crystalline solid and/or amorphous form in water-soluble form. Additionally, suspensions of the (−)-halofenate in a substantially pure crystalline solid and/or amorphous form can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the (−)-halofenate in a substantially pure crystalline solid and/or amorphous form to allow for the preparation of highly concentrated solutions. Alternatively, the active ingredient can be in powder form for constitution with a suitable vehicle, e.g., sterile pyrogen-free water, before use.

The (−)-halofenate in a substantially pure crystalline solid and/or amorphous form can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the (−)-halofenate in a substantially pure crystalline solid and/or amorphous form can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In a presently preferred embodiment, long-circulating, i.e., stealth, liposomes can be employed. Such liposomes are generally described in Woodle, et al., U.S. Pat. No. 5,013,556, the teaching of which is hereby incorporated by reference. The (−)-halofenate in a substantially pure crystalline solid and/or amorphous form of the present invention can also be administered by controlled release means and/or delivery devices such as those described in U.S. Pat. Nos. 3,845,770; 3,916,899; 3,536,809; 3,598,123; and 4,008,719; the disclosures of which are hereby incorporated by reference.

Certain organic solvents such as dimethylsulfoxide (DMSO) also can be employed, although usually at the cost of greater toxicity. Additionally, the (−)-halofenate in a substantially pure crystalline solid and/or amorphous form can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any of the (−)-halofenate in a substantially pure crystalline solid and/or amorphous form used in the method of the present invention, a therapeutically effective dose can be estimated initially from cell culture assays or animal models.

Moreover, toxicity and therapeutic efficacy of the (−)-halofenate in a substantially pure crystalline solid and/or amorphous form described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. (−)-Halofenate in a substantially pure crystalline solid and/or amorphous form which exhibit high therapeutic indices are preferred. The data obtained from these cell culture assays and animal studies can be used in formulating a dosage range that is not toxic for use in human. The dosage of such (−)-halofenate in a substantially pure crystalline solid and/or amorphous form lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition (see, e.g., Fingl et al. 1975 In: *The Pharmacological Basis of Therapeutics*, Ch. 1).

The amount of (−)-halofenate in a substantially pure crystalline solid and/or amorphic form that can be combined with a carrier material to produce a single dosage form will vary depending upon the disease treated, the mammalian species, and the particular mode of administration. However, as a general guide, suitable unit doses for the (−)-halofenate in a substantially pure crystalline solid and/or amorphic form of the present invention can, for example, preferably contain between 100 mg to about 3000 mg of the active compound. A preferred unit dose is between 500 mg to about 1500 mg. A more preferred unit dose is between 500 to about 1000 mg. Such unit doses can be administered more than once a day, for example 2, 3, 4, 5 or 6 times a day, but preferably 1 or 2 times per day, so that the total daily dosage for a 70 kg adult is in the range of 0.1 to about 250 mg per kg weight of subject per administration. A preferred dosage is 5 to about 250 mg per kg weight of subject per administration, and such therapy can extend for a number of weeks or months, and in some cases, years. It will be understood, however, that the specific dose level for any particular patient will depend on a variety of factors including the activity of the specific form of the (−)-halofenate employed; the age, body weight, general health, sex and diet of the individual being treated; the time and route of administration; the rate of excretion; other drugs which have previously been administered; and the severity of the particular disease undergoing therapy, as is well understood by those of skill in the area.

A typical dosage can be one 10 to about 1500 mg tablet taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to interrupt, adjust, or terminate therapy in conjunction with individual patient response.

IV. Methods of Treatment

A. Modulating Insulin Resistance, Type 2 Diabetes and Hyperlipidemia

In another embodiment, the present invention encompasses a method of modulating insulin resistance in a mammal, the method comprising administering to the mammal a therapeutically effective amount of (−)-halofenate in a substantially pure crystalline solid and/or amorphous form. The method avoids the adverse effects associated with the administration of a racemic mixture of halofenate by providing an enriched amount of the (−) stereoisomer of halofenate in a crystalline solid or amorphous form which is insufficient to cause the adverse effects associated with the inhibition of cytochrome P450 2C9.

The present invention also encompasses a method of modulating Type 2 diabetes in a mammal, the method comprising administering to the mammal a therapeutically effective amount of (−)-halofenate in a substantially pure crystalline solid and/or amorphous form. The method avoids the adverse effects associated with the administration of a racemic mixture of halofenate by providing an enriched amount of the (−) stereoisomer of halofenate in a crystalline solid or amorphous form which is insufficient to cause the adverse effects associated with the inhibition of cytochrome P450 2C9.

The present invention further encompasses a method of modulating hyperlipidemia in a mammal, the method comprising administering to the mammal a therapeutically effective amount of a (−)-halofenate in a substantially pure crystalline solid and/or amorphic form. The method avoids the adverse effects associated with the administration of a racemic mixture of halofenate by providing an enriched amount of the (−) stereoisomer of halofenate in a crystalline solid or amorphous form which is insufficient to cause the adverse effects associated with the inhibition of cytochrome P450 2C9.

The racemic mixture of halofenate (i.e., a 1:1 racemic mixture of the two enantiomers) possesses antihyperlipidemic activity and provides therapy and a reduction of hyperglycemia related to diabetes when combined with certain other drugs commonly used to treat this disease. However, this racemic mixture, while offering the expectation of efficacy, causes adverse effects. The term "adverse effects" includes, but is not limited to, nausea, gastrointestinal ulcers, and gastrointestinal bleeding. Other side effects that have been reported with racemic halofenate include potential problems with drug-drug interactions, especially including difficulties controlling anticoagulation with COUMADIN™. Utilizing substantially pure compounds of the present invention results in clearer dose related definitions of efficacy, diminished adverse effects, and accordingly, an improved therapeutic index. As such, it has now been discovered that it is more desirable and advantageous to administer the (−) enantiomer of halofenate instead of racemic halofenate.

B. Combination Therapy with Additional Active Agents

The compositions can be formulated and administered in the same manner as detailed below. "Formulation" is defined as a pharmaceutical preparation that contains a mixture of various excipients and key ingredients that provide a relatively stable, desirable and useful form of a compound or drug. For the present invention, "formulation" is included within the meaning of the term "composition." The (−)-halofenate in a substantially pure crystalline solid and/or amorphic form of the present invention can be used effectively alone or in combination with one or more additional active agents depending on the desired target therapy (see, e.g., Turner, N. et al. *Prog. Drug Res.* (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165-71; United Kingdom Prospective Diabetes Study Group: UKPDS 28, *Diabetes Care* (1998) 21: 87-92; Bardin, C. W.,(ed.), CURRENT THERAPY IN ENDOCRINOLOGY AND METABOLISM, 6th Edition (Mosby—Year Book, Inc., St. Louis, Mo. 1997); Chiasson, J. et al., *Ann. Intern. Med.* (1994) 121: 928-935; Coniff, R. et al., *Clin. Ther.* (1997) 19: 16-26; Coniff, R. et al., *Am. J. Med.* (1995) 98: 443-451; and Iwamoto, Y. et al, *Diabet. Med.* (1996) 13 365-370; Kwiterovich, P. *Am. J. Cardiol* (1998) 82(12A): 3 U-17 U). These studies indicate that diabetes and hyperlipidemia modulation can be further improved by the addition of a second agent to the therapeutic regimen. Combination therapy includes administration of a single pharmaceutical dosage formulation which contains (−)-halofenate in a substantially pure crystalline solid and/or amorphic form and one or more additional active agents, as well as administration of (−)- halofenate in a substantially pure crystalline solid and/or amorphic form and each active agent in its own separate pharmaceutical dosage formulation. For example, a (−)-halofenate in a substantially pure crystalline solid and/or amorphic form and an HMG-CoA reductase inhibitor can be administered to the human subject together in a single oral dosage composition, such as a tablet or capsule, or each agent can be administered in separate oral dosage formulations. Where separate dosage formulations are used, (−)-halofenate in a substantially pure crystalline solid and/or amorphic form and one or more additional active agents can be administered at essentially the same time (i.e., concurrently), or at separately staggered times (i.e., sequentially). Combination therapy is understood to include all these regimens.

An example of combination therapy that modulates (prevents the onset of the symptoms or complications associated) atherosclerosis, wherein (−)-halofenate in a substantially pure crystalline solid and/or amorphic form is administered in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin. As noted above, the (−)-halofenate in a substantially pure crystalline solid and/or amorphic form can be administered in combination with more than one additional active agent, for example, a combination of (−)-halofenate in a substantially pure crystalline solid and/or amorphic form with an HMG-CoA reductase inhibitor (e.g., lovastatin, simvastatin and pravastatin) and aspirin, or (−)-halofenate in a substantially pure crystalline solid and/or amorphic form with an HMG-CoA reductase inhibitor and a β-blocker.

Another example of combination therapy can be seen in treating obesity or obesity-related disorders, wherein the (−)-halofenate in a substantially pure crystalline solid and/or amorphic form can be effectively used in combination with, for example, phenylpropanolamine, phentermine, diethylpropion, mazindol; fenfluramine, dexfenfluramine, phentiramine, $β_3$ adrenoceptor agonist agents; sibutramine, gastrointestinal lipase inhibitors (such as orlistat), and leptins. Other agents used in treating obesity or obesity-related disorders wherein the (−)-halofenate in a substantially pure crystalline solid and/or amorphic form can be effectively used in combination with, for example, neuropeptide Y, enterostatin, cholecytokinin, bombesin, amylin, histamine $H_3$ receptors, dopamine $D_2$ receptors, melanocyte stimulating hormone, corticotrophin releasing factor, galanin and gamma amino butyric acid (GABA).

Still another example of combination therapy can be seen in modulating diabetes (or treating diabetes and its related symptoms, complications, and disorders), wherein the (−)-halofenate in a substantially pure crystalline solid and/or amorphic form can be effectively used in combination with, for example, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone) and other insulin sensitizers (such as Muraglitazar, AMG-131/T-131, tesaglitazar, DRF-10945, AZD-4619, E-3030, GSK-677954, GW-501516, GW-590735, R-483, KRP-101, GSK-641597, LY-674, LY-929, naveglitazar, netoglitazone, MBX-2044, NS-220, LBM-642, NO-5129, PLX-204 and M-24); dehydroepiandrosterone (also referred to as DHEA or its conjugated sulphate ester, $DHEA-SO_4$); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the active agents discussed above for treating atherosclerosis.

A further example of combination therapy can be seen in modulating hyperlipidemia (treating hyperlipidemia and its related complications), wherein the (−)-halofenate in a substantially pure crystalline solid and/or amorphic form can be effectively used in combination with, for example, statins (such as fluvastatin, lovastatin, pravastatin or simvastatin), bile acid-binding resins (such as colestipol or cholestyramine), nicotinic acid, probucol, betacarotene, vitamin E, or vitamin C.

In accordance with the present invention, a therapeutically effective amount of a (−)-halofenate in a substantially pure crystalline solid and/or amorphic form can be used for the preparation of a pharmaceutical composition useful for treating diabetes, treating hyperlipidemia, treating obesity, lowering triglyceride levels, lowering cholesterol levels, raising the plasma level of high density lipoprotein, and for treating, preventing or reducing the risk of developing atherosclerosis.

Additionally, an effective amount of (−)-halofenate in a substantially pure crystalline solid and/or amorphic form and a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate, and gemfibrizol; vitamin $B_6$ and the pharmaceutically acceptable salts thereof; vitamin $B_{12}$; an anti-oxidant vitamin; a β-blocker; an angiotensin II antagonist; an angiotensin converting enzyme inhibitor; a platelet aggregation inhibitor; a fibrinogen receptor antagonist; aspirin; phentiramines, $β_3$ adrenergic receptor agonists; sulfonylureas, biguanides, α-glucosidase inhibitors, other insulin secretogogues, and insulin can be used together for the preparation of a pharmaceutical composition useful for the above-described treatments.

In addition, the present invention provides for kits with unit doses of (−)-halofenate in a substantially pure crystalline solid and/or amorphous form either in oral or injectable doses. In addition to the containers containing the unit doses will be an informational package insert describing the use and attendant benefits of the drugs in alleviating symptoms and/or complications associated with Type 2 diabetes as well as in alleviating hyperlipidemia. Preferred compounds and unit doses are those described herein above.

It should be understood that the foregoing discussion, embodiments and examples merely present a detailed description of certain preferred embodiments and are in no way limiting. It will be apparent to those of ordinary skill in the art that various modifications and equivalents can be made without departing from the spirit and scope of the invention. All the patents, journal articles and other documents discussed or cited above are herein incorporated by reference.

V. Examples

The (−)-halofenate in a substantially pure crystalline solid and/or amorphous form of the present invention can be readily prepared using the processes set forth from the following examples which are illustrative.

A. Instrumental

1. X-Ray Powder Diffraction

X-ray powder diffraction (XRPD) analyses were performed using either a Shimadzu XRD-6000 X-ray powder diffractometer or an Inel XRG-3000 diffractometer. The Shimadzu XRD-6000 X-ray powder diffractometer used Cu Kα radiation, and is equipped with a long fine focus x-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40° 2θ was used. A silicon standard was analyzed to check the instrument alignment. Data were collected and analyzed using XRD-6000 v. 4.1. Samples were prepared for analysis by placing them in an aluminum holder with a silicon insert.

A Bragg-Brentano instrument like the Shimadzu system used for measurements reported herein, a systematic peak shift (all peaks are shifted in the same direction by a same degree) in ° 2θ can result from sample preparation errors as described in Chen et al.; *J Pharmaceutical and Biomedical Analysis,* 2001; 26, 63. This systematic peak shift can occur in the range of up to about 0.2° 2θ.

The Inel XRG-3000 diffractometer is equipped with a CPS (Curved Position Sensitive) detector with a 2θ range of 120°. Real time data were collected using Cu-Kα radiation starting at approximately 4° 2θ at a resolution of 0.03° 2θ. The tube voltage and amperage were set to 40 kV and 30 mA, respectively. The pattern is displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for 5 or 10 min. Instrument calibration was performed using a silicon reference standard.

2. Thermal Analysis

Differential scanning calorimetry (DSC) was performed using a TA Instruments 2920 differential scanning calorimeter. The sample was placed into an aluminum DSC pan and the weight accurately recorded. The pan was covered with a lid and then crimped. The sample cell was equilibrated at 25° C. and heated under a nitrogen purge at a rate of 10° C./min, up to a final temperature of 350° C. Indium metal was used as the calibration standard. Reported temperatures are at the transition maxima.

Thermographic analyses (TGA) was performed using a TA Instruments 2920 thermographic analyzer. The sample was placed into an aluminum sample pan and inserted into a TGA furnace. The sample was first equilibrated at 25° C., then heated under a nitrogen at a rate of 10° C./min, up to a final temperature of 350° C. Nickel and ALUMEL™ were used as calibration standards.

3. Cyclic DSC

Cyclic differential scanning calorimetry (DSC) was performed using a TA Instruments 2920 differential scanning calorimeter. The sample was placed into an aluminum DSC pan and the weight accurately recorded. The pan was covered with a lid and then crimped. The method was as follows:
1. Ramp 10° C./min. to 90° C.
2. Isothermal for 15 min.
3. Equilibrate at −50° C.
4. Isothermal for 5 min.
5. Ramp 10° C./min. to 140 or 200° C.

Indium metal was used as the calibration standard. Reported temperatures are at the transition maxima.

4. Hot Stage Microscopy

Hot stage microscopy was performed using a Linkam hot stage (model FTIR 600) mounted on a Leica DM LP microscope. Samples were observed at a magnification range of 100× to 400× with a lambda plate with crossed polarizers. Samples were placed on a coverslip and a drop of silicon oil. Another coverslip was then placed over the sample. Each sample was visually observed as the stage was heated. Images were captured for some of the samples. The hot stage was calibrated using USP melting point standards.

5. Optical Microscopy

Optical microscopy was performed using a Wolfe polarizing microscope when no images were captured. Samples observed at a magnification range of 20× to 40× with and without cross polarizers. Samples were placed on a glass slide or viewed within the vial. For captured images, polarized light microscopy was performed using a Leica DM LP microscope. Samples were observed at a magnification range of 50× to 400× with a lambda plate with crossed polarizers. Samples were placed on a glass slide.

6. Infrared Spectroscopy

Infrared spectra were acquired on a MAGNA-IR 860® Fourier transform infrared (FT-IR) spectrophotometer (Thermo Nicolet) equipped with an extended range potassium bromide (KBr) beamsplitter, and a deuterated triglycine sulfate (DTGS) detector. A diffuse reflectance accessory (THE COLLECTOR™, Thermo Spectra-Tech) was used for sampling. Each spectrum represents 128 co-added scans collected at a spectral resolution of 4.000 cm$^{-1}$. Sample preparation consisted of placing the sample into a 3 or 13-mm diameter cup. A background data set was acquired with an alignment mirror in place. A Log 1/R (R=reflectance) spectrum was acquired by taking a ratio of these two data sets against each other. Wavelength calibration was performed using polystyrene.

7. Raman Spectroscopy

FT-Raman spectra were acquired on an FT-Raman 960 spectrometer (Thermo Nicolet). This spectrometer uses an excitation wavelength of 1064 nm. Approximately 1.011 W of Nd:YVO$_4$ laser power was used to irradiate the sample. The Raman spectra were prepared for analysis by palacing the material in a glass tube and positioning the tube in a gold-coated tube holder in the accessory, or placing the sample into a gold-coated capillary holder. A total of 256 sample scans were collected from 3600-98 cm$^{-1}$ at a spectral resolution of 4.000 cm$^{-1}$, using Happ-Genzel apodization. Wavelength calibration was performed using sulfur and cyclohexane.

8. NMR Spectroscopy

Solution $^1$H NMR spectra were acquired for the as-received material at ambient temperature on a Bruker Instruments AM-250 spectometer at a magnetic field strength of 5.87 Tesla ($^1$H Larmor frequency=250 MHz). The sample was prepared by dissolving 0.7-0.8 mg sample in ca. 0.5 mL of NMR-grade DMSO-d$_6$. Spectra were acquired with a 1H pulse width of 7.5 μs a 2.34 second acquisition time, a 5 second delay between scans, a spectral width of 3496.5 Hz with 16384 data points, and 128 transients. Each free indication decay (FID) was processed with GRAMS/32 AI software v. 6.00 using a Fourier number equal to twice the number of acquired points with an exponential line broadening factor of 0.43 Hz to improve sensitivity. Peak tables were generated by the GRAMS software peak picking algorithm. Spectra were referenced to internal TMS at 0.0 ppm.

9. Automated Moisture Sorption/Desorption

Moisture sorption/desorption data were collected on a VTI-SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes with a maximum equilibration time of 3 hours if the weight criterion was not met. Data were not corrected for the initial moisture content of the samples. Sodium chloride and polyvinylpyrolidone were used as calibration standards. A sample was taken after desorption was complete and analyzed by powder X-ray diffraction for potential form change.

B. Preparation Methods for Forms A, B, C, D, E, and Amorphous

EXAMPLE 1

Crystallization of (−)-Halofenate Form A

Method i.

A 100-mL bottom-drain reactor was charged with 2.62 g of (−)-halofenate (94.2% ee) and 26.2 g of 6/1 (v/v) heptane/2-propanol. The mixture was heated to 39° C. to give a solution, then cooled to 10° C. at a rate of 1° C./min to give a slurry; the slurry was heated to obtain a light slurry at 23° C. The light slurry was cooled to 6.2° C. at a rate of 0.05° C./min and held for about 10 hours before the solid was isolated by vacuum filtration. Vacuum oven drying at room temperature afforded 1.57 g (60% recovery, 99.76% ee) of (−)-halofenate Form B containing about 2-3% heptane. Further vacuum oven drying at about 50° C. afforded Form C containing heptane, but at a concentration of about 0.3%. Further vacuum oven drying at about 50° C. afforded Form A containing no more than about 0.05% heptane.

Method ii.

(−)-halofenate form B was heated to melting and allowed to cool at ambient conditions to afford Form A.

Method iii.

(−)-halofenate form C was heated to melting and allowed to cool at ambient conditions to afford Form A.

Method iv.

A 200-mL, glass-jacketed vessel with a Teflon, bottom plug-valve was set up with a three-bladed impeller (pitched for down-flow pumping) and a hastelloy thermocouple. The crystallizer vessel head was also equipped with a condenser having a nitrogen bubbler atop. (−)-Halofenate (4.5 g, dried) and solvent [46.8 g of n-heptane (Phillips Pure Grade): 2-propanol (Fisher HPLC Grade), 6:1, v:v] were added to a 100-mL, one-necked flask with a magnetic stirring bar. A condenser was placed in the neck and the flask was heated to a solution in a water bath at about 50° C. The solution was filtered through a 0.5 mm PTFE filter on a HPLC solvent filtration apparatus. The filtrate was poured to the crystallizer vessel and totaled 49.6 g. The amount of solute in the solution which was lost to the dissolution/filtration equipment was estimated at 0.15 g. The solution was cooled to 30° C. and seed with 0.0303 g of (−)-halofenate (Form A). The contents were stirred at 275 rpm and cooled by setting the jacket setpoint to 27° C. Additional nucleation was observed during cool-down at 28° C., 13 minutes after seeding. A thicker slurry developed over about 1.5 hours at 27° C. The suspension was heated to 28° C., held for 0.75 hours, and then cooled using the following jacket profile: from 28 to 20° C. at 0.833° C./hour, from 20 to 8° C. at 2.40° C./hour, from 8 to −6° C. at 3.50° C./hour. The slurry was held for 5 hours at −6° C. before isolation by suction filtration on a 60-mL, C-fritted, glass funnel. The mother liquor (38.32 g) was clear and colorless. Chilled n-heptane (13.8 g) was added to the vessel as a rinse and top-loaded to the wetcake. The wash was combined with the previous mother liquor and totaled 51.94 g. The washed wetcake (5.62 g) was transferred to a dish and dried in a vacuum oven for 19 hours at room temperature. The dry product (3.42 g, 78.6% isolated yield) was analyzed by XRD and matched the pattern of the Form A crystal structure. By HPLC, (+)-halofenate was not detected in the crystal product. By NMR, the product contained 0.04% heptane. The mother liquor and wash solution contained about 0.079% (+)-halofenate and 1.39% (−)-halofenate.

Method v.

A 50-gallon glass-lined steel reactor equipped with a 12" diameter 3-bladed retreat curve agitator was charged with 21 lb of crude (−)-halofenate, 177 lb of n-heptane and 34 lb of 2-propanol. The mixture was heated to 48° C. to completely dissolve the (−)-halofenate. The reactor solution was pressure transferred to a similarly equipped 100 gallon glass-lined steel reactor through a 0.2 micron polish filter to remove any potential solid contaminants. The transfers typically required about 10 minutes. About 9 lb of n-heptane and 2 lb of 2-propanol were loaded to a 50-gallon glass-lined steel reactor equipped with a 12" diameter 3-bladed retreat curve agitator. After heating to 50° C., the solvent was pressure transferred to the 100-gallon reactor to flush the transfer line and filter. The 100-gallon reactor solution was cooled form 50° C. to 27° C. at 12° C./hr. The supersaturated solution was seeded with about 50 grams of (−)-halofenate. The seed crystals were mixed with n-heptane and the resulting slurry was vacuum loaded through the reactor sample line. The 100-gallon reactor contents were held at 27° C. until nucleation occurred. Typically a white slurry was visible after about 30 minutes. The (−)-halofenate in 100-gallon reactor was crystallized by cooling. The typical jacket cooling profile was: cool from 27 to 20° C. at 1° C./hr, 20 to 8° C. at 2.4° C./hr and 8 to −8° C. at 3.5° C./hr. After holding the 100-gallon reactor slurry below −8° C. for 4 hours, the slurry was transferred to a 30" diameter 316 stainless steel centrifuge to isolate the product by centrifugation on a 1-3 micron polypropylene filter cloth. The reactor was rinsed with 60 lb of n-heptane to remove any product still remaining in the reactor. Finally the wetcake was washed with 32 lb of chilled n-heptane through the centrifuge wash nozzles. About 33 lb of wetcake was unloaded form the centrifuge (ca. 50% loss-on-drying). The wetcake was dried in either a laboratory vacuum oven or a 3-cubic foot glass-lined tumble dryer at 25° C. until the LOD was below 0.3%. The dry product was unloaded to line fiber packages through a 3 mesh wire screen.

Method vi.

Approximately 66 mg of (−)-halofenate was dissolved in approximately 2 mL of acetonitrile. Approximately 1 mL of the solution was filtered using a 0.2 μm nylon syringe filter into an open 20 mL scintillation vial. The solution was allowed to dry at ambient conditions in a fume hood to white solids.

Method vii.

Approximately 65 mg of (−)-halofenate was dissolved in 0.5 mL of acetonitrile was filtered through a 0.2 μm nylon syringe filter. Added 15 mL of water to the solution and vortexed briefly. A slightly cloudy solution was obtained. The solution was centrifuged for 5 minutes at ambient temperature. A colorless solution with a small amount of solid was produced. The solid was collected, dried in fume hood.

Method viii.

Approximately 60 mg of (−)-halofenate was dissolved in approximately 2 mL of benzene. Approximately 1 mL of the solution was filtered using a 0.2 μm nylon syringe filter into a 20 mL scintillation vial covered with an aluminum foil containing a pinhole. The solution was allowed to dry at ambient conditions in a fume hood to white solids.

Method ix.

Approximately 53 mg of (−)-halofenate was dissolved in approximately 2 mL of cyclohexanol. Approximately 1 mL of the solution was filtered using a 0.2 μm nylon syringe filter into an open 20 mL scintillation via. Allowed to dry at ambient conditions in a fume hood to white solids.

Method x.

Approximately 51 mg of (−)-halofenate was dissolved in approximately 2 mL tertiary-butyl methyl ether. Approximately 1 mL of the solution was filtered using a 0.2 μm nylon syringe filter into an open 20 mL scintillation via. Allowed to dry at ambient conditions in a fume hood to white solids.

Method xi.

Approximately 97 mg of (−)-halofenate was dissolved in approximately 2 mL of toluene. Approximately 1 mL of the solution was filtered using a 0.2 μm nylon syringe filter into an open 20 mL scintillation vial. Allowed to dry at ambient conditions in a fume hood to white solids.

EXAMPLE 2

Crystallization of (−)-Halofenate Form B

Method i.

A 100-mL bottom-drain reactor was charged with 2.62 g of (−)-halofenate (94.2% ee) and 26.2 g of 6/1 (v/v) heptane/2-propanol. The mixture was heated to 39° C. to give a solution, then cooled to 10° C. at a rate of 1° C./min to give a slurry; the slurry was heated to obtain a light slurry at 23° C. The light slurry was cooled to 6.2° C. at a rate of 0.05° C./min and held for about 10 hours before the solid was isolated by vacuum filtration. Vacuum oven drying at room temperature afforded 1.57 g (60% recovery, 99.76% ee) of (−)-halofenate containing about 2-3% heptane.

Method ii.

Approximately 200 mg of (−)-halofenate was charge to a glass vial. 2.57 mL heptane were pipetted to the vial, followed by 0.43 mL 2-propanol (3 mL heptane/IPA 6:1, v:v). The sample was vortexed for a few minutes; much solid remained. The vial was then placed in a controlled temperature bath (water/anti-freeze) at ca. 25° C. The temperature of the bath was raised in small increments to dissolve the entire solid. The sample was removed periodically for brief vortexing. At 40° C., after more than 30 minutes, the entire solid had dissolved.

The resulting solution was hot-filtered into two clean glass vials. Both vials were kept in the 40° C. bath for approximately 10 minutes to ensure no precipitation of the solid from filtering. The temperature of the bath was slowly lowered to 18° C. After more than five and half hours, the bath temperature reached 18° C., and one of the vials was placed in the freezer (ca. −20° C.). Neither sample appeared to containing any solid. The bath temperature was then raised to 25° C. After more than 15 minutes at 25° C., the second vial was placed in the same freezer. This sample contained no solid upon entering the freezer.

After being stored overnight in the freezer both samples were thick with solid. The samples were warmed to ambient, and the supernatant was removed. A small portion of each solid sample was transferred to a glass slide and analyzed by polarized light microscopy. The slide was stored under ambient conditions and submitted for single crystal X-ray. A portion of each of the vial samples was analyzed by Inel capillary XRPD; the capillaries were packed while the solids were wet.

The vials containing the remaining samples were left uncapped in the fume hood to air-dry the solids. The solids were dried approximately 5 hours, and the vials were capped. The vials were left at ambient for about a day. Approximately 12 mg of one of the samples was transferred to a clean vial and dried upon vacuum at ambient temperature for about 5 hours. The vacuum-dried sample was analyzed by Inel capillary XRPD. the air-dried samples were move to the refrigerator (ca. 4° C.) for storage.

Method iii.

Approximately 200 mg of (−)-halofenate was dissolved in approximately 2.5 mL of heptane and approximately 0.4 mL of 2-propanol. The sample was heated for approximately 50 minutes in a 40° C. water bath yielding a clear solution. Approximately half of the solution was then filtered while hot through a warm 0.2 μm nylon syringe filter. The filtered solution was returned to the water bath and cooled to 18° C. for approximately 4.5 hours. No precipitation observed. Sample was transferred to a freezer at approximately −17° C. overnight. Sample was removed from freezer and decanted supernatant off as solution warmed to ambient temperature to recover white solids.

EXAMPLE 3

Crystallization of (−)-Halofenate Form C

A 100-mL bottom-drain reactor was charged with 2.62 g of (−)-halofenate (94.2% ee) and 26.2 g of 6/1 (v/v) heptane/2-propanol. The mixture was heated to 39° C. to give a solution, then cooled to 10° C. at a rate of 1° C./min to give a slurry; the slurry was heated to obtain a light slurry at 23° C. The light slurry was cooled to 6.2° C. at a rate of 0.05° C./min and held for about 10 hours before the solid was isolated by vacuum filtration. Vacuum oven drying at room temperature afforded 1.57 g (60% recovery, 99.76% ee) of (−)-halofenate containing about 2-3% heptane. Further vacuum oven drying at about 50° C. afforded Form C containing heptane, but at a concentration of at about 0.3%.

EXAMPLE 4

Crystallization of (−)-Halofenate Form D

Method i.

Approximately 52 mg of (−)-halofenate was dissolved in approximately in 1 mL of acetone. The solution was filtered using a 0.2 μm nylon syringe filter and the filtered solution was rotary evaporated. The resulting sample was dried under vacuum at ambient temperature to give white solids.

Method ii.

Approximately 59 of mg of (−)-halofenate was dissolved in approximately 2 mL of ethanol. Approximately 1 mL of the solution was filtered using a 0.2 μm nylon syringe filter into an open 20 mL scintillation vial. Allowed to dry at ambient conditions in a fume hood to white solids.

EXAMPLE 5

Crystallization of (−)-Halofenate Form E

Approximately 60 mg of (−)-halofenate was dissolved in 0.5 mL of tertiary-butyl methyl ether. The solution was filtered using a 0.2 μm nylon syringe filter into 40 mL of cold heptane cooled in a dry ice/acetone bath and capped. Solution became cloudy and solids formed after approximately an hour. The solid was recovered by pouring out the solution. The sample was vacuum dried at ambient temperature to yield white powder.

EXAMPLE 6

Preparation of Amorphous (−)-Halofenate

Approximately 114 mg of (−)-halofenate was chopped to a fine powder and placed in an open vial. The vial was placed into a jar containing a saturated salt solution at approximately 74% relative humidity and placed it an oven at 60° C. for 3 weeks. The sample became clear/colorless liquid that quickly converted into a clear to off-white gel when removed from the jar. The off-white gel was amorphous.

EXAMPLE 7

Slurry Interconversion Studies

Samples of mixed forms by XRPD and pure forms were used for interconversion studies (see FIG. 37).

A saturated solution was prepared by vortexing and sonicating ca. 4 mg (−)-halofenate Form A in approximately 5-6 mL cyclohexane. This solution was filtered into a sample containing a mixture of ca. 40 mg Form A/Form D. The mixture was slurred on a rotating wheel at ambient temperature for approximately 6 days. The solids were recovered by vacuum filtration and vacuum dried at ambient temperature. The dry solids were analyzed by polarized light microscopy and XRPD.

The experiment was repeated using a shaker block at ca 50° C. using 2 mL of cyclohexane and slurried for ca. 3 days. and the supernatant was removed through decantation. Both the ambient and 50° C. experiments were repeated using pure forms A and E (ca. 20 mg of each form). The ambient experiment was also repeated with A, B, D, and E (ca. 10 mg of each form, slurred approximately 7 days) on a rotating wheel and on a magnetic stir plate in the refrigerator (ca 5° C.). When conversion was not deemed complete by XRPD solids were re-slurried in cyclohexane.

Interconversion studies were carried out in cyclohexane at ambient temperature 50° C. and 5° C. (see FIG. 37). The solvent was chosen because of the high solubility of the various forms in common organic solvents. Forms A, B, D and E were used as starting materials. All slurries resulted in Form A. This confirms that Form A is the most stable crystal form of (−)-halofenate.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A pharmaceutical composition comprising a pharmaceutically acceptable excipient and a therapeutically effective amount of the compound (−)-halofenate in a crystalline solid form A characterized by an X-ray powder diffraction pattern comprising a peak at about 10.8° 2θ and an infrared spectrum comprising at least one peak selected from at about 3322 cm$^{-1}$ and at about 2886 cm$^{-1}$.

2. The pharmaceutical composition of claim 1 where the crystalline solid form A consists of greater than 95% by weight (−)-halofenate and less than 5% by weight of other non-solvent compounds.

3. The pharmaceutical composition of claim 1 where the composition is a solid oral composition.

4. The pharmaceutical composition of claim 3 where the composition is a tablet or capsule.

5. A pharmaceutical composition comprising a pharmaceutically acceptable excipient and a therapeutically effective amount of the compound (−)-halofenate in a crystalline solid form A characterized by an X-ray powder diffraction pattern comprising a peak at about 10.8° 2θ and a Raman spectrum comprising at least one peak selected from at about 3087 cm$^{-1}$ and at about 1663 cm$^{-1}$.

6. The pharmaceutical composition of claim 5 where the crystalline solid form A consists of greater than 95% by weight (−)-halofenate and less than 5% by weight of other non-solvent compounds.

7. The pharmaceutical composition of claim 5 where the composition is a solid oral composition.

8. The pharmaceutical composition of claim 7 where the composition is a tablet or capsule.

9. A pharmaceutical composition comprising a pharmaceutically acceptable excipient and a therapeutically effective amount of the compound (−)-halofenate in a crystalline solid form A characterized by an X-ray powder diffraction pattern comprising a peak at about 10.8° 2θ, an infrared spectrum comprising at least one peak selected from at about 3322 cm$^{-1}$ and at about 2886 cm$^{-1}$, and a Raman spectrum comprising at least one peak selected from at about 3087 cm$^{-1}$ and at about 1663 cm$^{-1}$.

10. The pharmaceutical composition of claim 9 where the crystalline solid form A consists of greater than 95% by weight (−)-halofenate and less than 5% by weight of other non-solvent compounds.

11. The pharmaceutical composition of claim 9 where the composition is a solid oral composition.

12. The pharmaceutical composition of claim 11 where the composition is a tablet or capsule.

13. A pharmaceutical composition comprising a pharmaceutically acceptable excipient and a therapeutically effective amount of the compound (−)-halofenate in a crystalline solid form A characterized by an X-ray powder diffraction pattern comprising peaks at about 10.8° 2θ, about 22.0° 2θ, and about 29.3° 2θ; and an infrared spectrum comprising peaks at about 3322 $cm^{-1}$ and about 2886 $cm^{-1}$.

14. The pharmaceutical composition of claim 13 where the crystalline solid form A consists of greater than 95% by weight (−)-halofenate and less than 5% by weight of other non-solvent compounds.

15. The pharmaceutical composition of claim 13 where the composition is a solid oral composition.

16. The pharmaceutical composition of claim 15 where the composition is a tablet or capsule.

17. A pharmaceutical composition comprising a pharmaceutically acceptable excipient and a therapeutically effective amount of the compound (−)-halofenate in a crystalline solid form A characterized by an X-ray powder diffraction pattern comprising peaks at about 10.8° 2θ, about 22.0° 2θ, and about 29.3° 2θ; and a Raman spectrum comprising peaks at about 3087 $cm^{-1}$ and about 1663 $cm^{-1}$.

18. The pharmaceutical composition of claim 17 where the crystalline solid form A consists of greater than 95% by weight (−)-halofenate and less than 5% by weight of other non-solvent compounds.

19. The pharmaceutical composition of claim 17 where the composition is a solid oral composition.

20. The pharmaceutical composition of claim 19 where the composition is a tablet or capsule.

* * * * *